United States Patent
Blaschuk et al.

(10) Patent No.: US 7,138,369 B2
(45) Date of Patent: *Nov. 21, 2006

(54) COMPOUNDS AND METHODS FOR MODULATING APOPTOSIS

(75) Inventors: Orest W. Blaschuk, Westmount (CA); Barbara J. Gour, Kemptville (CA)

(73) Assignee: McGill University, Montreal (CA)

(*) Notice: Subject to any disclaimer, the term of this patent is extended or adjusted under 35 U.S.C. 154(b) by 475 days.

This patent is subject to a terminal disclaimer.

(21) Appl. No.: 10/359,546

(22) Filed: Feb. 4, 2003

(65) Prior Publication Data

US 2003/0224978 A1    Dec. 4, 2003

Related U.S. Application Data

(63) Continuation of application No. 09/248,015, filed on Feb. 10, 1999, now Pat. No. 6,562,786, which is a continuation-in-part of application No. 08/996,679, filed on Dec. 23, 1997, now Pat. No. 6,169,071, which is a continuation-in-part of application No. 08/893,534, filed on Jul. 11, 1997, now Pat. No. 6,031,072.

(60) Provisional application No. 60/021,612, filed on Jul. 12, 1996.

(51) Int. Cl.
*A61K 38/12* (2006.01)
*C07K 7/64* (2006.01)

(52) U.S. Cl. .............. 514/1; 514/14; 514/15; 514/16; 530/317

(58) Field of Classification Search ............ None
See application file for complete search history.

(56) References Cited

U.S. PATENT DOCUMENTS

| | | | | |
|---|---|---|---|---|
| 5,231,082 | A | 7/1993 | Schasteen | 514/11 |
| 5,352,667 | A | 10/1994 | Lider et al. | 514/19 |
| 5,510,628 | A | 4/1996 | Georger, Jr. et al. | 257/32 |
| 5,585,351 | A * | 12/1996 | Ranscht | 514/12 |
| 5,591,432 | A | 1/1997 | Bronson et al. | 424/130.1 |
| 5,646,250 | A | 7/1997 | Suzuki | 530/350 |
| 5,665,590 | A | 9/1997 | Yang | 435/6 |
| 6,417,325 | B1 * | 7/2002 | Blaschuk et al. | 530/317 |
| 6,465,427 | B1 * | 10/2002 | Blaschuk et al. | 514/9 |
| 6,562,786 | B1 * | 5/2003 | Blaschuk et al. | 514/11 |
| 6,780,845 | B1 * | 8/2004 | Blaschuk et al. | 514/9 |

FOREIGN PATENT DOCUMENTS

| | | |
|---|---|---|
| EP | 406 428 B1 | 1/1991 |
| WO | WO 91/04745 | 4/1991 |
| WO | WO 92/08731 | 5/1992 |

(Continued)

OTHER PUBLICATIONS

Ngo et al. "Computational Complexity, Protein Structure Prediction, and the Levinthal Paradox." The Protein Folding Problem and Tertiary structure Prediction. Ed. K. Merz and L. Le Grand. Birkhauser, Boston, Ma. 491-495.*

(Continued)

*Primary Examiner*—Anish Gupta
(74) *Attorney, Agent, or Firm*—Seed IP Law Group PLLC

(57) ABSTRACT

Cyclic peptides and compositions comprising such cyclic peptides are provided. The cyclic peptides comprise a classical cadherin cell adhesion recognition sequence HAV. Methods for using such peptides and compositions for inducing apoptosis in cadherin-expressing cells, such as cancer cells, are also provided.

29 Claims, 36 Drawing Sheets

FOREIGN PATENT DOCUMENTS

| WO | WO 94/11401 | 5/1994 |
|---|---|---|
| WO | WO 96/40781 | 12/1996 |
| WO | WO 97/07209 | 2/1997 |
| WO | WO 98/02452 | 1/1998 |
| WO | WO 98/45319 | 10/1998 |
| WO | WO 99/33875 | 7/1999 |
| WO | WO 01/53331 | 7/2001 |

OTHER PUBLICATIONS

Rudinger, J. (1976). Peptide Hormones (Ed. J.A. Parson). University Park Press. Baltimore pp. 1-7.*

Berendsen, Herman. "A Glimpse of the Holy Grail?" *Science*, vol. 282, pp. 642-643. Oct. 23, 1998.*

Alexander et al., "An N-Cadherin-Like Protein Contributes to Solute Barrier Maintenance in Cultured Endothelium," *Journal of Cellular Physiology* 156:610-618, 1993.

Ali et al., "Conformationally Constrained Peptides and Semipeptides Derived from RGD as Potent Inhibitors of the Platelet Fibrinogen Receptor and Platelet Aggregation," *J. Med. Chem.* 37(6): 769-780, 1994.

Beesley et al., "The post-synaptic density: putative involvement in synapse stabilization via cahderins and covalent modification by ubiquitination," *Biochemical Society Transactions* 23:59-64, 1995.

Blakemore, "Remyelination of CNS axons by Schwann cells transplanted from the sciatic nerve," *Nature* 266: 68-69, 1977.

Blaschuk and Farookhi, "Estradiol Stimulates Cadherin Expression in Rat Granulosa Cells," *Developmental Biology* 136: 564-567, 1989.

Blaschuk et al., "A novel cadherin antagonist (Exherin) blocks human ovarian tumor growth in nude mice," *Molecular Biology of the Cell* 10: 72A, Nov. 1999.

Blaschuk et al., "E-Cadherin, estrogens and cancer: is there a connection?" *The Canadian Journal of Oncology* 4(4): 291-301, 1994.

Blaschuk et al., "Identification of a Cadherin Cell Adhesion Recognition Sequence," *Developmental Biology* 139: 227-229, 1990.

Blaschuk et al., "Identification of a Conserved Region Common to Cadherins and Influenza Strain A Hemagglutinins," *J. Mol. Biol.* 211: 679-682, 1990.

Bottenstein and Sato, "Growth of a rat neuroblastoma cell line in serum-free supplemented medium," *Proc.Natl. Acad. Sci. USA* 76(1): 514-517, 1979.

Brecknell et al., "Bridge grafts of Fibroblast Growth Factor-4-Secreting Schwannoma Cells Promote Functional Axonal Regeneration in the Nigrostriatal Pathway of the Adult Rat," *Neuroscience* 74(3): 775-784, 1996.

Brockes et al., "Studies on Cultured Rat Schwann Cells. I. Establishment of Purified Populations from Cultures of Peripheral Nerve," *Brain Research* 165: 105-118, 1979.

Brook et al., "Morphology and Migration of Cultured Schwann Cells Transplanted Into the Fimbria and Hippocampus in Adult Rats," *GLIA* 9: 292-304, 1993.

Byers et al., "Fibroblast Growth Factor Receptors Contain a Conserved HAV Region Common to Cadherins and Influenza Strain A Hemagglutinins: A Role in Protein-Protein Interactions?," *Developmental Biology* 152: 411-414, 1992.

Cardarelli et al., "The Collagen Receptor α2β1, from MG-63 and HT1080 Cells, Interacts with a Cyclic RGD Peptide," *The Journal of Biological Chemistry* 267(32): 23159-23164, 1992.

Carlstedt et al., "Nerve Fibre Regeneration Across the PNS-CNS Interface at the Root-Spinal Cord Junction," *Brain Research Bulletin* 22: 93-102, 1989.

Cepek et al., "Expression of a candidate cadherin in T lymphocytes," *Proc. Natl. Acad. Sci. USA* 93: 6567-6571, 1996.

Chuah et al., "Differentiation and survival of rat olfactory epithelial neurons in dissociated cell culture," *Developmental Brain Research* 60: 123-132, 1991.

Craig et al., "Concept and Progress in the Development of RGD-Containing Peptide Pharmaceuticals," *Biopolymers (Peptide Science)* 37:157-175, 1995.

Doherty and Walsh, "CAM-FGF Receptor Interactions: A Model for Axonal Growth," *Molecular and Cellular Neuroscience* 8(Article No. 0049): 99-111, 1996.

Doherty and Walsh, "Signal transduction events underlying neurite outgrowth stimulated by cell adhesion molecules," *Current Opinion in Neurobiology* 4: 49-55, 1994.

Doherty et al., "Neurite Outgrowth in Response to Transfected N-CAM and N-Cadherin Reveals Fundamental Differences in Neuronal Responsiveness to CAMS," *Neuron* 6: 247-258, 1991.

Duncan et al., "Transplantation of oligodendrocytes and Schwann cells into the spinal cord of the myelin-deficient rat," *Journal of Neurocytology* 17: 351-360, 1988.

Fok-Seang et al., "An analysis of astrocytic cell lines with different abilities to promote axon growth," *Brain Research* 689: 207-223, 1995.

Fok-Seang et al., "Migration of Oligodendrocyte Precursors on Astrocytes and Meningeal Cells," *Developmental Biology* 171: 1-15, 1995.

Franz, "Percutaneous Absorption. On The Relevance Of In Vitro Data," *The Journal of Investigative Dermatology* 64(3): 190-195, 1975.

Franz, "The Finite Dose Technique as a Valid *in Vitro* Model for the Study of Percutaneous Absorption in Man," *Curr. Probl. Dermatol.* 7: 58-68, 1978.

Ghirnikar and Eng, "Astrocyte-Schwann Cell Interactions in Culture," *GLIA* 11: 367-377, 1994.

Gumbiner et al., "The Role of the Cell Adhesion Molecule Uvomorulin in the Formation and Maintenance of the Epithelial Junctional Complex," *The Journal of Cell Biology* 107: 1575-1587, 1988.

Iruela-Arispe et al., "Expression of SPARC during Development of the Chicken Chorioallantoic Membrane: Evidence for Regulated Proteolysis In Vivo," *Molecular Biology of the Cell* 6: 327-343, 1995.

Laird et al., "Gap Junction Turnover, Intracellular Trafficking, and Phosphorylation of Connexin43 in Brefeldin A-treated Rat Mammary Tumor Cells," *The Journal of Cell Biology* 131(5): 1193-1203, 1995.

Lee et al., "Expression of the Homotypic Adhesion Molecule E-Cadherin by Immature Murine Thymocytes and Thymic Epithelial Cells," *Journal of Immunology* 152: 5653-5659, 1994.

Letourneau et al., "Interactions of Schwann Cells with Neurites and with Other Schwann Cells Involve the Calcium-dependent Adhesion Molecule, N-cadherin," *Journal of Neurobiology* 22(7): 707-720, 1991.

Liuzzi and Lasek, "Astrocytes Block Axonal Regeneration in Mammals by Activating the Physiological Stop Pathway," *Science* 237: 642-645, 1987.

Lutz et al., "Secondary Structure of the HAV Peptide Which Regulates Cadherin-Cadherin Interaction," *Journal of Biomolecular Structure & Dynamics* 13(3): 447-455, 1995.

Matsuzaki et al., "cDNAs of Cell Adhesion Molecules of Different Specificity Induce Changes in Cell Shape and Border Formation in Cultured S180 Cells," *The Journal of Cell Biology* 110: 1239-1252, 1990.

McCarthy and Vellis, "Preparation of Separate Astroglial and Oligodendroglial Cell Cultures from Rat Cerebral Tissue," *J. Cell Biology* 85: 890-902, 1980.

Mege et al., "Construction of epithelioid sheets by transfection of mouse sarcoma cells with cDNAs for chicken cell adhesion molecules," *Proc. Natl. Acad. Sci. USA* 85: 7274-7278, 1988.

Moran, "The Protein Delivery Service. Advances in technologies for delivering proteins and peptides in therapeutically useful forms," *Pharmaceutical Forum Issue* 6: 4-7, 1996.

Munro and Blaschuk, *Cell Adhesion and Invasion in Cancer Metastasis*, R.G. Landes Company, Austin, TX, 1996, Chapter 3, "The Structure, Function and Regulation of Cadherins," pp. 17-34.

Munro et al., "Characterization of Cadherins Expressed by Murine Thymocytes," *Cellular Immunology* 169(Article No. 0123): 309-312, 1996.

Newton et al., "N-Cadherin Mediates Sertoli Cell-Spermatogenic Cell Adhesion," *Developmental Dynamics* 197: 1-13, 1993.

Nose et al., "Localization of Specificity Determining Sites in Cadherin Cell Adhesion Molecules," *Cell 61*; 147-155, 1990.

Orr, "Angiogenesis Research Offers New Approaches to Treatment of Disease," *Genetic Engineering News*, pp. 15-16, 42, May 1, 1996.

Overduin et al., "Solution Structure of the Epithelial Cadherin Domain Responsible for Selective Cell Adhesion," *Science 267*: 386-389, 1995.

Redies and Takeichi, "Cadherins in the Developing Central Nervous System: An Adhesive Code for Segmental and Functional Subdivisions," *Developmental Biology 180*: 413-423, 1996.

Saffell et al., "Expression of a Dominant Negative FGF Receptor Inhibits Axonal Growth and FGF Receptor Phosphorylation Stimulated by CAMs," *Neuron*, pp. 231-242, Feb. 1997.

Samanen et al., "Development of a Small RGD Peptide Fibrinogen Receptor Antagonist with Potent Antiaggregatory Activity in Vitro," *J. Med. Chem. 34*(10): 3114-3125, 1991.

Shapiro et al., "Structural basis of cell-cell adhesion by cadherins," *Nature 374*: 327-337, 1995.

Starzinsky-Powitz, E.A., "The putative role of cell adhesion molecules in endometrisis: can we learn from tumour metastasis?," *Mol. Med. Today 5*(7): 304-309, 1999.

Tsutsui et al., "Expression of Cadherin-Catenin Complexes in Human Leukemia Cell Lines," *J. Biochem. 120*: 1034-1039, 1996.

Wickelgren, "Breaking the Skin Barrier," *PS 12*: 86-88, 1996.

Willems et al., "Cadherin-dependent cell aggregation is affected by decapeptide derived from rat extracellular super-oxide dismutase," *FEBS Letters 363*: 289-292, 1995.

Williams et al., "Activation of the FGF Receptor Underlies Neurite Outgrowth Stimulated by L1, N-CAM, and N-Cadherin," *Neuron 13*: 583-594, 1994.

Williams et al., "The Priamary Structure of Hen Ovotransferrin," *Eur. J. Biochem. 122*: 297-303, 1982.

Williams, E.A., "A novel family of cyclic peptide antagonists suggests that N-cadherin specificity is determined by amino acids that flank the HAV motif," *J. Biol. Chem. 275*(6): 4007-4012, Feb. 11, 2000.

Blaschuk and Gour, "Compounds and Methods for Modulating Cell Adhesion" U.S. Appl. No. 10/006,982, filed Dec. 4, 2001.

Blaschuk et al, "Compounds and Methods for Cancer Therapy," U.S. Appl. No. 10/058,821, filed Jan. 29, 2002.

Gour et al., "Peptidomimetic Modulators of Cell Adhesion," U.S. Appl. No. 10/425,557, filed Apr. 28, 2003.

Blaschuk et al., "Compounds and Methods for Modulating Cell Adhesion," U.S. Appl. No. 10/105,008, filed Mar. 22, 2002.

Blaschuk and Gour, "Compounds and Methods for Regulating Cell Adhesion," U.S. Appl. No. 09/778,026, filed Feb. 5, 2001.

Doherty et al., "Compounds and Methods for Modulating Adhesion Molecule Function," U.S. Appl. No. 10/193,653, filed Jul. 10, 2002.

Gour et al., "Peptidomimetic Modulators of Cell Adhesion," U.S. Appl. No. 10/412,701, filed Apr. 9, 2003.

Blaschuk et al., "Methods for Diagnosing and Evaluating Cancer," U.S. Appl. No. 09/305,928, filed May 5, 1999.

\* cited by examiner

| | |
|---|---|
| human N-cad | DWVIPPINLPENSRGPFPQELVRIRSDRDKNLSLRIRVTGPGADQPPTGIFIINPISGQLSVTKPLDRQQ |
| mouse N-cad | DWVIPPINLPENSRGPFPQELVRIRSDRDKNLSLRIRVTGPGADQPPTGIFIINPISGQLSVTKPLDREL |
| cow N-cad | DWVIPPINLPENSRGPFPQELVRIRSDRDKNLSLRYSVTGPGADQPPTGIFIINPISGQLSVTKPLDREL |
| human P-cad | DWVIPPINLPENSRGPFPQELVRIRSDRDKNLSLRYSVTGPGADQPPTGIFIINPISGQLSVTKPLDREL |
| mouse P-cad | DWVAPISVPENGKGPFPQRLNQLKSNKDRDTKIFYSITGPGADSPPEGVFAVEKETGWILLNKPLDREE |
| human E-cad | EWVMPPIFVPENGKGPFPQRLNQLKSNKDRGTKIFYSITGPGADSPPEGVFTIEKESGWLLLHMPLDREK |
| mouse E-cad | DWVIPPISCPENEKGPFPKNLVQIKSNKDKEGKVFYSITGQGADTPPVGVFIIERETGWLKVTEPLDRER |
| | DWVIPPISCPENEKGEFPKNLVQIKSNRDKETKVFYSITGQGADKPPVGVFIIERETGWLKVTQPLDREA |

| | |
|---|---|
| human N-cad | NARFHLGAHAVDINGNQVETPIDIVINVIDMNDNRPEF |
| mouse N-cad | IARFHLRAHAVDINGNQVENPIDIVINVIDMNDNRPEF |
| cow N-cad | IARFHLRAHAVDINGNQVENPIDIVINVIDMNDNRPEF |
| human P-cad | IAKYELFGHAVSENGASVEDPMNISIIVTDQNDHKPKF |
| mouse P-cad | IVKYELYGHAVSENGASVEEPMNISIIVTDQNDNKPKF |
| human E-cad | IATYTLFSHAVSSNGNAVEDPMEILITVTDQNDNKPEF |
| mouse E-cad | IAKYILYSHAVSSNGEAVEDPMEIVITVTDQNDNRPEF |

Fig. 2

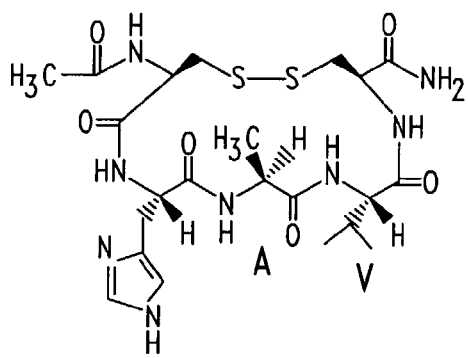
N-Ac-CHAVC-NH₂
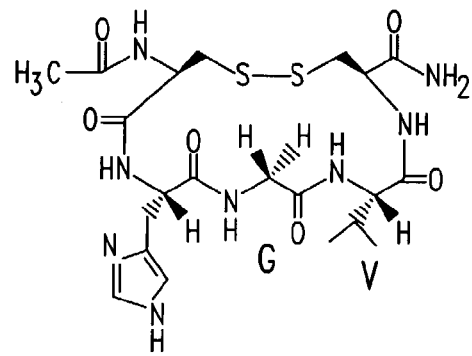
N-Ac-CHGVC-NH₂
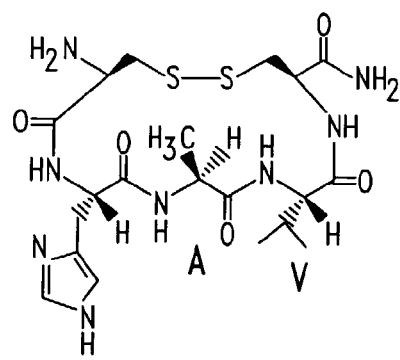
H-CHAVC-NH₂
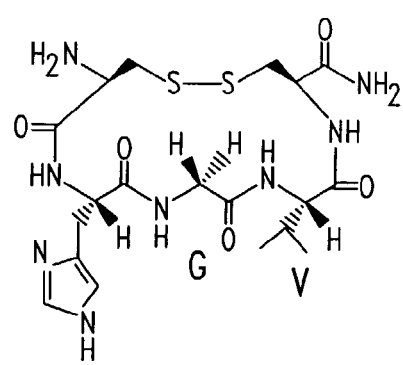
H-CHGVC-NH₂
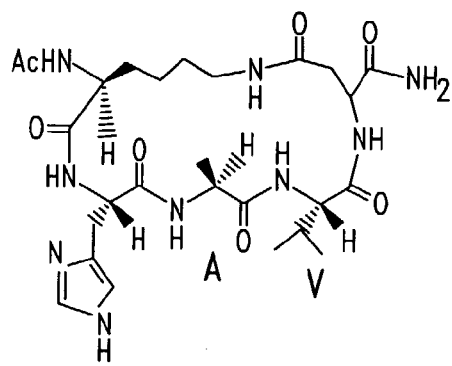
N-Ac-KHAVD-NH₂
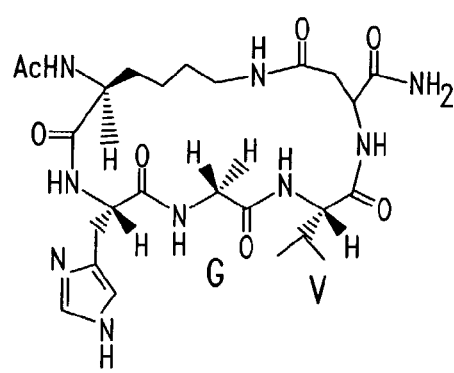
N-Ac-KHGVD-NH₂
*Fig. 3A*

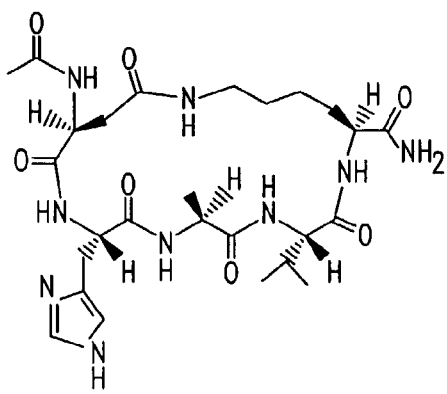
N-Ac-DHAVK-NH₂
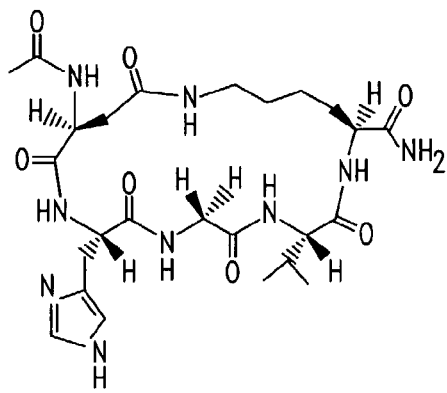
N-Ac-DHGVK-NH₂
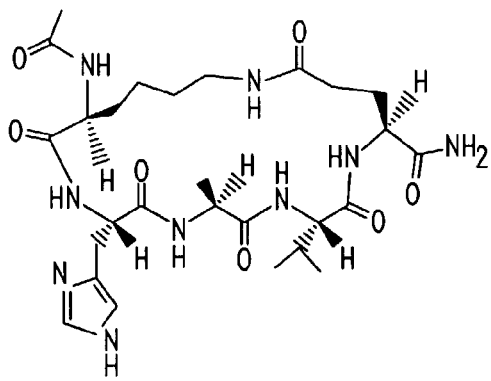
N-Ac-KHAVE-NH₂
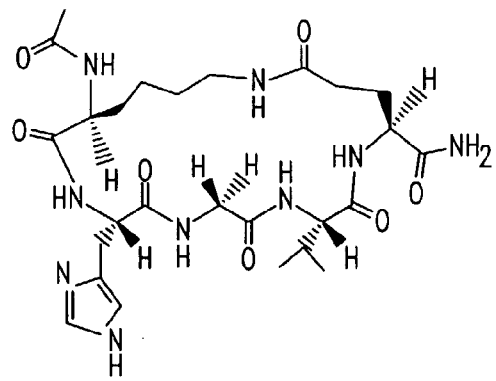
N-Ac-KHGVE-NH₂
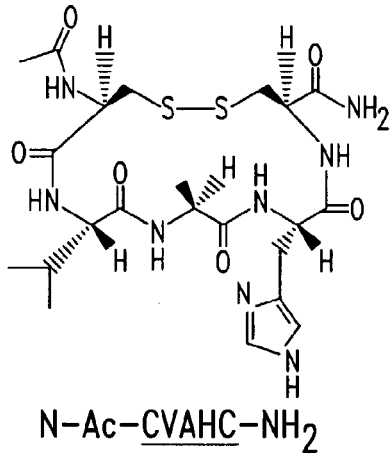
N-Ac-CVAHC-NH₂
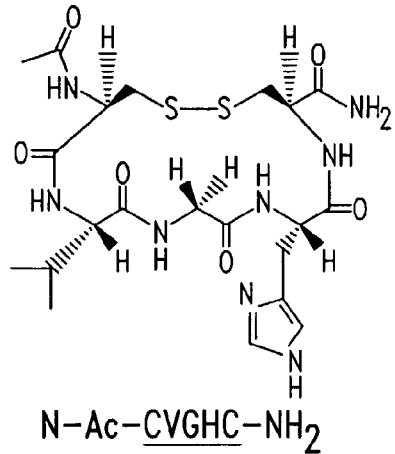
N-Ac-CVGHC-NH₂
*Fig. 3B*

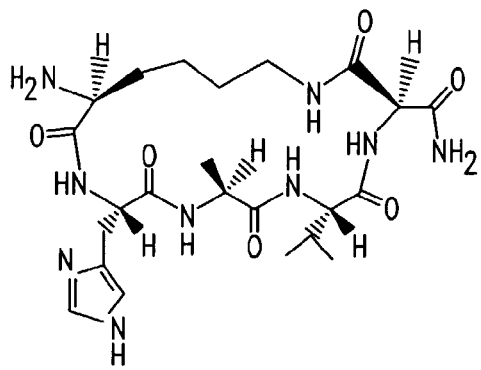
H-KHAVD-NH₂
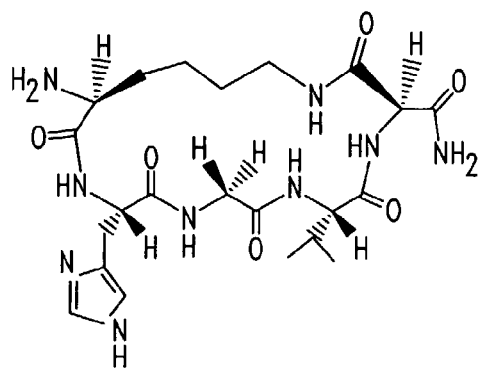
H-KHGVD-NH₂
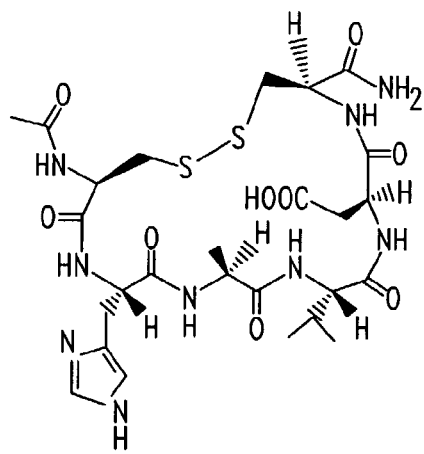
N-Ac-CHAVDC-NH₂
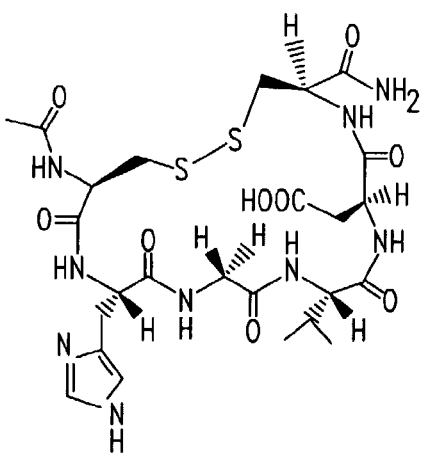
N-Ac-CHGVDC-NH₂
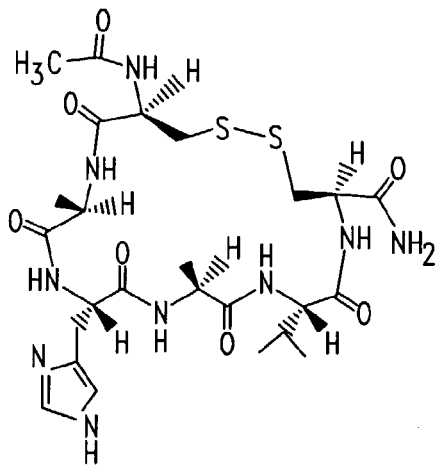
N-Ac-CAHAVC-NH₂
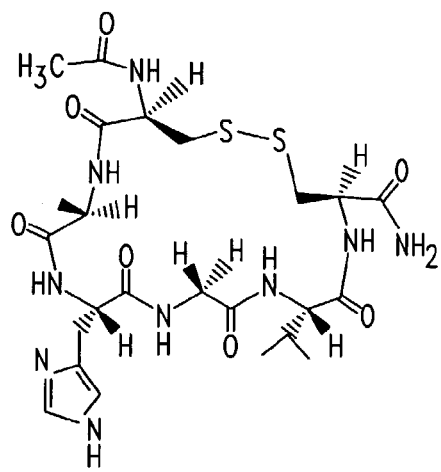
N-Ac-CAHGVC-NH₂
*Fig. 3C*

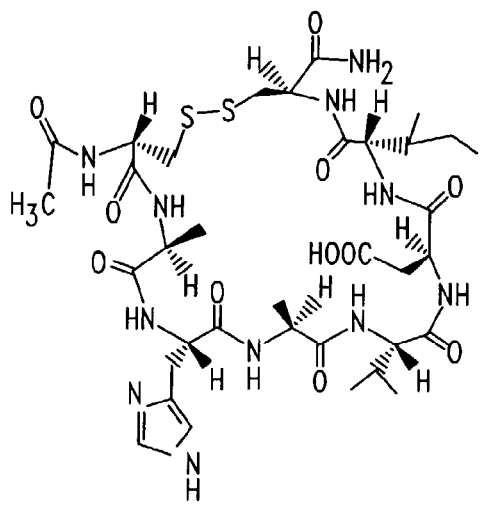
N-Ac-CAHAVDIC-NH2
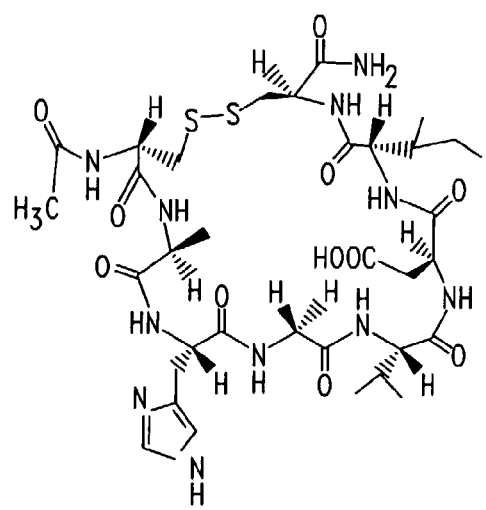
N-Ac-CAHGVDIC-NH2
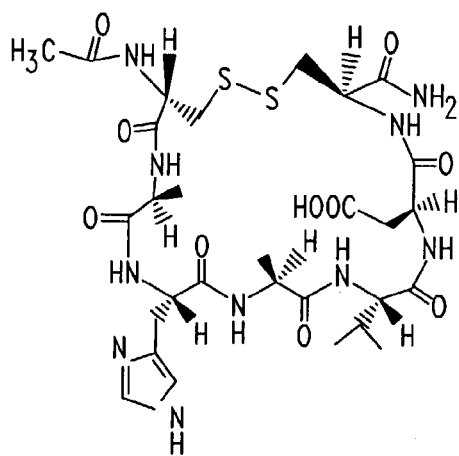
N-Ac-CAHAVDC-NH2
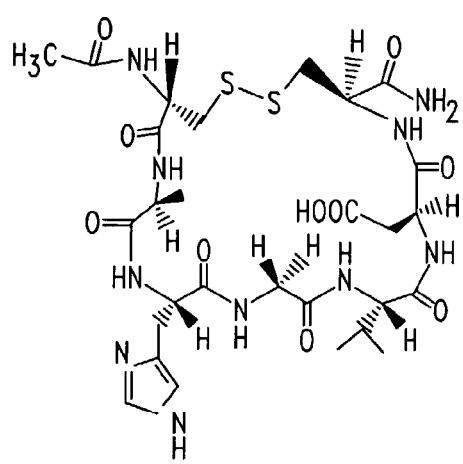
N-Ac-CAHGVDC-NH2
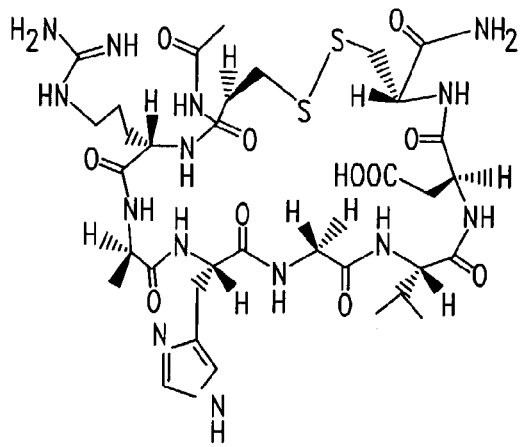
N-Ac-CRAHAVDC-NH2
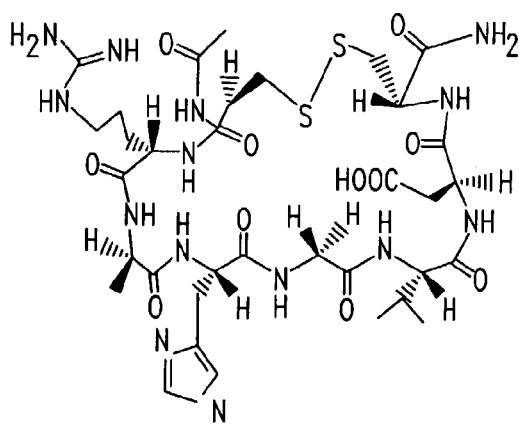
N-Ac-CRAHGVDC-NH2
*Fig. 3D*

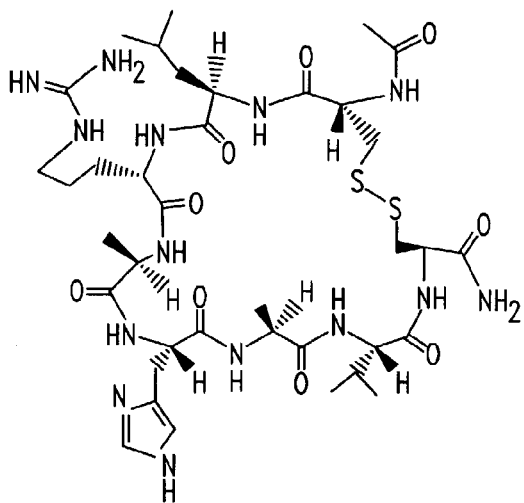
N-Ac-CLRAHAVC-NH2
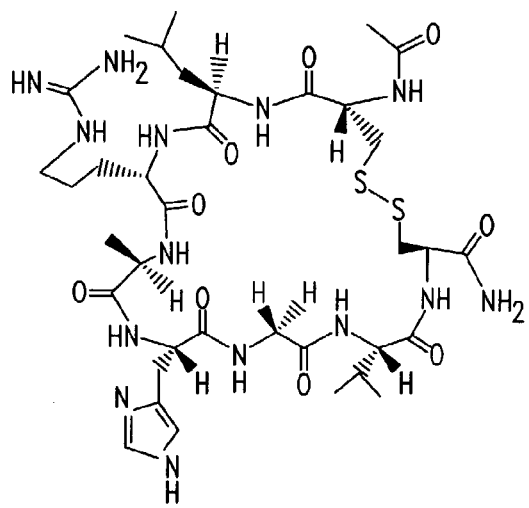
N-Ac-CLRAHGVC-NH2
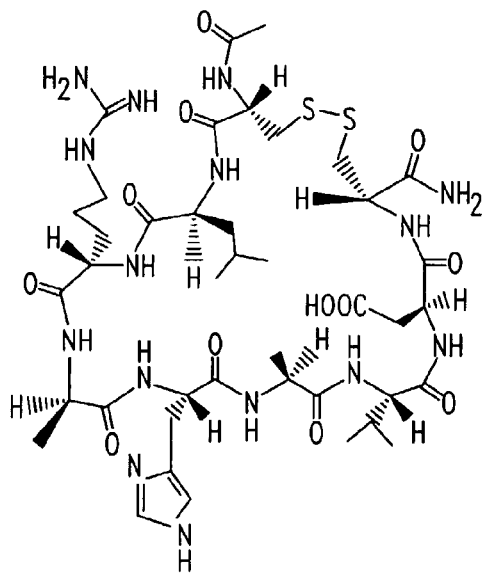
N-Ac-CLRAHAVDC-NH2
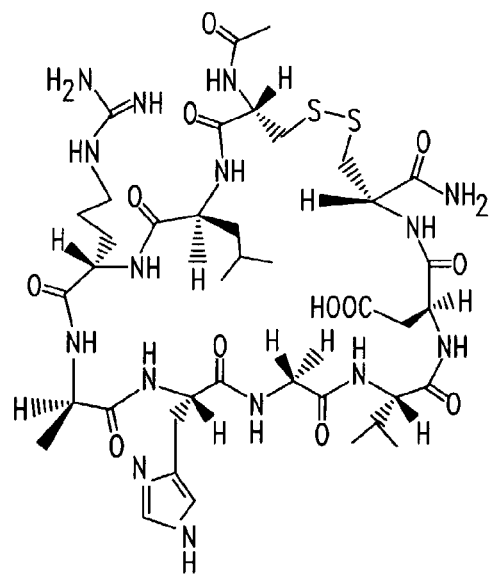
N-Ac-CLRAHGVDC-NH2
*Fig. 3E*

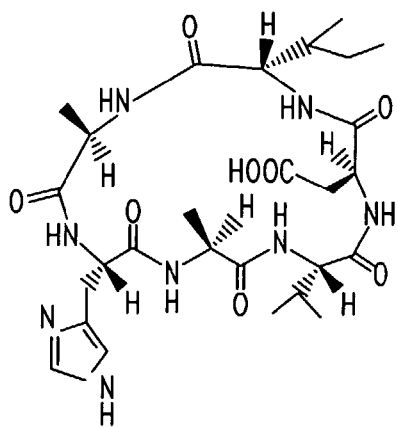
AHAVDI
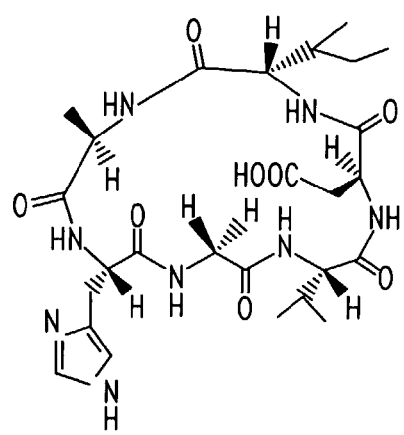
AHGVDI
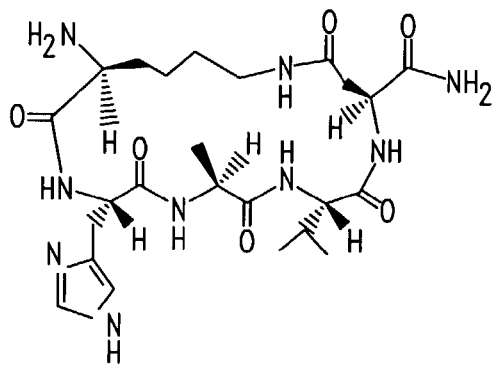
H-KHAVD-NH₂
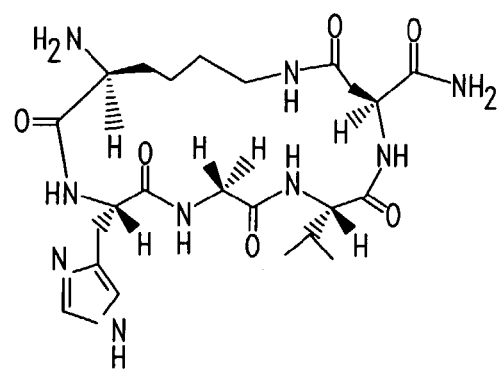
H-KHGVD-NH₂
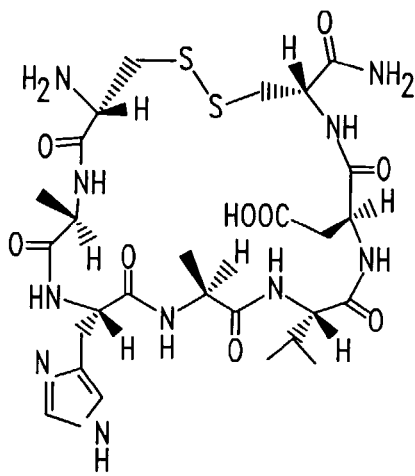
H-CAHAVDC-NH₂
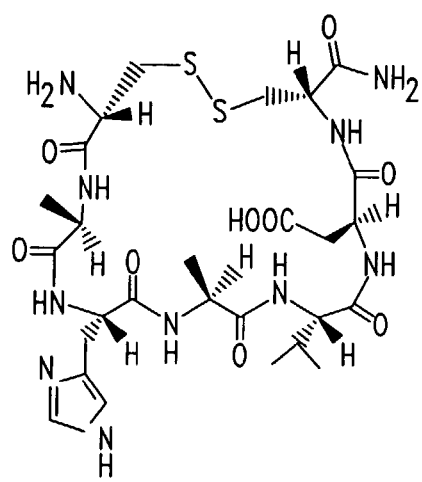
H-CAHGVDC-NH₂
Fig. 3F

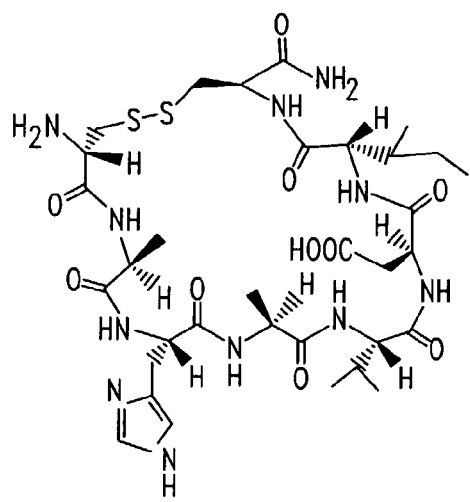
H-CAHAVDIC-NH2
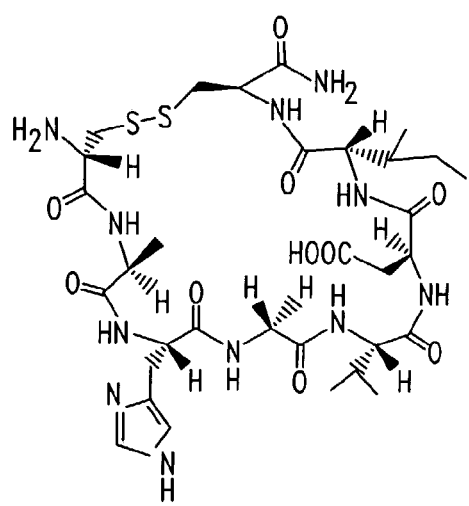
H-CAHGVDIC-NH2
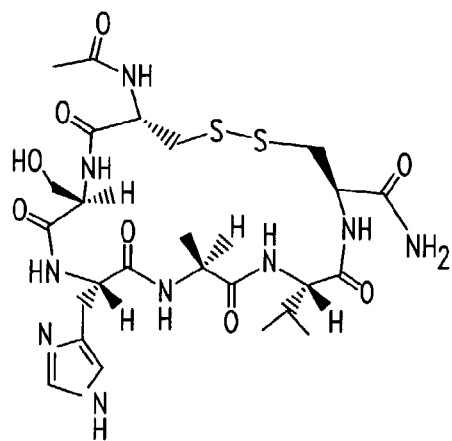
N-Ac-CSHAVC-NH2
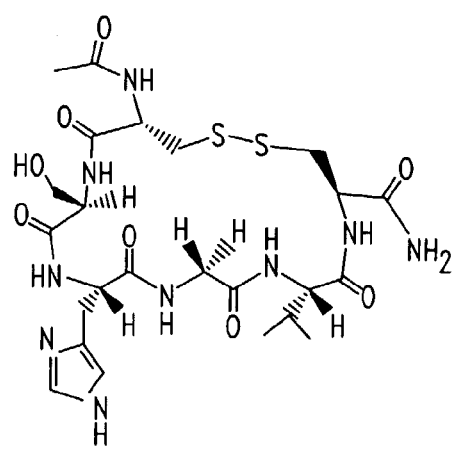
N-Ac-CSHGVC-NH2
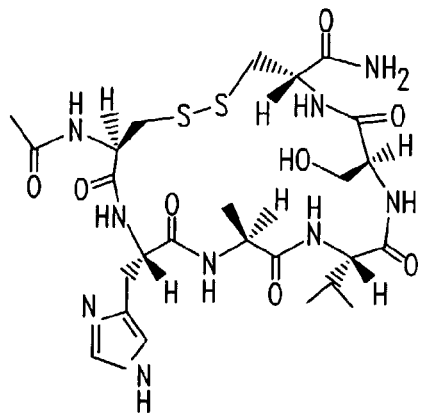
N-Ac-CHAVSC-NH2
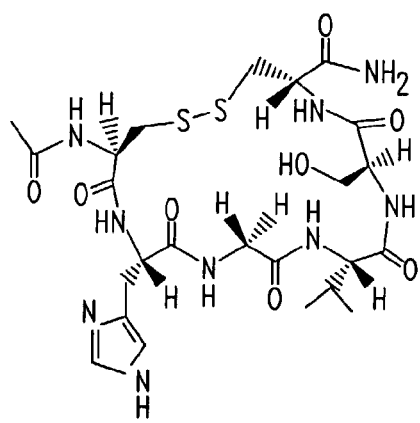
N-Ac-CHGVSC-NH2
*Fig. 3G*

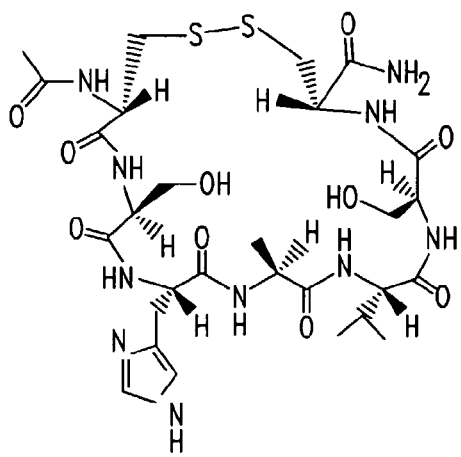
N-Ac-CSHAVSC-NH₂
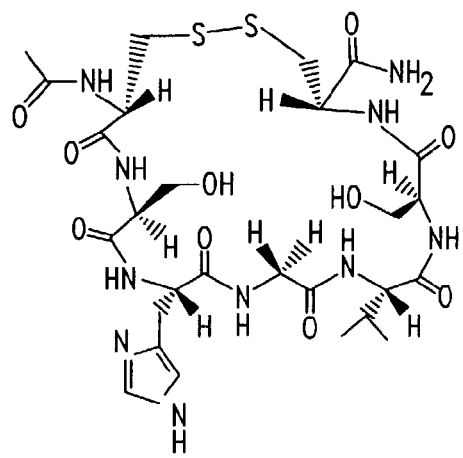
N-Ac-CSHGVSC-NH₂
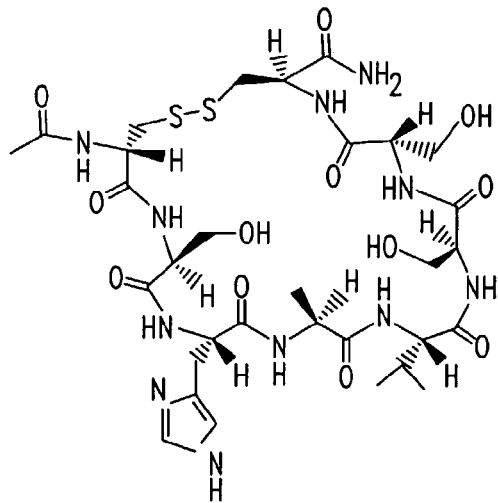
N-Ac-CSHAVSSC-NH₂
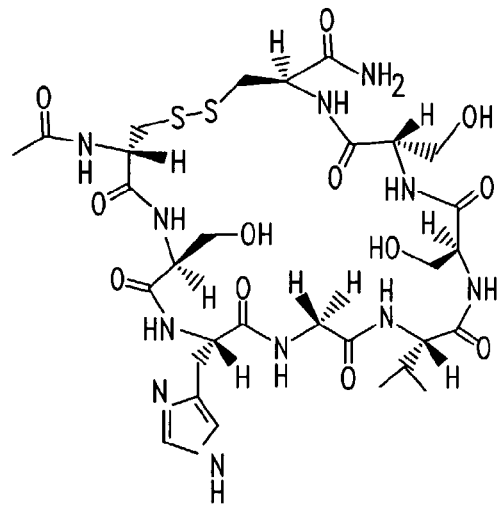
N-Ac-CSHGVSSC-NH₂
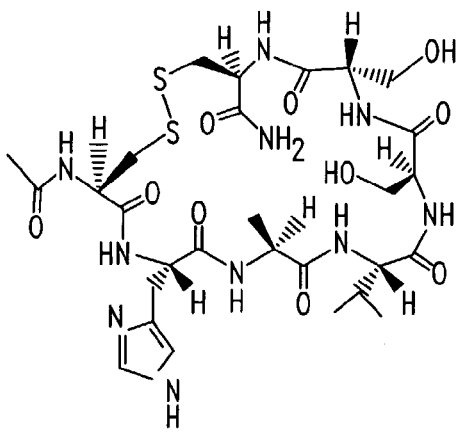
N-Ac-CHAVSSC-NH₂
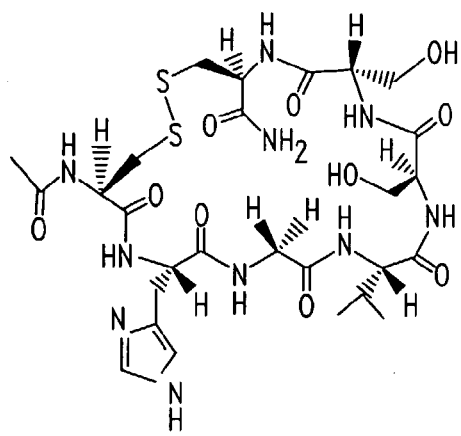
N-Ac-CHGVSSC-NH₂
*Fig. 3H*

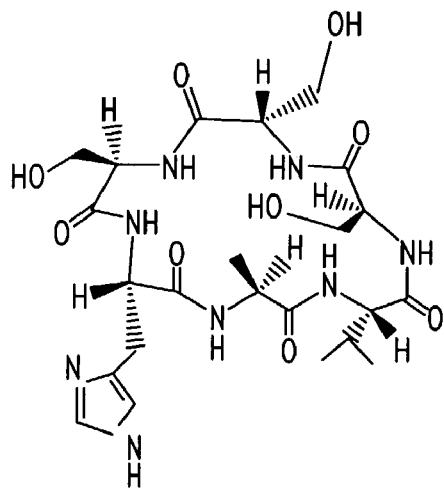
SHAVSS
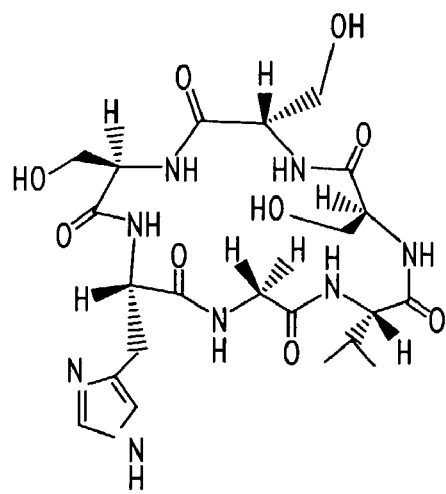
SHGVSS
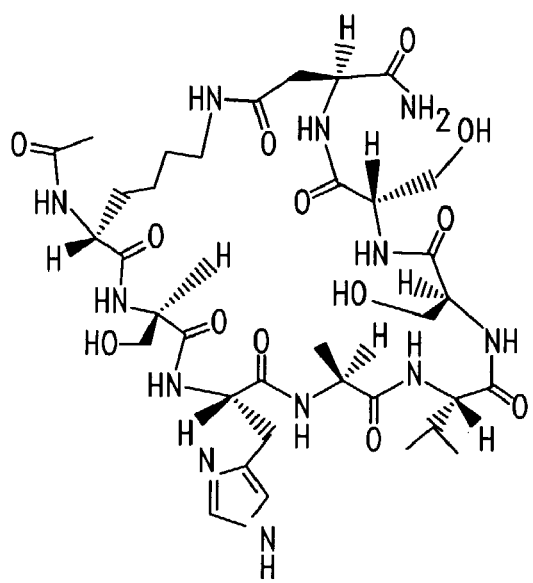
N-Ac-KSHAVSSD-NH$_2$
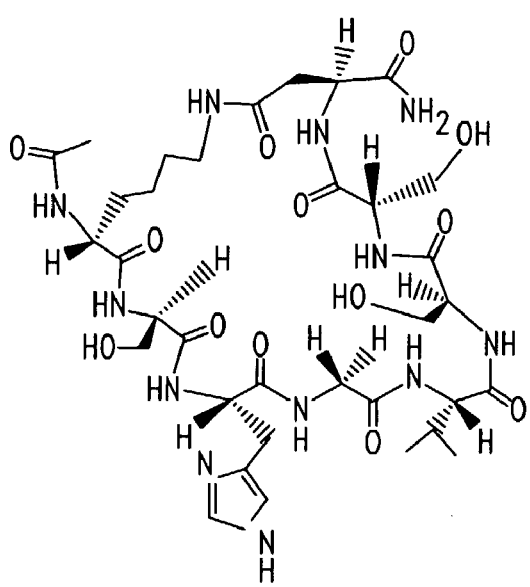
N-Ac-KSHGVSSD-NH$_2$
*Fig. 3I*

COMPOUNDS AND METHODS FOR MODULATING APOPTOSIS

CROSS-REFERENCE TO RELATED APPLICATIONS

This application is a continuation of U.S. Ser. No. 09/248,015, filed Feb. 10, 1999, now U.S. Pat. No. 6,562,786, which is a continuation-in-part of U.S. Ser. No. 08/996,679, filed Dec. 23, 1997, now U.S. Pat. No. 6,169,071, which is a continuation-in-part of U.S. Ser. No. 08/893,534, filed Jul. 11, 1997, now U.S. Pat. No. 6,031,072, which claims the benefit of U.S. Provisional Application No. 60/021,612, filed on Jul. 12, 1996.

TECHNICAL FIELD

The present invention relates generally to methods for methods for modulating cadherin mediated processes, and more particularly to the use of cyclic peptides comprising a classical cadherin cell adhesion recognition sequence for inducing apoptosis in cadherin-expressing cells.

BACKGROUND OF THE INVENTION

Cancer is a significant health problem throughout the world. Although advances have been made in detection and therapy of cancer, no vaccine or other universally successful method for prevention or treatment is currently available. For example, among women, breast and ovarian cancer are prevalent in the United States and other countries. Breast cancer, in particular, remains the second leading cause of cancer-related deaths in women, affecting more than 180,000 women in the United States each year. For women in North America, the life-time odds of getting breast cancer are now one in eight. Management of the disease currently relies on a combination of early diagnosis (through routine breast screening procedures) and aggressive treatment, which may include one or more of a variety of treatments such as surgery, radiotherapy, chemotherapy and hormone therapy.

Prostate cancer is the most common form of cancer among males, with an estimated incidence of 30% in men over the age of 50. Human prostate cancer has the propensity to metastasize to bone. Treatment is commonly based on surgery and/or radiation therapy, but these methods are ineffective in a significant percentage of cases, and this prevalent disease is currently the second leading cause of cancer death among men in the U.S.

To provide improved treatments for such diseases, agents that kill cancer cells are needed. Accordingly, there is a need in the art for compounds that induce apoptosis in cancer cells. The present invention fulfills this need and further provides other related advantages.

SUMMARY OF THE INVENTION

The present invention provides cyclic peptides and methods for modulating cadherin-mediated functions and inducing apoptosis in cadherin-expressing cells. Within one aspect, the present invention provides cyclic peptides comprising the sequence His-Ala-Val. Within one embodiment a cyclic peptide has the formula:

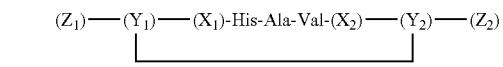

wherein $X_1$, and $X_2$ are optional, and if present, are independently selected from the group consisting of amino acid residues and combinations thereof in which the residues are linked by peptide bonds, and wherein $X_1$ and $X_2$ independently range in size from 0 to 10 residues, such that the sum of residues contained within $X_1$ and $X_2$ ranges from 1 to 12; wherein $Y_1$ and $Y_2$ are independently selected from the group consisting of amino acid residues, and wherein a covalent bond is formed between residues $Y_1$ and $Y_2$; and wherein $Z_1$ and $Z_2$ are optional, and if present, are independently selected from the group consisting of amino acid residues and combinations thereof in which the residues are linked by peptide bonds. Such cyclic peptides may comprise modifications such as an N-acetyl or N-alkoxybenzyl group and/or a C-terminal amide or ester group. Cyclic peptides may be cyclized via, for example, a disulfide bond; an amide bond between terminal functional groups, between residue side-chains or between one terminal functional group and one residue side chain; a thioether bond or $\delta_1\delta_1$-ditryptophan, or a derivative thereof.

Within further aspects, the present invention provides modulating agents that comprise a cyclic peptide as described above. Within specific embodiments, such modulating agents may be linked to one or more of a targeting agent, a drug, a solid support or a support molecule. In addition, or alternatively, a cell adhesion modulating agent may further comprising one or more of: (a) a cell adhesion recognition sequence that is bound by an adhesion molecule other than a cadherin, wherein said cell adhesion recognition sequence is separated from any HAV sequence(s) by a linker; and/or (b) an antibody or antigen-binding fragment thereof that specifically binds to a cell adhesion recognition sequence bound by an adhesion molecule other than a cadherin.

The present invention further provides pharmaceutical compositions comprising a cell adhesion modulating agent as described above, in combination with a pharmaceutically acceptable carrier. Such compositions may further comprise a drug. Alternatively, or in addition, such compositions may comprise: (a) a modulator of cell adhesion comprising a cell adhesion recognition sequence that is bound by an adhesion molecule other than a classical cadherin; and/or (b) an antibody or antigen-binding fragment thereof that specifically binds to a cell adhesion recognition sequence bound by an adhesion molecule other than a classical cadherin.

Within further aspects, methods are provided for inducing apoptosis in a cadherin-expressing cell, comprising contacting a cadherin-expressing cell with a cell adhesion modulating agent as described above. Within certain embodiments, the cadherin-expressing cell may be a cancer cell, and such cells may be present in a patient.

These and other aspects of the invention will become evident upon reference to the following detailed description and attached drawings. All references disclosed herein are hereby incorporated by reference in their entirety as if each were individually noted for incorporation.

BRIEF DESCRIPTION OF THE DRAWINGS

FIG. 2 provides the amino acid sequences of mammalian classical cadherin EC1 domains: human N-cadherin (SEQ ID NO:1), mouse N-cadherin (SEQ ID NO:2), cow N-cadherin (SEQ ID NO:3), human P-cadherin (SEQ ID NO:4), mouse P-cadherin (SEQ ID NO:5), human E-cadherin (SEQ ID NO:6) and mouse E-cadherin (SEQ ID NO:7).

FIGS. 3A–3I provides the structures of representative cyclic peptides of the present invention (SEQ ID NOs: 10–19, 26–28, 34, 37, 43, 49, 52, 54, 60; structures on the left hand side), along with similar, but inactive, on the right structures (SEQ ID NOs: 20, 38–42, 44–48, 50, 51, 53, 55–59, 61).

FIG. 7A shows the cells 30 minutes after exposure to 500 μg/mL N-Ac-CHAVC-NH$_2$ (SEQ ID NO:10). FIG. 7B shows the cells 30 minutes after exposure to the control peptide N-Ac-CHGVC-NH$_2$ (SEQ ID NO:20). FIG. 7C shows the cells in the absence of cyclic peptide. Note that the endothelial cells retracted from one another in the presence of N-Ac-CHAVC-NH$_2$ (SEQ ID NO:10).

FIG. 8A shows the cells 30 minutes after exposure to 500 μg/mL N-Ac-CAHAVDIC-NH$_2$ (SEQ ID NO:14). FIG. 8B shows the cells 30 minutes after exposure to the control peptide N-Ac-CAHGVDIC-NH$_2$ (SEQ ID NO:41). FIG. 8C shows the cells in the absence of cyclic peptide. In this case, neither of the cyclic peptides show activity.

FIG. 9A shows the cells 30 minutes after exposure to 500 μg/mL N-Ac-CAHAVDC-NH$_2$ (SEQ ID NO:13). FIG. 9B shows the cells 30 minutes after exposure to the control peptide N-Ac-CAHGVDC-NH$_2$ (SEQ ID NO:46). FIG. 9C shows the cells in the absence of cyclic peptide. Note that the endothelial cells retracted from one another in the presence of N-Ac-CAHAVDC-NH$_2$ (SEQ ID NO:13).

FIG. 10A shows the cells 30 minutes after exposure to 500 μg/mL N-Ac-CSHAVSSC-NH$_2$ (SEQ ID NO:28). FIG. 10B shows the cells 30 minutes after exposure to the control peptide N-Ac-CSHGVSSC-NH$_2$ (SEQ ID NO:51). FIG. 10C shows the cells in the absence of cyclic peptide. Note that the endothelial cells retracted from one another and round up in the presence of N-Ac-CSHAVSSC-NH$_2$ (SEQ ID NO:28).

FIG. 11A shows the cells 24 hours after being cultured in the presence of 500 μg/mL N-Ac-CHAVC-NH$_2$ (SEQ ID NO:10) (10× magnification). FIG. 11B shows the cells (10× magnification) 24 hours after being cultured in the presence of the control peptide N-Ac-CHGVC-NH$_2$ (SEQ ID NO:20). FIG. 11C shows the cells (10× magnification) in the absence of cyclic peptide. FIGS. 11D–F show the cells (20× magnification) 48 hours after exposure to N-Ac-CHAVC-NH$_2$ (SEQ ID NO:10) at concentrations of 1 mg/mL, 100 μg/mL and 10 μg/mL, respectively. Note that the SKOV3 cells retract from one another and round-up when cultured in the presence of either 0.5 or 1 mg/ml N-Ac-CHAVC-NH$_2$ (SEQ ID NO:10).

FIG. 14A shows untreated cells and FIGS. 14B–D show cells after 48 hours of exposure to either 1 mg/mL H-CAHVSC-OH (SEQ ID NO:42) (FIG. 14B), the control peptide N-Ac-CHGVC-NH$_2$ (SEQ ID NO:20), (FIG. 14C) or the representative cyclic peptide N-Ac-CHAVC-NH$_2$ (SEQ ID NO:10), (FIG. 14D). Note that E-cadherin expression is greatly reduced in the cells treated with N-Ac-CHAVC-NH$_2$ (SEQ ID NO:10), as compared to the E-cadherin levels expressed by untreated cells and cells treated with the other two cyclic peptides FIG. 15A shows the cells 24 hours after being cultured in the presence of 1 mg/ml of N-Ac-CAHVSC-NH$_2$ (SEQ ID NO:27). FIG. 15B shows the cells 24 hours after being cultured in the presence of 100 µg/ml of N-Ac-CAHVSC-NH$_2$ (SEQ ID NO:27). FIG. 15C shows the cells 24 hours after being cultured in the presence of 10 µg/ml of N-Ac-CAHVSC-NH$_2$ (SEQ ID NO:27). Note that the cells retract form one another in the presence of 100 µg/ml of N-Ac-CAHVSC-NH$_2$ (SEQ ID NO:27), whereas they round up in the presence of 1 mg/ml of this peptide.

FIG. 16B shows the cells 48 hours after being cultured in the presence of 500 µg/ml of N-Ac-CHAVC-NH$_2$ (SEQ ID NO:10). FIG. 16A shows untreated cultures of human melanoma ME115 cells. Note that cadherin is localized in intracellular vesicles in cells treated with peptide, whereas it is present at the surface in the untreated cells.

FIG. 17B shows the cells 48 hours after being cultured in the presence of 500 µg/ml of N-Ac-CHAVC-NH$_2$ (SEQ ID NO:10). FIG. 17A shows untreated monolayer cultures of A1N4 human breast epithelial cells. Note that the distribution of E-cadherin is non-contiguous in cells treated with the cyclic peptide. Furthermore, gaps have appeared in the monolayer of cells treated with the peptide.

FIGS. 30A and 30B show SKOV3 cells treated for 48 hours with the control peptide N-Ac-CHGVC-NH$_2$ (SEQ ID NO:20) at a concentration of 0.5 mg/mL (FIG. 30A) or 0.25 mg/mL (FIG. 30B). FIGS. 30C and 30D show SKOV3 cells treated for 48 hours with N-Ac-CHAVC-NH$_2$ (SEQ ID NO:10) at a concentration of 0.5 mg/mL (FIG. 30C) or 0.25 mg/mL (FIG. 30D). The fluorescent green nuclei in FIGS. 30C and 30D indicate cell death.

DETAILED DESCRIPTION OF THE INVENTION

Figure 1:
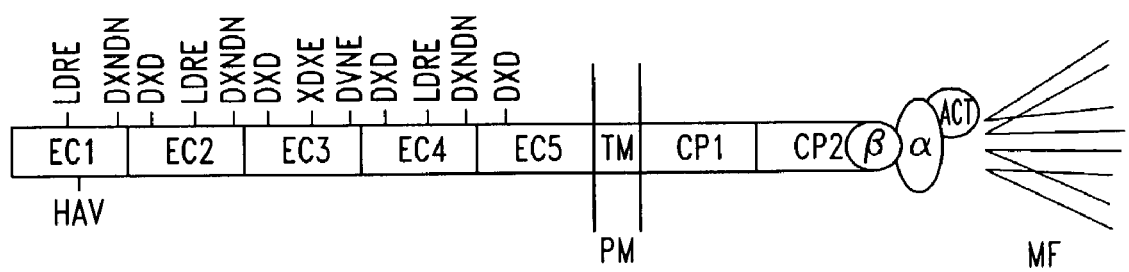
FIG. 1 is a diagram depicting the structure of classical CADs. The five extracellular domains are designated EC1–EC5, the hydrophobic domain that transverses the plasma membrane (PM) is represented by TM, and the two cytoplasmic domains are represented by CP1 and CP2. The calcium binding motifs are shown by DXNDN (SEQ ID NO:8), DXD and LDRE (SEQ ID NO:9). The CAR sequence, HAV, is shown within EC1. Cytoplasmic proteins β-catenin (β), α-catenin (α) and α-actinin (ACT), which mediate the interaction between CADs and microfilaments (MF) are also shown.

As noted above, the present invention provides modulating agents comprising cyclic peptides that are capable of inducing apoptosis in a cadherin-expressing cell, such as a cancer cell. The present invention is based, in part, on the discovery that certain cancer cells express one or more classical cadherins. Classical cadherins (CADs) are integral membrane glycoproteins that generally promote cell adhesion through homophilic interactions (a CAD on the surface of one cell binds to an identical CAD on the surface of another cell). Cadherins have been shown to regulate epithelial, endothelial, neural and cancer cell adhesion, with different CADs expressed on different cell types. N (neural)—cadherin is predominantly expressed by neural cells, endothelial cells and a variety of cancer cell types. E (epithelial)—cadherin is predominantly expressed by epithelial cells. Other CADs are P (placental)—cadherin, which is found in human skin and R (retinal)—cadherin. A detailed discussion of the classical cadherins is provided in Munro S B et al., 1996, In: *Cell Adhesion and Invasion in Cancer Metastasis*, P. Brodt, ed., pp. 17–34 (RG Landes Company, Austin Tex.). The structures of the CADs are generally similar. As illustrated in FIG. 1, CADs are composed of five extracellular domains (EC1–EC5), a single hydrophobic domain (TM) that transverses the plasma membrane (PM), and two cytoplasmic domains (CP1 and CP2). The calcium binding motifs DXNDN (SEQ ID NO:8), DXD and LDRE (SEQ ID NO:9) are interspersed throughout the extracellular domains. The first extracellular domain (EC1) contains the classical cadherin cell adhesion recognition (CAR) sequence, HAV (His-Ala-Val).

The present invention is further based on the discovery that cyclic peptides comprising a classical cadherin CAR sequence can induce apoptosis in certain cadherin-expressing cells (e.g., cancer cells). In general, to induce apoptosis, a cadherin-expressing cell is contacted with a modulating agent either in vivo or in vitro. Modulating agents comprising such sequences may be used to induce or enhance apoptosis in a variety of contexts, including within cancer therapies.

Modulating Agents

The term "modulating agent," as used herein, refers to a molecule comprising at least one cyclic peptide that contains a cadherin cell adhesion recognition (CAR) sequence, generally HAV (His-Ala-Val). The term "cyclic peptide," as used herein, refers to a peptide or salt thereof that comprises (1) an intramolecular covalent bond between two non-adjacent residues and (2) at least one cadherin CAR sequence. The intramolecular bond may be a backbone to backbone, side-chain to backbone or side-chain to side-chain bond (i.e., terminal functional groups of a linear peptide and/or side chain functional groups of a terminal or interior residue may be linked to achieve cyclization). Preferred intramolecular bonds include, but are not limited to, disulfide, amide and thioether bonds. In addition to the cadherin CAR sequence HAV, a modulating agent may comprise additional CAR sequences, which may or may not be cadherin CAR sequences, and/or antibodies or fragments thereof that specifically recognize a CAR sequence. Additional CAR sequences may be present within the cyclic peptide containing the HAV sequence, within a separate cyclic peptide component of the modulating agent and/or in a non-cyclic portion of the modulating agent. Antibodies and antigen-binding fragments thereof are typically present in a non-cyclic portion of the modulating agent.

In addition to the CAR sequence(s), cyclic peptides generally comprise at least one additional residue, such that the size of the cyclic peptide ring ranges from 4 to about 15 residues, preferably from 5 to 10 residues. Such additional residue(s) may be present on the N-terminal and/or C-terminal side of a CAR sequence, and may be derived from sequences that flank the HAV sequence within one or more naturally occurring cadherins (e.g., N-cadherin, E-cadherin, P-cadherin, R-cadherin or other cadherins containing the HAV sequence) with or without amino acid substitutions and/or other modifications. Flanking sequences for endogenous N-, E-, P- and R-cadherin are shown in FIG. 2, and in SEQ ID NOs: 1 to 7. Database accession numbers for representative naturally occurring cadherins are as follows: human N-cadherin M34064, mouse N-cadherin M31131 and M22556, cow N-cadherin X53615, human P-cadherin X63629, mouse P-cadherin X06340, human E-cadherin Z13009, mouse E-cadherin X06115. Alternatively, additional residues present on one or both sides of the CAR sequence(s) may be unrelated to an endogenous sequence (e.g., residues that facilitate cyclization).

Within certain preferred embodiments, as discussed below, relatively small cyclic peptides that do not contain significant sequences flanking the HAV sequence are preferred. Such peptides may contain an N-acetyl group and a C-amide group (e.g., the 5-residue ring N-Ac-CHAVC-NH$_2$ (SEQ ID NO:10) or N-Ac-KHAVD-NH$_2$ (SEQ ID NO:37)). The finding, within the present invention, that such relatively small cyclic peptides may be effective and all-purpose modulators of cadherin-mediated interactions represents a unexpected discovery. Such cyclic peptides can be thought of as "master keys" that fit into peptide binding sites of each of the different classical cadherins. Small cyclic peptides may generally be used to induce apoptosis of cells such as cancer cells by topical administration or by systemic administration, with or without linking a targeting agent to the peptide, as discussed below.

Within other preferred embodiments, a cyclic peptide may contain sequences that flank the HAV sequence on one or both sides that are designed to confer specificity for one or more specific cadherins, resulting in tissue and/or cell-type specificity. Suitable flanking sequences for conferring specificity include, but are not limited to, endogenous sequences present in one or more naturally occurring cadherins, and cyclic peptides having specificity may be identified using the representative screens provided herein. For example, it has been found, within the context of the present invention, that cyclic peptides that contain additional residues derived from the native E-cadherin sequence on the C-terminal side of the CAR sequence are specific for cells expressing E-cadherin (e.g., epithelial cells). The addition of appropriate endogenous sequences may similarly result in peptides that are specific for N-cadherin mediated interactions. For example, cyclic peptides that contain additional residues derived from the native N-cadherin sequence are specific for N-cadherin expressing cells (i.e., such peptides do not significantly interact with E-cadherin). Within preferred embodiments, such a cyclic peptide comprises at least one residue derived from a native N-cadherin sequence on the C-terminal side of the HAV sequence. The addition of a C-terminal amide group may further enhance activity of such peptides.

To facilitate the preparation of cyclic peptides having a desired specificity, nuclear magnetic resonance (NMR) and computational techniques may be used to determine the conformation of a peptide that confers a known specificity. NMR is widely used for structural analysis of molecules. Cross-peak intensities in nuclear Overhauser enhancement (NOE) spectra, coupling constants and chemical shifts depend on the conformation of a compound. NOE data provide the interproton distance between protons through space and across the ring of the cyclic peptide. This information may be used to facilitate calculation of the lowest energy conformation for the HAV sequence. Conformation may then be correlated with tissue specificity to permit the identification of peptides that are similarly tissue specific or have enhanced tissue specificity.

As noted above, multiple CAR sequences may be present within a modulating agent. CAR sequences that may be included within a modulating agent are any sequences specifically bound by an adhesion molecule. As used herein, an "adhesion molecule" is any molecule that mediates cell adhesion via a receptor on the cell's surface. In addition to classical cadherins, adhesion molecules include members of the cadherin gene superfamily that do not contain an HAV sequence and/or one or more of the other characteristics recited above for classical cadherins. Such cadherins are referred to herein as nonclassical cadherins, and include a typical cadherins (e.g., cadherin-11 (OB cadherin), cadherin-5 (VE-cadherin), cadherin-6 (K-cadherin), cadherin-7, cadherin-8, cadherin-12 (Br-cadherin, cadherin-14, cadherin-15, and PB-cadherin), desmocollins (dsc) and desmogleins (dsg). Other adhesion molecules include integrins; members of the immunoglobulin supergene family, such as N-CAM; the tight junction transmembrane proteins claudin and occludin; as well as extracellular matrix proteins such as laminin, fibronectin, collagens, vitronectin, entactin and tenascin. Preferred CAR sequences for inclusion within a modulating agent include (a) Arg-Gly-Asp (RGD), which is bound by integrins (see Cardarelli et al., *J. Biol. Chem.* 267:23159–64, 1992); (b) Tyr-Ile-Gly-Ser-Arg (YIGSR; SEQ ID NO:21), which is bound by $\alpha 6\beta 1$ integrin; (c) the occludin CAR sequence LYHY (SEQ ID NO:64) (d) claudin CAR sequences comprising at least four consecutive amino acids present within a claudin region that has the formula: Trp-Lys/Arg-Aaa-Baa-Ser/Ala-Tyr/Phe-Caa-Gly (SEQ ID NO:77), wherein Aaa, Baa and Caa indicate independently selected amino acid residues; Lys/Arg is an amino acid that is lysine or arginine; Ser/Ala is an amino acid that is serine or alanine; and Tyr/Phe is an amino acid that is tyrosine or phenylalanine; and (e) nonclassical cadherin CAR sequences comprising at least three consecutive amino acids present within a nonclassical cadherin region that has the formula: Aaa-Phe-Baa-Ile/Leu/Val-Asp/Asn/Glu-Caa-Daa-Ser/Thr/Asn-Gly (SEQ ID NO:65), wherein Aaa, Baa, Caa and Daa are independently selected amino acid residues; Ile/Leu/Val is an amino acid that is selected from the group consisting of isoleucine, leucine and valine, Asp/Asn/Glu is an amino acid that is selected from the group consisting of aspartate, asparagine and glutamate; and Ser/Thr/Asn is an amino acid that is selected from the group consisting of serine, threonine or asparagine. Representative claudin CAR sequences include IYSY (SEQ ID NO:66), TSSY (SEQ ID NO:67), VTAF (SEQ ID NO:68) and VSAF (SEQ ID NO:69). Representative nonclassical cadherin CAR sequences include the VE-cadherin CAR sequence DAE; the OB-cadherin CAR sequences DDK, EEY and EAQ; the dsg CAR sequences NQK, NRN and NKD and the dsc CAR sequences EKD and ERD. Multiple CAR sequences (which may all be HAV sequences, or may include other CAR sequences) may be employed in order to increase the potency of the modulating agent, to expand the target cells (e.g., incorporating an OB-cadherin CAR sequence) and/or to facilitate penetration into solid tumors (e.g., an agent that comprises a dsg CAR sequence).

Linkers may, but need not, be used to separate CAR sequences and/or antibody sequences within a modulating agent. Linkers may also, or alternatively, be used to attach one or more modulating agents to a support molecule or material, as described below. A linker may be any molecule (including peptide and/or non-peptide sequences as well as single amino acids or other molecules), that does not contain a CAR sequence and that can be covalently linked to at least two peptide sequences. Using a linker, HAV-containing cyclic peptides and other peptide or protein sequences may be joined head-to-tail (i.e., the linker may be covalently attached to the carboxyl or amino group of each peptide sequence), head-to-side chain and/or tail-to-side chain. Modulating agents comprising one or more linkers may form linear or branched structures. Within one embodiment, modulating agents having a branched structure comprise three different CAR sequences, such as RGD, YIGSR (SEQ ID NO:21) and HAV, one or more of which are present within a cyclic peptide. Within another embodiment, modulating agents having a branched structure comprise RGD, YIGSR (SEQ ID NO:21), HAV and KYSFNYDGSE (SEQ ID NO:22). In a third embodiment, modulating agents having a branched structure comprise HAV, LYHY (SEQ ID NO:64) and one or more dsc or dsg CAR sequences. Bi-functional modulating agents that comprise an HAV sequence with flanking E-cadherin-specific sequences joined via a linker to an HAV sequence with flanking N-cadherin-specific sequences are also preferred for certain embodiments.

Linkers preferably produce a distance between CAR sequences between 0.1 to 10,000 nm, more preferably about 0.1–400 nm. One linker that can be used for such purposes is $(H_2N(CH_2)_nCO_2H)_m$, or derivatives thereof, where n ranges from 1 to 10 and m ranges from 1 to 4000. For example, if glycine ($H_2NCH_2CO_2H$) or a multimer thereof is used as a linker, each glycine unit corresponds to a linking distance of 2.45 angstroms, or 0.245 nm, as determined by calculation of its lowest energy conformation when linked to other amino acids using molecular modeling techniques. Similarly, aminopropanoic acid corresponds to a linking distance of 3.73 angstroms, aminobutanoic acid to 4.96 angstroms, aminopentanoic acid to 6.30 angstroms and amino hexanoic acid to 6.12 angstroms. Other linkers that may be used will be apparent to those of ordinary skill in the art and include, for example, linkers based on repeat units of 2,3-diaminopropanoic acid, lysine and/or ornithine. 2,3-Diaminopropanoic acid can provide a linking distance of either 2.51 or 3.11 angstroms depending on whether the side-chain amino or terminal amino is used in the linkage. Similarly, lysine can provide linking distances of either 2.44 or 6.95 angstroms and ornithine 2.44 or 5.61 angstroms. Peptide and non-peptide linkers may generally be incorporated into a modulating agent using any appropriate method known in the art.

Modulating agents may contain one HAV sequence or multiple HAV sequences, which may be adjacent to one another (i.e., without intervening sequences) or in close proximity (i.e., separated by peptide and/or non-peptide linkers to give a distance between the CAR sequences that ranges from about 0.1 to 400 nm). Within one such embodiment, the cyclic peptide contains two HAV sequences. Such a modulating agent may additionally comprise a CAR sequence for one or more different adhesion molecules (including, but not limited to, other CAMs) and/or one or more antibodies or fragments thereof that bind to such sequences. Linkers may, but need not, be used to separate such CAR sequence(s) and/or antibody sequence(s) from the HAV sequence(s) and/or each other. Within certain preferred embodiments, the second CAR sequence is derived from fibronectin and is recognized by an integrin (i.e., RGD; see Cardarelli et al., *J. Biol. Chem.* 267:23159–23164, 1992), or is an OB-cadherin CAR sequence (DDK, EAQ or EEY), an occludin CAR sequence (e.g., LYHY; SEQ ID NO:64) or a CAR sequence for a desmoglein or desmocollin (NQK, NRN, NKD, EKD or ERD). One or more antibodies, or fragments thereof, may similarly be used within such embodiments.

Modulating agents and cyclic peptides as described herein may comprise residues of L-amino acids, D-amino acids, or any combination thereof. Amino acids may be from natural or non-natural sources, provided that at least one amino group and at least one carboxyl group are present in the molecule; α- and β-amino acids are generally preferred. The 20 L-amino acids commonly found in proteins are identified herein by the conventional three-letter or one-letter abbreviations indicated in Table 1, and the corresponding D-amino acids are designated by a lower case one letter symbol. Modulating agents and cyclic peptides may also contain one or more rare amino acids (such as 4-hydroxyproline or hydroxylysine), organic acids or amides and/or derivatives of common amino acids, such as amino acids having the C-terminal carboxylate esterified (e.g., benzyl, methyl or ethyl ester) or amidated and/or having modifications of the N-terminal amino group (e.g., acetylation or alkoxycarbonylation), with or without any of a wide variety of side-chain modifications and/or substitutions (e.g., methylation, benzylation, t-butylation, tosylation, alkoxycarbonylation, and the like). Preferred derivatives include amino acids having an N-acetyl group (such that the amino group that represents the N-terminus of the linear peptide prior to cyclization is acetylated) and/or a C-terminal amide group (i.e., the carboxy terminus of the linear peptide prior to cyclization is amidated). Residues other than common amino acids that may be present with a cyclic peptide include, but are not limited to, penicillamine, β,β-tetramethylene cysteine, ββ-pentamethylene cysteine, β-mercaptopropionic acid, β,β-pentamethylene-β-mercaptopropionic acid, 2-mercaptobenzene, 2-mercaptoaniline, 2-mercaptoproline, ornithine, diaminobutyric acid, α-aminoadipic acid, m-aminomethylbenzoic acid and α,β-diaminopropionic acid.

TABLE 1

Amino acid one-letter and three-letter abbreviations

| | | |
|---|---|---|
| A | Ala | Alanine |
| R | Arg | Arginine |
| D | Asp | Aspartic acid |
| N | Asn | Asparagine |
| C | Cys | Cysteine |
| Q | Gln | Glutamine |
| E | Glu | Glutamic acid |
| G | Gly | Glycine |
| H | His | Histidine |
| I | Ile | Isoleucine |
| L | Leu | Leucine |
| K | Lys | Lysine |
| M | Met | Methionine |
| F | Phe | Phenylalanine |
| P | Pro | Proline |
| S | Ser | Serine |
| T | Thr | Threonine |
| W | Trp | Tryptophan |
| Y | Tyr | Tyrosine |
| V | Val | Valine |

Modulating agents and cyclic peptides as described herein may be synthesized by methods well known in the art, including recombinant DNA methods and chemical synthesis. Chemical synthesis may generally be performed using standard solution phase or solid phase peptide synthesis techniques, in which a peptide linkage occurs through the direct condensation of the α-amino group of one amino acid with the α-carboxy group of the other amino acid with the elimination of a water molecule. Peptide bond synthesis by direct condensation, as formulated above, requires suppression of the reactive character of the amino group of the first and of the carboxyl group of the second amino acid. The masking substituents must permit their ready removal, without inducing breakdown of the labile peptide molecule.

In solution phase synthesis, a wide variety of coupling methods and protecting groups may be used (see Gross and Meienhofer, eds., "The Peptides: Analysis, Synthesis, Biology," Vol. 1–4 (Academic Press, 1979); Bodansky and Bodansky, "The Practice of Peptide Synthesis," 2d ed. (Springer Verlag, 1994)). In addition, intermediate purification and linear scale up are possible. Those of ordinary skill in the art will appreciate that solution synthesis requires consideration of main chain and side chain protecting groups and activation method. In addition, careful segment selection is necessary to minimize racemization during segment condensation. Solubility considerations are also a factor.

Solid phase peptide synthesis uses an insoluble polymer for support during organic synthesis. The polymer-supported peptide chain permits the use of simple washing and filtration steps instead of laborious purifications at intermediate steps. Solid-phase peptide synthesis may generally be performed according to the method of Merrifield et al., *J. Am. Chem. Soc.* 85:2149, 1963, which involves assembling a linear peptide chain on a resin support using protected amino acids. Solid phase peptide synthesis typically utilizes either the Boc or Fmoc strategy. The Boc strategy uses a 1% cross-linked polystyrene resin. The standard protecting group for α-amino functions is the tert-butyloxycarbonyl (Boc) group. This group can be removed with dilute solutions of strong acids such as 25% trifluoroacetic acid (TFA). The next Boc-amino acid is typically coupled to the amino acyl resin using dicyclohexylcarbodiimide (DCC). Following completion of the assembly, the peptide-resin is treated with anhydrous HF to cleave the benzyl ester link and liberate the free peptide. Side-chain functional groups are usually blocked during synthesis by benzyl-derived blocking groups, which are also cleaved by HF. The free peptide is then extracted from the resin with a suitable solvent, purified and characterized. Newly synthesized peptides can be purified, for example, by gel filtration, HPLC, partition chromatography and/or ion-exchange chromatography, and may be characterized by, for example, mass spectrometry or amino acid sequence analysis. In the Boc strategy, C-terminal amidated peptides can be obtained using benzhydrylamine or methylbenzhydrylamine resins, which yield peptide amides directly upon cleavage with HF.

In the procedures discussed above, the selectivity of the side-chain blocking groups and of the peptide-resin link depends upon the differences in the rate of acidolytic cleavage. Orthoganol systems have been introduced in which the side-chain blocking groups and the peptide-resin link are completely stable to the reagent used to remove the α-protecting group at each step of the synthesis. The most common of these methods involves the 9-fluorenylmethyloxycarbonyl (Fmoc) approach. Within this method, the side-chain protecting groups and the peptide-resin link are completely stable to the secondary amines used for cleaving the N-α-Fmoc group. The side-chain protection and the peptide-resin link are cleaved by mild acidolysis. The repeated contact with base makes the Merrifield resin unsuitable for Fmoc chemistry, and p-alkoxybenzyl esters linked to the resin are generally used. Deprotection and cleavage are generally accomplished using TFA.

Those of ordinary skill in the art will recognize that, in solid phase synthesis, deprotection and coupling reactions must go to completion and the side-chain blocking groups must be stable throughout the entire synthesis. In addition, solid phase synthesis is generally most suitable when peptides are to be made on a small scale.

Acetylation of the N-terminal can be accomplished by reacting the final peptide with acetic anhydride before cleavage from the resin. C-amidation is accomplished using an appropriate resin such as methylbenzhydrylamine resin using the Boc technology.

Following synthesis of a linear peptide, with or without N-acetylation and/or C-amidation, cyclization may be achieved by any of a variety of techniques well known in the art. Within one embodiment, a bond may be generated between reactive amino acid side chains. For example, a disulfide bridge may be formed from a linear peptide comprising two thiol-containing residues by oxidizing the peptide using any of a variety of methods. Within one such method, air oxidation of thiols can generate disulfide linkages over a period of several days using either basic or neutral aqueous media. The peptide is used in high dilution to minimize aggregation and intermolecular side reactions. This method suffers from the disadvantage of being slow but has the advantage of only producing $H_2O$ as a side product. Alternatively, strong oxidizing agents such as $I_2$ and $K_3Fe(CN)_6$ can be used to form disulfide linkages. Those of ordinary skill in the art will recognize that care must be taken not to oxidize the sensitive side chains of Met, Tyr, Trp or His. Cyclic peptides produced by this method require purification using standard techniques, but this oxidation is applicable at acid pHs. By way of example, strong oxidizing agents can be used to perform the cyclization shown below (SEQ ID NOs: 23 and 79), in which the underlined portion is cyclized:

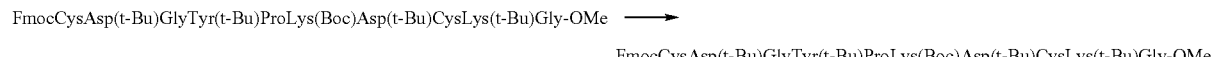

Oxidizing agents also allow concurrent deprotection/oxidation of suitable S-protected linear precursors to avoid premature, nonspecific oxidation of free cysteine, as shown below (SEQ ID NOs: 24 and 80), where X and Y=S-Trt or S-Acm:

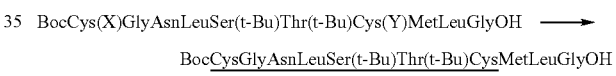

DMSO, unlike $I_2$ and $K_3Fe(CN)_6$, is a mild oxidizing agent which does not cause oxidative side reactions of the nucleophilic amino acids mentioned above. DMSO is miscible with $H_2O$ at all concentrations, and oxidations can be performed at acidic to neutral pHs with harmless byproducts. Methyltrichlorosilane-diphenylsulfoxide may alternatively be used as an oxidizing agent, for concurrent deprotection/oxidation of S-Acm, S-Tacm or S-t-Bu of cysteine without affecting other nucleophilic amino acids. There are no polymeric products resulting from intermolecular disulfide bond formation. In the example below (SEQ ID NOs: 25 and 81), X is Acm, Tacm or t-Bu:

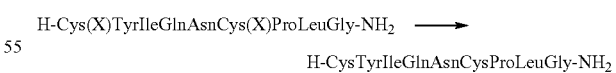

Suitable thiol-containing residues for use in such oxidation methods include, but are not limited to, cysteine, β,β-dimethyl cysteine (penicillamine or Pen), β,β-tetramethylene cysteine (Tmc), β,β-pentamethylene cysteine (Pmc), β-mercaptopropionic acid (Mpr), β,β-pentamethylene-β-mercaptopropionic acid (Pmp), 2-mercaptobenzene, 2-mercaptoaniline and 2-mercaptoproline. Peptides containing such residues are illustrated by the following representative formulas, in which the underlined portion is cyclized, N-acetyl groups are indicated by N-Ac and C-terminal amide groups are represented by -NH$_2$:

| | | |
|---|---|---|
| i) | N-Ac-<u>Cys</u>-His-Ala-Val-<u>Cys</u>-NH$_2$ | (SEQ ID NO:10) |
| ii) | N-Ac-<u>Cys</u>-Ala-His-Ala-Val-Asp-Ile-<u>Cys</u>-NH$_2$ | (SEQ ID NO:14) |
| iii) | N-Ac-<u>Cys</u>-Ser-His-Ala-Val-<u>Cys</u>-NH$_2$ | (SEQ ID NO:26) |
| iv) | N-Ac-<u>Cys</u>-His-Ala-Val-Ser-<u>Cys</u>-NH$_2$ | (SEQ ID NO:27) |
| v) | N-Ac-<u>Cys</u>-Ala-His-Ala-Val-Asp-<u>Cys</u>-NH$_2$ | (SEQ ID NO:13) |
| vi) | N-Ac-<u>Cys</u>-Ser-His-Ala-Val-Ser-<u>Cys</u>-NH$_2$ | (SEQ ID NO:28) |
| vii) | N-Ac-<u>Cys</u>-His-Ala-Val-Ser-<u>Cys</u>-OH (SEQ ID NO:27) | |
| viii) | H-<u>Cys</u>-Ala-His-Ala-Val-Asp-<u>Cys</u>-NH$_2$ | (SEQ ID NO:13) |
| ix) | N-Ac-<u>Cys</u>-His-Ala-Val-<u>Pen</u>-NH$_2$ | (SEQ ID NO:29) |
| x) | N-Ac-Ile-<u>Tmc</u>-Tyr-Ser-His-Ala-Val-Ser-<u>Cys</u>-Glu-NH$_2$ | (SEQ ID NO:30) |
| xi) | N-Ac-Ile-<u>Pmc</u>-Tyr-Ser-His-Ala-Val-Ser-Ser-<u>Cys</u>-NH$_2$ | (SEQ ID NO:31) |
| xii) | <u>Mpr</u>-Tyr-Ser-His-Ala-Val-Ser-Ser-Cys-NH$_2$ | (SEQ ID NO:32) |
| xiii) | <u>Pmp</u>-Tyr-Ser-His-Ala-Val-Ser-Ser-Cys-NH$_2$ | (SEQ ID NO:33) |

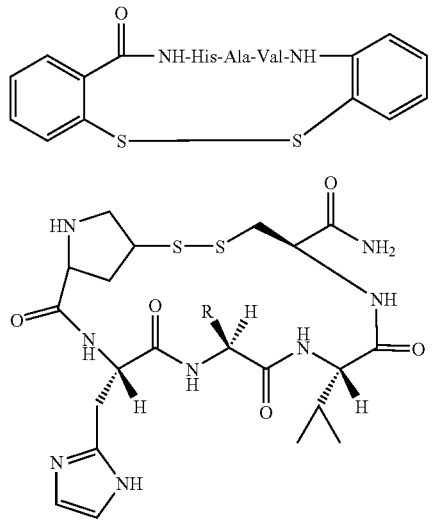

It will be readily apparent to those of ordinary skill in the art that, within each of these representative formulas, any of the above thiol-containing residues may be employed in place of one or both of the thiol-containing residues recited.

Within another embodiment, cyclization may be achieved by amide bond formation. For example, a peptide bond may be formed between terminal functional groups (i.e., the amino and carboxy termini of a linear peptide prior to cyclization). Two such cyclic peptides are <u>AHAVDI</u> (SEQ ID NO:19) and <u>SHAVSS</u> (SEQ ID NO:34), with or without an N-terminal acetyl group and/or a C-terminal amide. Within another such embodiment, the linear peptide comprises a D-amino acid (e.g., <u>HAVsS</u>; SEQ ID NO:35). Alternatively, cyclization may be accomplished by linking one terminus and a residue side chain or using two side chains, as in <u>KHAVD</u> (SEQ ID NO:37) or <u>KSHAVSSD</u> (SEQ ID NO:60), with or without an N-terminal acetyl group and/or a C-terminal amide. Residues capable of forming a lactam bond include lysine, ornithine (Orn), α-amino adipic acid, m-aminomethylbenzoic acid, α,β-diaminopropionic acid, glutamate or aspartate.

Methods for forming amide bonds are well known in the art and are based on well established principles of chemical reactivity. Within one such method, carbodiimide-mediated lactam formation can be accomplished by reaction of the carboxylic acid with DCC, DIC, EDAC or DCCI, resulting in the formation of an O-acylurea that can be reacted immediately with the free amino group to complete the cyclization. The formation of the inactive N-acylurea, resulting from O→N migration, can be circumvented by converting the O-acylurea to an active ester by reaction with an N-hydroxy compound such as 1-hydroxybenzotriazole, 1-hydroxysuccinimide, 1-hydroxynorbornene carboxamide or ethyl 2-hydroximino-2-cyanoacetate. In addition to minimizing O→N migration, these additives also serve as catalysts during cyclization and assist in lowering racemization. Alternatively, cyclization can be performed using the azide method, in which a reactive azide intermediate is generated from an alkyl ester via a hydrazide. Hydrazinolysis of the terminal ester necessitates the use of a t-butyl group for the protection of side chain carboxyl functions in the acylating component. This limitation can be overcome by using diphenylphosphoryl acid (DPPA), which furnishes an azide directly upon reaction with a carboxyl group. The slow reactivity of azides and the formation of isocyanates by their disproportionation restrict the usefulness of this method. The mixed anhydride method of lactam formation is widely used because of the facile removal of reaction by-products. The anhydride is formed upon reaction of the carboxylate anion with an alkyl chloroformate or pivaloyl chloride. The attack of the amino component is then guided to the carbonyl carbon of the acylating component by the electron donating effect of the alkoxy group or by the steric bulk of the pivaloyl chloride t-butyl group, which obstructs attack on the wrong carbonyl group. Mixed anhydrides with phosphoric acid derivatives have also been successfully used. Alternatively, cyclization can be accomplished using activated esters. The presence of electron withdrawing substituents on the alkoxy carbon of esters increases their susceptibility to aminolysis. The high reactivity of esters of p-nitrophenol, N-hydroxy compounds and polyhalogenated phenols has made these "active esters" useful in the synthesis of amide bonds. The last few years have witnessed the development of benzotriazolyloxytris-(dimethylamino)phosphonium hexafluorophosphonate (BOP) and its congeners as advantageous coupling reagents. Their performance is generally superior to that of the well established carbodiimide amide bond formation reactions.

Within a further embodiment, a thioether linkage may be formed between the side chain of a thiol-containing residue and an appropriately derivatized α-amino acid. By way of example, a lysine side chain can be coupled to bromoacetic acid through the carbodiimide coupling method (DCC, EDAC) and then reacted with the side chain of any of the thiol containing residues mentioned above to form a thioether linkage. In order to form dithioethers, any two thiol containing side-chains can be reacted with dibromoethane and diisopropylamine in DMF. Examples of thiol-containing linkages are shown below:

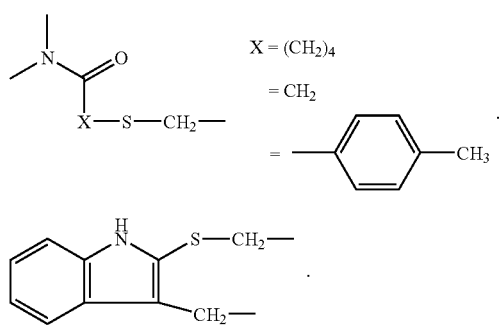

Cyclization may also be achieved using $\delta_1\delta_1$-Ditryptophan (i.e., Ac-Trp-Gly-Gly-Trp-OMe) (SEQ ID NO:36), as shown below:

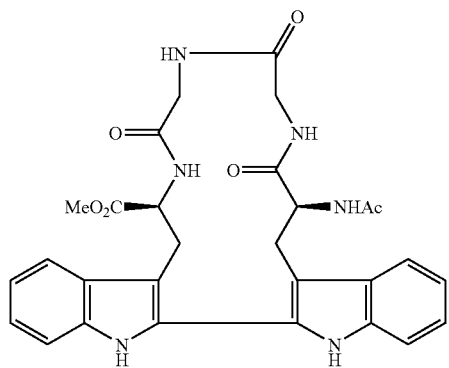

Representative structures of cyclic peptides are provided in FIG. 3. Within FIG. 3, certain cyclic peptides having the ability to modulate cell adhesion (shown on the left) are paired with similar inactive structures (on the right). The structures and formulas recited herein are provided solely for the purpose of illustration, and are not intended to limit the scope of the cyclic peptides described herein.

As noted above, a modulating agent may consist entirely of one or more cyclic peptides, or may contain additional peptide and/or non-peptide sequences, which may be linked to the cyclic peptide(s) using conventional techniques. Peptide portions may be synthesized as described above or may be prepared using recombinant methods. Within such methods, all or part of a modulating agent can be synthesized in living cells, using any of a variety of expression vectors known to those of ordinary skill in the art to be appropriate for the particular host cell. Suitable host cells may include bacteria, yeast cells, mammalian cells, insect cells, plant cells, algae and other animal cells (e.g., hybridoma, CHO, myeloma). The DNA sequences expressed in this manner may encode portions of an endogenous cadherin or other adhesion molecule. Such sequences may be prepared based on known cDNA or genomic sequences (see Blaschuk et al., J. Mol. Biol. 211: 679–682, 1990), or from sequences isolated by screening an appropriate library with probes designed based on the sequences of known cadherins. Such screens may generally be performed as described in Sambrook et al., Molecular Cloning: A Laboratory Manual, Cold Spring Harbor Laboratories, Cold Spring Harbor, N.Y., 1989 (and references cited therein). Polymerase chain reaction (PCR) may also be employed, using oligonucleotide primers in methods well known in the art, to isolate nucleic acid molecules encoding all or a portion of an endogenous adhesion molecule. To generate a nucleic acid molecule encoding a peptide portion of a modulating agent, an endogenous sequence may be modified using well known techniques. For example, portions encoding one or more CAR sequences may be joined, with or without separation by nucleic acid regions encoding linkers, as discussed above. Alternatively, portions of the desired nucleic acid sequences may be synthesized using well known techniques, and then ligated together to form a sequence encoding a portion of the modulating agent.

As noted above, portions of a modulating agent may comprise an antibody, or antigen-binding fragment thereof, that specifically binds to a CAR sequence. As used herein, an antibody, or antigen-binding fragment thereof, is said to "specifically bind" to a CAR sequence (with or without flanking amino acids) if it reacts at a detectable level (within, for example, an ELISA, as described by Newton et al., Develop. Dynamics 197:1–13, 1993) with a peptide containing that sequence, and does not react detectably with peptides containing a different CAR sequence or a sequence in which the order of amino acid residues in the cadherin CAR sequence and/or flanking sequence is altered.

Antibodies and fragments thereof may be prepared using standard techniques. See, e.g., Harlow and Lane, Antibodies: A Laboratory Manual, Cold Spring Harbor Laboratory, 1988. In one such technique, an immunogen comprising a CAR sequence is initially injected into any of a wide variety of mammals (e.g., mice, rats, rabbits, sheep or goats). Small immunogens (i.e., less than about 20 amino acids) should be joined to a carrier protein, such as bovine serum albumin or keyhole limpet hemocyanin. Following one or more injections, the animals are bled periodically. Polyclonal antibodies specific for the CAR sequence may then be purified from such antisera by, for example, affinity chromatography using the modulating agent or antigenic portion thereof coupled to a suitable solid support.

Monoclonal antibodies specific for a CAR sequence may be prepared, for example, using the technique of Kohler and Milstein, Eur. J. Immunol. 6:511–519, 1976, and improvements thereto. Briefly, these methods involve the preparation of immortal cell lines capable of producing antibodies having the desired specificity from spleen cells obtained from an animal immunized as described above. The spleen cells are immortalized by, for example, fusion with a myeloma cell fusion partner, preferably one that is syngeneic with the immunized animal. Single colonies are selected and their culture supernatants tested for binding activity against the modulating agent or antigenic portion thereof. Hybridomas having high reactivity and specificity are preferred.

Monoclonal antibodies may be isolated from the supernatants of growing hybridoma colonies, with or without the use of various techniques known in the art to enhance the yield. Contaminants may be removed from the antibodies by conventional techniques, such as chromatography, gel filtration, precipitation, and extraction. Antibodies having the desired activity may generally be identified using immunofluorescence analyses of tissue sections, cell or other samples where the target cadherin is localized.

Within certain embodiments, monoclonal antibodies may be specific for particular cadherins (e.g., the antibodies bind to E-cadherin, but do not bind significantly to N-cadherin, or vise versa). Such antibodies may be prepared as described above, using an immunogen that comprises (in addition to the HAV sequence) sufficient flanking sequence to generate the desired specificity (e.g., 5 amino acids on each side is generally sufficient). One representative immunogen is the 15-mer FHLRAHAVDINGNQV-NH$_2$ (SEQ ID NO:60), linked to KLH (see Newton et al., *Dev. Dynamics* 197:1–13, 1993). To evaluate the specificity of a particular antibody, representative assays as described herein and/or conventional antigen-binding assays may be employed. Such antibodies may generally be used for therapeutic, diagnostic and assay purposes, as described herein. For example, such antibodies may be linked to a drug and administered to a mammal to target the drug to a particular cadherin-expressing cell, such as a leukemic cell in the blood.

Within certain embodiments, the use of antigen-binding fragments of antibodies may be preferred. Such fragments include Fab fragments, which may be prepared using standard techniques. Briefly, immunoglobulins may be purified from rabbit serum by affinity chromatography on Protein A bead columns (Harlow and Lane, *Antibodies: A Laboratory Manual,* Cold Spring Harbor Laboratory, 1988; see especially page 309) and digested by papain to yield Fab and Fe fragments. The Fab and Fe fragments may be separated by affinity chromatography on protein A bead columns (Harlow and Lane, 1988, pages 628–29).

Evaluation of Modulation Agent Activity

As noted above, cyclic peptides and other modulating agents as described herein are capable of inducing apoptosis in certain cadherin-expressing cells. The ability of a modulating agent to induce apoptosis in such cells may be evaluated using an assay that detects modulation of cadherin-mediated cell adhesion, or using an assay that directly detects the level of cell death. The ability of a modulating agent to modulate cell adhesion may generally be evaluated in vitro by assaying the effect of the cyclic peptide on one or more of the following: (1) neurite outgrowth, (2) adhesion between endothelial cells, (3) adhesion between epithelial cells (e.g., normal rat kidney cells and/or human skin) and/or (4) adhesion between cancer cells. In general, contact of test cells with a modulating agent should result in a discernible disruption of cell adhesion within one or more of the above assays. Alternatively, or in addition, induction of apoptosis may be directly determined as described herein.

Within a representative neurite outgrowth assay, neurons may be cultured on a monolayer of cells (e.g., 3T3) that express N-cadherin. Neurons grown on such cells (under suitable conditions and for a sufficient period of time) extend longer neurites than neurons cultured on cells that do not express N-cadherin. For example, neurons may be cultured on monolayers of 3T3 cells transfected with cDNA encoding N-cadherin essentially as described by Doherty and Walsh, *Curr. Op. Neurobiol.* 4:49–55, 1994; Williams et al., *Neuron* 13:583–594, 1994; Hall et al., *Cell Adhesion and Commun.* 3:441–450, 1996; Doherty and Walsh, *Mol. Cell. Neurosci.* 8:99–111, 1994; and Safell et al., *Neuron* 18:231–242, 1997. Briefly, monolayers of control 3T3 fibroblasts and 3T3 fibroblasts that express N-cadherin may be established by overnight culture of 80,000 cells in individual wells of an 8-chamber well tissue culture slide. 3000 cerebellar neurons isolated from post-natal day 3 mouse brains may be cultured for 18 hours on the various monolayers in control media (SATO/2% FCS), or media supplemented with various concentrations of the modulating agent or control peptide. The cultures may then be fixed and stained for GAP43 which specifically binds to the neurons and their neurites. The length of the longest neurite on each GAP43 positive neuron may be measured by computer assisted morphometry.

A modulating agent that modulates N-cadherin-mediated cell adhesion may inhibit or enhance such neurite outgrowth. Under the conditions described above, the presence of 500 µg/mL of a modulating agent that disrupts neural cell adhesion should result in a decrease in the mean neurite length by at least 50%, relative to the length in the absence of modulating agent or in the presence of a negative control peptide. Alternatively, the presence of 500 µg/mL of a modulating agent that enhances neural cell adhesion should result in an increase in the mean neurite length by at least 50%.

Within one representative cell adhesion assay, the addition of a modulating agent to cells that express a cadherin results in disruption of cell adhesion. A "cadherin-expressing cell," as used herein, may be any type of cell that expresses at least one cadherin on the cell surface at a detectable level, using standard techniques such as immunocytochemical protocols (Blaschuk and Farookhi, *Dev. Biol.* 136:564–567, 1989). Cadherin-expressing cells include endothelial (e.g., bovine pulmonary artery endothelial cells), epithelial and/or cancer cells (e.g., the human ovarian cancer cell line SKOV3 (ATCC #HTB-77)). For example, such cells may be plated under standard conditions that permit cell adhesion in the presence and absence of modulating agent (e.g., 500 µg/mL). Disruption of cell adhesion may be determined visually within 24 hours, by observing retraction of the cells from one another.

For use within one such assay, bovine pulmonary artery endothelial cells may be harvested by sterile ablation and digestion in 0.1% collagenase (type II; Worthington Enzymes, Freehold, N.J.). Cells may be maintained in Dulbecco's minimum essential medium supplemented with 10% fetal calf serum and 1% antibiotic-antimycotic at 37° C. in 7% $CO_2$ in air. Cultures may be passaged weekly in trypsin-EDTA and seeded onto tissue culture plastic at 20,000 cells/cm$^2$. Endothelial cultures may be used at 1 week in culture, which is approximately 3 days after culture confluency is established. The cells may be seeded onto coverslips and treated (e.g., for 30 minutes) with modulating agent or a control compound at, for example, 500 µg/ml and then fixed with 1% paraformaldehyde. As noted above, disruption of cell adhesion may be determined visually within 24 hours, by observing retraction of the cells from one another. This assay evaluates the effect of a modulating agent on N-cadherin mediated cell adhesion.

Within another such assay, the effect of a modulating agent on normal rat kidney (NRK) cells may be evaluated. According to a representative procedure, NRK cells (ATCC

1571-CRL) may be plated at 10–20,000 cells per 35 mm tissue culture flasks containing DMEM with 10% FCS and sub-cultured periodically (Laird et al., *J. Cell Biol.* 131: 1193–1203, 1995). Cells may be harvested and replated in 35 mm tissue culture flasks containing 1 mm coverslips and incubated until 50–65% confluent (24–36 hours). At this time, coverslips may be transferred to a 24-well plate, washed once with fresh DMEM and exposed to modulating agent at a concentration of, for example, 1 mg/mL for 24 hours. Fresh modulating agent may then be added, and the cells left for an additional 24 hours. Cells may be fixed with 100% methanol for 10 minutes and then washed three times with PBS. Coverslips may be blocked for 1 hour in 2% BSA/PBS and incubated for a further 1 hour in the presence of mouse anti-E-cadherin antibody (Transduction Labs, 1:250 dilution). Primary and secondary antibodies may be diluted in 2% BSA/PBS. Following incubation in the primary antibody, coverslips may be washed three times for 5 minutes each in PBS and incubated for 1 hour with donkey anti-mouse antibody conjugated to fluorescein (diluted 1:200). Following further washes in PBS (3×5 min) coverslips can be mounted and viewed by confocal microscopy.

In the absence of modulating agent, NRK cells form characteristic tightly adherent monolayers with a cobblestone morphology in which cells display a polygonal shape. NRK cells that are treated with a modulating agent that disrupts E-cadherin mediated cell adhesion may assume a non-polygonal and elongated morphology (i.e., a fibroblast-like shape) within 48 hours of treatment with 1 mg/mL of modulating agent. Gaps appear in confluent cultures of such cells. In addition, 1 mg/mL of such a modulating agent reproducibly induces a readily apparent reduction in cell surface staining of E-cadherin, as judged by immunofluorescence microscopy (Laird et al., *J. Cell Biol.* 131:1193–1203, 1995), of at least 75% within 48 hours.

A third cell adhesion assay involves evaluating the effect of a cyclic peptide on permeability of adherent epithelial and/or endothelial cell layers. For example, the effect of permeability on human skin may be evaluated. Such skin may be derived from a natural source or may be synthetic. Human abdominal skin for use in such assays may generally be obtained from humans at autopsy within 24 hours of death. Briefly, a cyclic peptide and a test marker (e.g., the fluorescent markers Oregon Green™ and Rhodamine Green™ Dextran) may be dissolved in a sterile buffer, and the ability of the marker to penetrate through the skin and into a receptor fluid may be measured using a Franz Cell apparatus (Franz, *Curr. Prob. Dermatol.* 7:58–68, 1978; Franz, *J. Invest. Dermatol.* 64:190–195, 1975). In general, a modulating agent that enhances the permeability of human skin results in a statistically significant increase in the amount of marker in the receptor compartment after 6–48 hours in the presence of 500 µg/mL modulating agent. This assay evaluates the effect of a modulating agent on E-cadherin mediated cell adhesion.

Direct assays of induction of apoptosis may be performed using any standard technique. For example, cadherin-expressing cells (e.g., SKOV3 human ovarian cancer cells) may be plated onto poly-L-lysine coated glass slides and cultured with 500 µg/mL of modulating agent for 24–48 hours. Cells may then be fixed and assayed for cell death using any of a variety of well known methods. For example, an in situ cell death detection kit may be purchased from Boehringer Mannheim (Laval, Quebec) and used according to the manufacturer's instructions.

Modulating Agent Modification and Formulations

A modulating agent as described herein may, but need not, be linked to one or more additional molecules. In particular, as discussed below, it may be beneficial for certain applications to link multiple modulating agents (which may, but need not, be identical) to a support molecule (e.g., keyhole limpet hemocyanin) or a solid support, such as a polymeric matrix (which may be formulated as a membrane or microstructure, such as an ultra thin film), a container surface (e.g., the surface of a tissue culture plate or the interior surface of a bioreactor), or a bead or other particle, which may be prepared from a variety of materials including glass, plastic or ceramics. For certain applications, biodegradable support materials are preferred, such as cellulose and derivatives thereof, collagen, spider silk or any of a variety of polyesters (e.g., those derived from hydroxy acids and/or lactones) or sutures (see U.S. Pat. No. 5,245,012). Within certain embodiments, modulating agents and molecules comprising other CAR sequence(s) (e.g., an RGD and/or LYHY (SEQ ID NO:64) sequence) may be attached to a support such as a polymeric matrix, preferably in an alternating pattern.

Suitable methods for linking a modulating agent to a support material will depend upon the composition of the support and the intended use, and will be readily apparent to those of ordinary skill in the art. Attachment may generally be achieved through noncovalent association, such as adsorption or affinity or, preferably, via covalent attachment (which may be a direct linkage between a modulating agent and functional groups on the support, or may be a linkage by way of a cross-linking agent or linker). Attachment of a modulating agent by adsorption may be achieved by contact, in a suitable buffer, with a solid support for a suitable amount of time. The contact time varies with temperature, but is generally between about 5 seconds and 1 day, and typically between about 10 seconds and 1 hour.

Covalent attachment of a modulating agent to a molecule or solid support may generally be achieved by first reacting the support material with a bifunctional reagent that will also react with a functional group, such as a hydroxyl, thiol, carboxyl, ketone or amino group, on the modulating agent. For example, a modulating agent may be bound to an appropriate polymeric support or coating using benzoquinone, by condensation of an aldehyde group on the support with an amine and an active hydrogen on the modulating agent or by condensation of an amino group on the support with a carboxylic acid on the modulating agent. A preferred method of generating a linkage is via amino groups using glutaraldehyde. A modulating agent may be linked to cellulose via ester linkages. Similarly, amide linkages may be suitable for linkage to other molecules such as keyhole limpet hemocyanin or other support materials. Multiple modulating agents and/or molecules comprising other CAR sequences may be attached, for example, by random coupling, in which equimolar amounts of such molecules are mixed with a matrix support and allowed to couple at random.

Although modulating agents as described herein may preferentially bind to specific tissues or cells, and thus may be sufficient to target a desired site in vivo, it may be beneficial for certain applications to include an additional targeting agent. Accordingly, a targeting agent may also, or alternatively, be linked to a modulating agent to facilitate targeting to one or more specific tissues. As used herein, a "targeting agent," may be any substance (such as a compound or cell) that, when linked to a modulating agent enhances the transport of the modulating agent to a target tissue, thereby increasing the local concentration of the modulating agent. Targeting agents include antibodies or fragments thereof, receptors, ligands and other molecules that bind to cells of, or in the vicinity of, the target tissue. Known targeting agents include serum hormones, antibodies against cell surface antigens, lectins, adhesion molecules, tumor cell surface binding ligands, steroids, cholesterol, lymphokines, fibrinolytic enzymes and those drugs and proteins that bind to a desired target site. Among the many monoclonal antibodies that may serve as targeting agents are anti-TAC, or other interleukin-2 receptor antibodies; 9.2.27 and NR-ML-05, reactive with the 250 kilodalton human melanoma-associated proteoglycan; and NR-LU-10, reactive with a pancarcinoma glycoprotein. An antibody targeting agent may be an intact (whole) molecule, a fragment thereof, or a functional equivalent thereof. Examples of antibody fragments are F(ab')2, -Fab', Fab and F[v] fragments, which may be produced by conventional methods or by genetic or protein engineering. Linkage is generally covalent and may be achieved by, for example, direct condensation or other reactions, or by way of bi- or multi-functional linkers. Within other embodiments, it may also be possible to target a polynucleotide encoding a modulating agent to a target tissue, thereby increasing the local concentration of modulating agent. Such targeting may be achieved using well known techniques, including retroviral and adenoviral infection.

For certain embodiments, it may be beneficial to also, or alternatively, link a drug to a modulating agent. As used herein, the term "drug" refers to any bioactive agent intended for administration to a mammal to prevent or treat a disease or other undesirable condition. Drugs include hormones, growth factors, proteins, peptides and other compounds. The use of certain specific drugs within the context of the present invention is discussed below.

Within certain aspects of the present invention, one or more modulating agents as described herein may be present within a pharmaceutical composition. A pharmaceutical composition comprises one or more modulating agents in combination with one or more pharmaceutically or physiologically acceptable carriers, diluents or excipients. Such compositions may comprise buffers (e.g., neutral buffered saline or phosphate buffered saline), carbohydrates (e.g., glucose, mannose, sucrose or dextrans), mannitol, proteins, polypeptides or amino acids such as glycine, antioxidants, chelating agents such as EDTA or glutathione, adjuvants (e.g., aluminum hydroxide) and/or preservatives. Within yet other embodiments, compositions of the present invention may be formulated as a lyophilizate. A modulating agent (alone or in combination with a targeting agent and/or drug) may, but need not, be encapsulated within liposomes using well known technology. Compositions of the present invention may be formulated for any appropriate manner of administration, including for example, topical, oral, nasal, intravenous, intracranial, intraperitoneal, subcutaneous, or intramuscular administration. For certain topical applications, formulation as a cream or lotion, using well known components, is preferred.

For certain embodiments, as discussed below, a pharmaceutical composition may further comprise a modulator of cell adhesion that is mediated by one or more molecules other than cadherins. Such modulators may generally be prepared as described above, incorporating one or more non-cadherin CAR sequences and/or antibodies thereto in place of the cadherin CAR sequences and antibodies. Such compositions are particularly useful for situations in which it is desirable to inhibit cell adhesion mediated by multiple cell-adhesion molecules, such as other members of the cadherin gene superfamily that are not classical cadherins (e.g., Dsg and Dsc); integrins; members of the immunoglobulin supergene family, such as N-CAM; tight junction transmembrane proteins such as occludin and claudins; as well as extracellular matrix proteins such as laminin, fibronectin, collagens, vitronectin, entactin and tenascin.

A pharmaceutical composition may also contain one or more drugs, which may be linked to a modulating agent or may be free within the composition. Virtually any drug may be administered in combination with a cyclic peptide as described herein, for a variety of purposes as described below. Preferred drugs are anticancer agents.

The compositions described herein may be administered as part of a sustained release formulation (i.e., a formulation such as a capsule or sponge that effects a slow release of cyclic peptide following administration). Such formulations may generally be prepared using well known technology and administered by, for example, oral, rectal or subcutaneous implantation, or by implantation at the desired target site. Sustained-release formulations may contain a cyclic peptide dispersed in a carrier matrix and/or contained within a reservoir surrounded by a rate controlling membrane (see, e.g., European Patent Application 710,491 A). Carriers for use within such formulations are biocompatible, and may also be biodegradable; preferably the formulation provides a relatively constant level of cyclic peptide release. The amount of cyclic peptide contained within a sustained release formulation depends upon the site of implantation, the rate and expected duration of release and the nature of the condition to be treated or prevented.

Pharmaceutical compositions of the present invention may be administered in a manner appropriate to the disease to be treated (or prevented). Appropriate dosages and the duration and frequency of administration will be determined by such factors as the condition of the patient, the type and severity of the patient's disease and the method of administration. In general, an appropriate dosage and treatment regimen provides the modulating agent(s) in an amount sufficient to provide therapeutic and/or prophylactic benefit. Within particularly preferred embodiments of the invention, a modulating agent or pharmaceutical composition as described herein may be administered at a dosage ranging from 0.001 to 50 mg/kg body weight, preferably from 0.1 to 20 mg/kg, on a regimen of single or multiple daily doses. For topical administration, a cream typically comprises an amount of modulating agent ranging from 0.00001% to 1%, preferably 0.0001% to 0.2%, and more preferably from 0.0001% to 0.002%. Fluid compositions typically contain about 10 ng/ml to 5 mg/ml, preferably from about 10 μg to 2 mg/mL cyclic peptide. Appropriate dosages may generally be determined using experimental models and/or clinical trials. In general, the use of the minimum dosage that is sufficient to provide effective therapy is preferred. Patients may generally be monitored for therapeutic effectiveness using assays suitable for the condition being treated or prevented, which will be familiar to those of ordinary skill in the art.

Modulating Agent Methods of Use

In general, the modulating agents and compositions described herein may be used for inducing apoptosis in cadherin-expressing cells (i.e., cells that express one or more of E-cadherin, N-cadherin, P-cadherin, R-cadherin and/or other cadherin(s) containing the HAV sequence, including as yet undiscovered cadherins). It has been found, within the context of the present invention, that certain cancer cells express N-cadherin, and that modulating agents as described herein may be used to induce apoptosis of such cancer cells. Other cancer cells may express E-cadherin and/or one or more other classical cadherins. Accordingly, patients afflicted with cancer may benefit from such treatment.

Certain modulating agents comprise a cyclic peptide that has the formula:

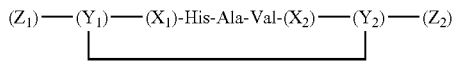

wherein $X_1$, and $X_2$ are optional, and if present, are independently selected from the group consisting of amino acid residues and combinations thereof in which the residues are linked by peptide bonds, and wherein $X_1$ and $X_2$ independently range in size from 0 to 10 residues, such that the sum of residues contained within $X_1$ and $X_2$ ranges from 1 to 12; wherein $Y_1$ and $Y_2$ are independently selected from the group consisting of amino acid residues, and wherein a covalent bond is formed between residues $Y_1$ and $Y_2$; and wherein $Z_1$ and $Z_2$ are optional, and if present, are independently selected from the group consisting of amino acid residues and combinations thereof in which the residues are linked by peptide bonds. Such cyclic peptides may comprise modifications such as an N-acetyl or N-alkoxybenzyl group and/or a C-terminal amide or ester group.

Certain preferred modulating agents comprise a cyclic peptide having the formula:

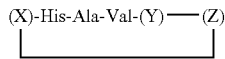

wherein Y is optional and, if present is selected from the group consisting of amino acid residues and combinations thereof in which the residues are linked by peptide bonds, and wherein Y ranges in size from 0 to 10 residues; and wherein X and Z are independently selected from the group consisting of amino acid residues, wherein a disulfide bond is formed between residues X and Z; and wherein X comprises an N-acetyl group.

Preferred modulating agents for use within such methods comprise a cyclic peptide such as N-Ac-CHAVC-NH$_2$ (SEQ ID NO:10), N-Ac-CAHVDC-NH$_2$ (SEQ ID NO:11), N-Ac-CAHVDIC-NH$_2$ (SEQ ID NO:62), N-Ac-CAHVDINC-NH$_2$ (SEQ ID NO:63), N-Ac-CHAVDINGC-NH$_2$ (SEQ ID NO:70), N-Ac-CAHAVC-NH$_2$ (SEQ ID NO:12), N-Ac-CAHAVDC-NH$_2$ (SEQ ID NO:13), N-Ac-CAHAVDIC-NH$_2$ (SEQ ID NO:14), N-Ac-CRAHAVDC-NH$_2$ (SEQ ID NO:15), N-Ac-CLRAHAVC-NH$_2$ (SEQ ID NO:43), N-Ac-CLRAHAVDC-NH$_2$ (SEQ ID NO:16), N-Ac-CSHAVC-NH$_2$ (SEQ ID NO:26), N-Ac-CAHVSC-NH$_2$ (SEQ ID NO:27), N-Ac-CSHAVSC-NH$_2$ (SEQ ID NO:49), N-Ac-CSHAVSSC-NH$_2$ (SEQ ID NO:28), N-Ac-CHAVSSC-NH$_2$ (SEQ ID NO:52), N-Ac-KHAVD-NH$_2$ (SEQ ID NO:37), N-Ac-DHAVK-NH$_2$ (SEQ ID NO:17), N-Ac-KHAVE-NH$_2$ (SEQ ID NO:18), N-Ac-AHAVDI-NH$_2$ (SEQ ID NO:19), N-Ac-SHAVDSS-NH$_2$ (SEQ ID NO:78), N-Ac-KSHAVSSD-NH$_2$ (SEQ ID NO:60) and derivatives thereof, including derivatives without the N-acetyl group. Modulating agents comprising a CAR sequence for a second adhesion molecule (e.g., RGD, LYHY (SEQ ID NO:64), or a CAR sequence for OB-cadherin, dsc or dsg) are also preferred. Alternatively, a separate modulator of cell adhesion mediated by an adhesion molecule that is not a cadherin may be administered in conjunction with the modulating agent(s), either within the same pharmaceutical composition or separately. Administration may be topical, via injection or by other means, and the addition of a targeting agent may be beneficial, particularly when the administration is systemic. Suitable modes of administration and dosages depend upon the location and nature of the cells for which induction of apoptosis is desired but, in general, dosages may vary as described above. A biopsy may be performed to evaluate the level of induction of apoptosis.

The following Examples are offered by way of illustration and not by way of limitation.

EXAMPLE 1

Preparation of Representative Cyclic Peptides

This Example illustrates the solid phase synthesis of representative cyclic peptides.

The peptides were assembled on methylbenzhydrylamine resin (MBHA resin) for the C-terminal amide peptides. The traditional Merrifield resins were used for any C-terminal acid peptides. Bags of a polypropylene mesh material were filled with the resin and soaked in dichloromethane. The resin packets were washed three times with 5% diisopropylethylamine in dichloromethane and then washed with dichloromethane. The packets are then sorted and placed into a Nalgene bottle containing a solution of the amino acid of interest in dichloromethane. An equal amount of diisopropylcarbodiimide (DIC) in dichloromethane was added to activate the coupling reaction. The bottle was shaken for one hour to ensure completion of the reaction. The reaction mixture was discarded and the packets washed with DMF. The N-α-Boc was removed by acidolysis using a 55% TFA in dichloromethane for 30 minutes leaving the TFA salt of the α-amino group. The bags were washed and the synthesis completed by repeating the same procedure while substituting for the corresponding amino acid at the coupling step. Acetylation of the N-terminal was performed by reacting the peptide resins with a solution of acetic anhydride in dichloromethane in the presence of diisopropylethylamine. The peptide was then side-chain deprotected and cleaved from the resin at 0° C. with liquid HF in the presence of anisole as a carbocation scavenger.

The crude peptides were purified by reversed-phase high-performance liquid chromatography. Purified linear precursors of the cyclic peptides were solubilized in 75% acetic acid at a concentration of 2–10 mg/mL. A 10% solution of iodine in methanol was added dropwise until a persistent coloration was obtained. A 5% ascorbic acid solution in water was then added to the mixture until discoloration. The disulfide bridge containing compounds were then purified by HPLC and characterized by analytical HPLC and by mass spectral analysis.

EXAMPLE 2

Disruption of the Ability of Mouse Cerebellar Neurons to Extend Neurites

Three cell adhesion molecules, N-cadherin, N-CAM and L1, are capable of regulating neurite outgrowth (Doherty and Walsh, *Curr. Op. Neurobiol.* 4:49–55, 1994; Williams et al., *Neuron* 13:583–594, 1994; Hall et al., *Cell Adhesion and Commun.* 3:441–450, 1996; Doherty and Walsh, *Mol. Cell.*

Neurosci. 8:99–111, 1994; Safell et al., Neuron 18:231–242, 1997). Neurons cultured on monolayers of 3T3 cells that have been transfected with cDNAs encoding N-cadherin, N-CAM or L1 extend longer neurites than neurons cultured on 3T3 cells not expressing these cell adhesion molecules. This Example illustrates the use of a representative cyclic peptide to inhibit neurite outgrowth.

Neurons were cultured on monolayers of 3T3 cells transfected with cDNA encoding N-cadherin essentially as described by Doherty and Walsh, Curr. Op. Neurobiol. 4:49–55, 1994; Williams et al., Neuron 13:583–594, 1994; Hall et al., Cell Adhesion and Commun. 3:441–450, 1996; Doherty and Walsh, Mol. Cell. Neurosci. 8:99–111, 1994; Safell et al., Neuron 18:231–242, 1997. Briefly, monolayers of control 3T3 fibroblasts and 3T3 fibroblasts that express N-cadherin were established by overnight culture of 80,000 cells in individual wells of an 8-chamber well tissue culture slide. 3000 cerebellar neurons isolated from post-natal day 3 mouse brains were cultured for 18 hours on the various monolayers in control media (SATO/2% FCS), or media supplemented with various concentrations of the cyclic peptide N-Ac-CHAVC-NH$_2$ (SEQ ID NO:10) or a control peptide without the HAV sequence (N-Ac-CHGVC-NH$_2$ (SEQ ID NO:20)). The cultures were then fixed and stained for GAP43 which specifically binds to the neurons and their neurites. The length of the longest neurite on each GAP43 positive neuron was then measured by computer assisted morphometry.

Figure 4:
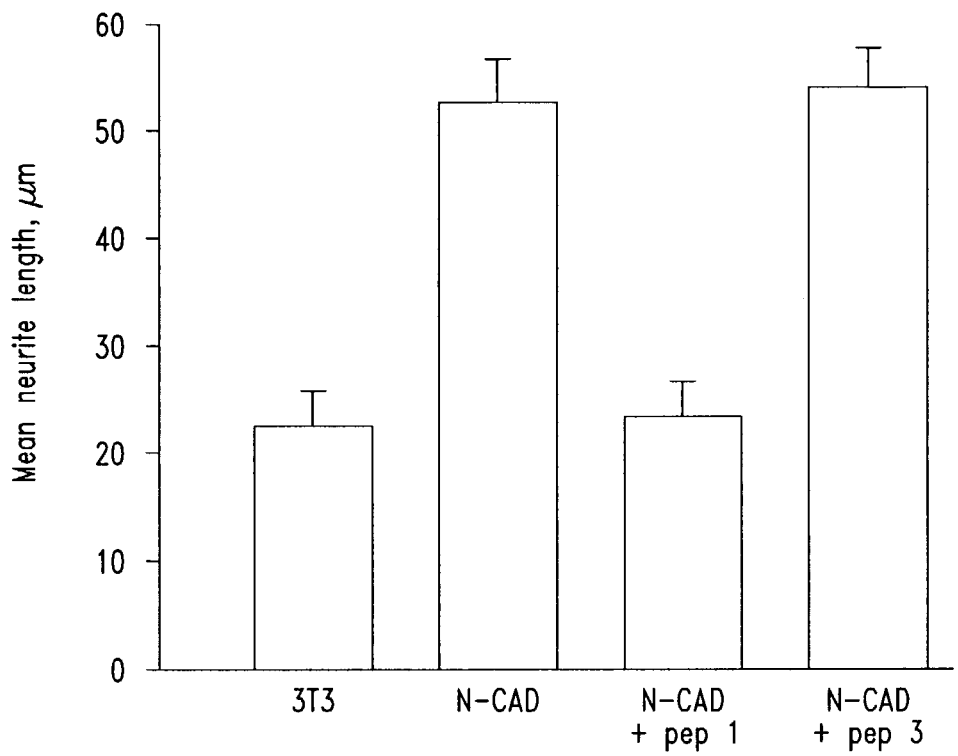
FIG. 4 is a histogram depicting the mean neurite length in microns for neurons grown on a monolayer of untransfected 3T3 cells (first column) or 3T3 cells transfected with cDNA encoding N-cadherin (columns 2–4). In the third column, the mean neurite length in the presence of the representative cyclic peptide N-Ac-CHAVC-NH$_2$ (SEQ ID NO:10) is shown. Column 4 depicts the mean neurite length in the presence of the control peptide N-Ac-CHGVC-NH$_2$ (SEQ ID NO:20).

As shown in FIG. 4, culture for 18 hours with N-Ac-CHAVC-NH$_2$ (SEQ ID NO:10) at a concentration of 500 µg/mL inhibited neurite outgrowth on 3T3 cells expressing N-cadherin, whereas the cyclic peptide N-Ac-CHGVC-NH$_2$ (SEQ ID NO:20; also at a concentration of 500 µg/ml) had no effect on this process. Furthermore, the cyclic peptide N-Ac-CHAVC-NH$_2$ (SEQ ID NO:10; used at a concentration of 500 µg/ml) did not inhibit neurite outgrowth on 3T3 cells not expressing N-cadherin, N-CAM, or L1 (control cells), thus indicating that the peptide is not toxic and that it has no non-specific effects on neurite outgrowth (FIG. 4, compare columns 3 and 1). These data also indicate that the peptide does not effect integrin function.

Figure 5:
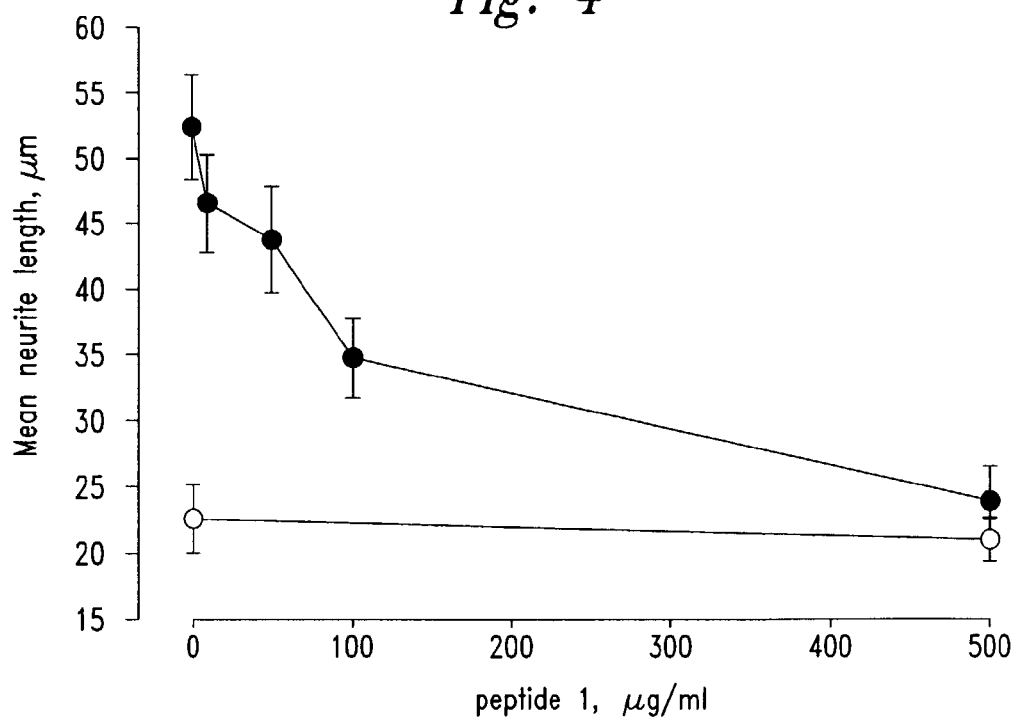
FIG. 5 is a graph showing a dose response curve for the representative cyclic peptide N-Ac-CHAVC-NH$_2$ (SEQ ID NO:10) on control 3T3 cells (open circles) and on 3T3 cells expressing N-cadherin (solid circles).
Figure 6:
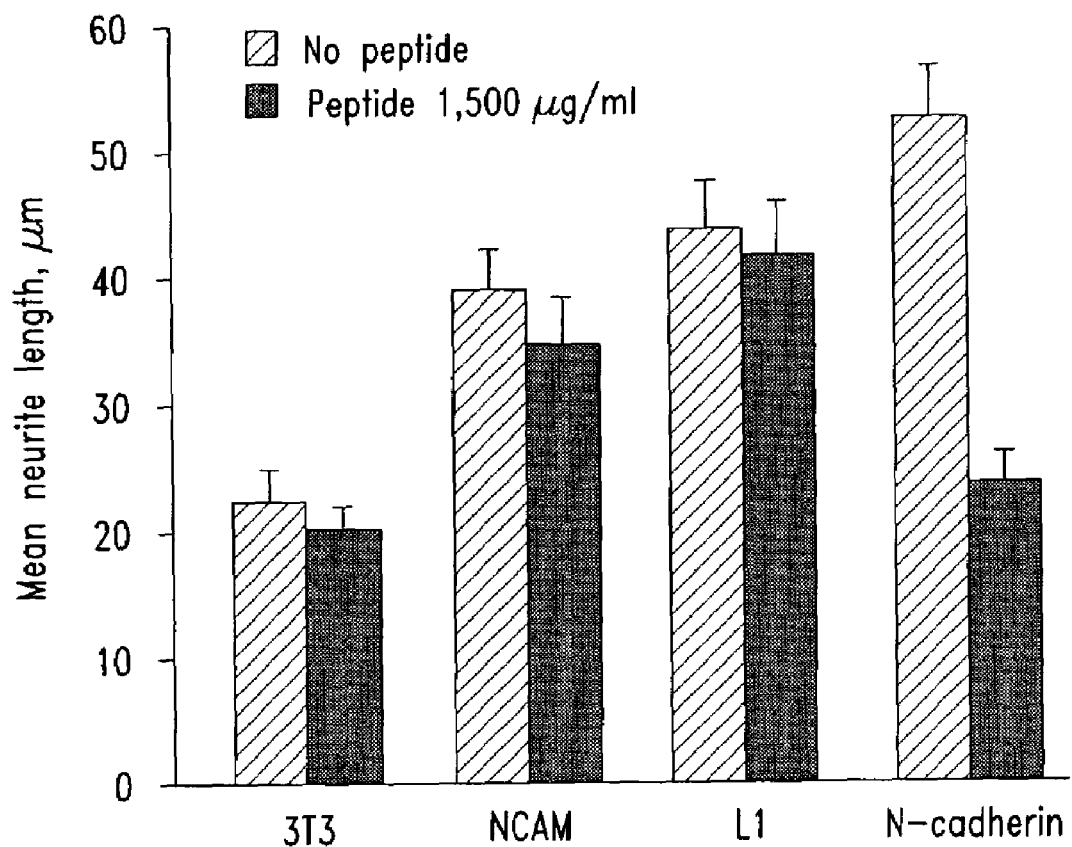
FIG. 6 is a histogram depicting the mean neurite length in microns for neurons grown in the presence (solid bars) or absence (cross-hatched bars) of 500 μg/mL of the representative cyclic peptide N-Ac-CHAVC-NH$_2$ (SEQ ID NO:10). In the first pair of bars, neurons were grown on a monolayer of untransfected 3T3 cells. In the remaining columns, the mean neurite length is shown for neurons cultured on 3T3 cells transfected with cDNA encoding N-CAM (second pair of bars), L1 (third pair of bars) or N-cadherin (fourth pair of bars).

A dose-response study demonstrated that N-Ac-CHAVC-NH$_2$ (SEQ ID NO:10) significantly inhibited neurite outgrowth on 3T3 cells expressing N-cadherin at a concentration of 50 µg/mL, and completely inhibited neurite outgrowth on these cells at a concentration of 500 µg/mL (FIG. 5). Finally, N-Ac-CHAVC-NH$_2$ (SEQ ID NO:10; used at a concentration of 500 µg/mL) did not inhibit neurite outgrowth on 3T3 cells expressing either N-CAM or L1 (FIG. 6). These results indicate that the peptide N-Ac-CHAVC-NH$_2$ (SEQ ID NO:10) specifically inhibits the function of N-cadherin. Collectively, the results obtained from these studies demonstrate that N-Ac-CHAVC-NH$_2$ (SEQ ID NO:10) is an effective inhibitor of neurite outgrowth by virtue of its ability to disrupt N-cadherin function.

EXAMPLE 3

Disruption of Bovine Endothelial Cell Adhesion

This Example illustrates the use of representative cyclic peptides to disrupt adhesion of endothelial cells, which express N-cadherin.

Bovine pulmonary artery endothelial cells were harvested by sterile ablation and digestion in 0.1% collagenase (type II; Worthington Enzymes, Freehold, N.J.). Cells were maintained in Dulbecco's minimum essential medium (Clonetics, San Diego, Calif.) supplemented with 10% fetal calf serum (Atlantic Biologicals, Nor cross, Ga.) and 1% antibiotic-antimycotic at 37° C. in 7% CO$_2$ in air. Cultures were passaged weekly in trypsin-EDTA (Gibco, Grand Island, N.Y.) and seeded onto tissue culture plastic at 20,000 cells/cm$^2$ for all experiments. Endothelial cultures were used at 1 week in culture, which is approximately 3 days after culture confluency was established. The cells used in all protocols were between 4th passage and 10th passage. The cells were seeded onto coverslips and treated 30 minutes with N-Ac-CHAVC-NH$_2$ (SEQ ID NO:10) or N-Ac-CHGVC-NH$_2$ (SEQ ID NO:20) at 500 µg/ml and then fixed with 1% paraformaldehyde.

Figure 7A:
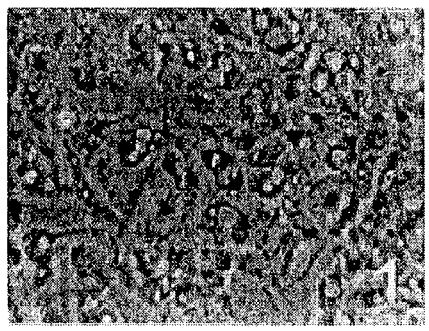
FIGS. 7A–7C are photographs showing monolayer cultures of bovine endothelial cells in the presence (FIG. 7A) and absence (FIG. 7C) of a representative cyclic peptide or in the presence of an inactive control peptide (FIG. 7B).
Figure 7B:
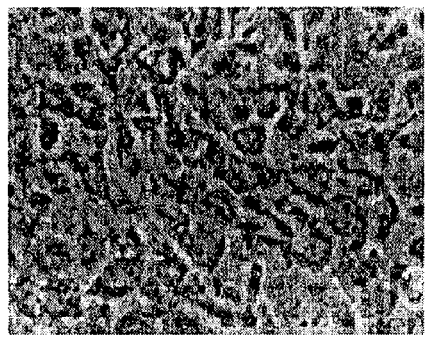
Figure 7C:
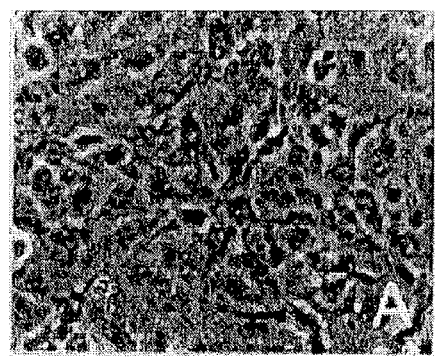

The peptide N-Ac-CHAVC-NH$_2$ (SEQ ID NO:10) disrupted the endothelial cell monolayer within 30 minutes after being added to the culture medium, whereas N-Ac-CHGVC-NH$_2$ (SEQ ID NO:20) had no affect on the cells (FIG. 7). Endothelial cell morphology was dramatically affected by N-Ac-CHAVC-NH$_2$ (SEQ ID NO:10), and the cells retracted from one another and became non-adherent. These data demonstrate that N-Ac-CHAVC-NH$_2$ (SEQ ID NO:10) is capable of inhibiting endothelial cell adhesion.

Figure 8A:
FIGS. 8A–8C are photographs showing monolayer cultures of bovine endothelial cells in the presence (FIG. 8A) and absence (FIG. 8C) of a representative cyclic peptide or in the presence of an inactive control peptide (FIG. 8B).
Figure 8B:
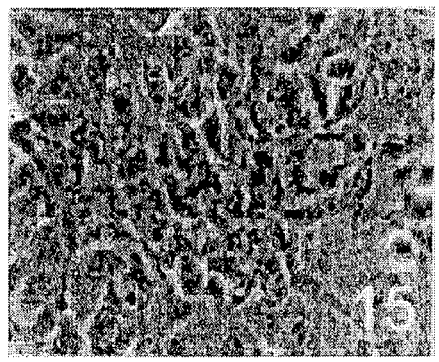
Figure 8C:
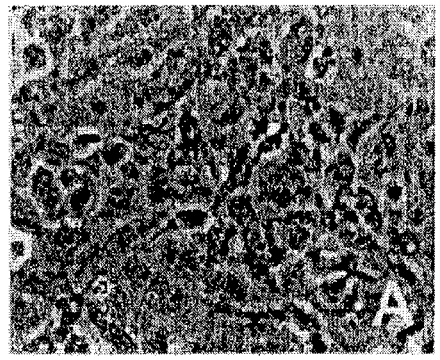
Figure 9A:
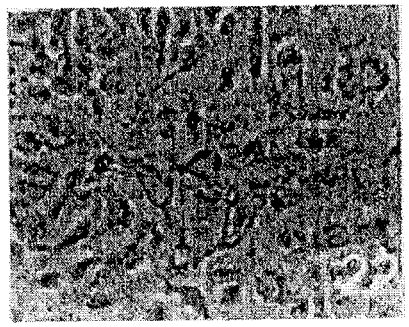
FIGS. 9A–9C are photographs showing monolayer cultures of bovine endothelial cells in the presence (FIG. 9A) and absence (FIG. 9C) of a representative cyclic peptide or in the presence of an inactive control peptide (FIG. 9B).
Figure 10A:
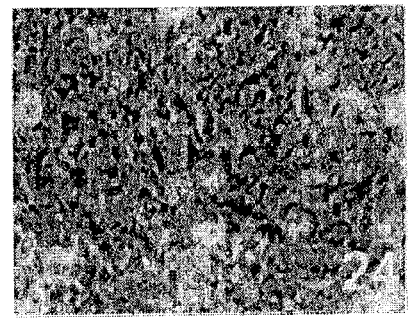
FIGS. 10A–10C are photographs showing monolayer cultures of bovine endothelial cells in the presence (FIG. 10A) and absence (FIG. 10C) of a representative cyclic peptide or in the presence of an inactive control peptide (FIG. 10B).
Figure 9B:
Figure 10B:
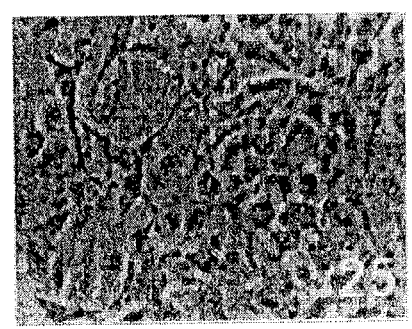
Figure 9C:
Figure 10C:
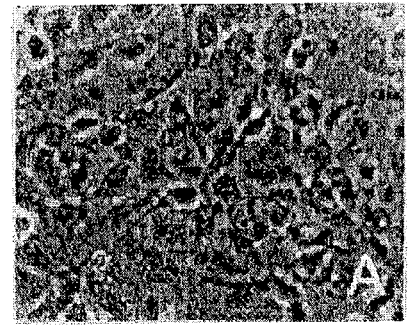

Under the same conditions, the cyclic peptides H-CHAVC-NH$_2$ (SEQ ID NO:10), N-Ac-CAHAVDIC-NH$_2$ (SEQ ID NO:14) (FIG. 8) and N-Ac-CAHVSC-NH$_2$ (SEQ ID NO:27) had no effect on endothelial cell morphology, indicating that not all cyclic HAV-containing peptides are capable of disrupting endothelial cell adhesion at a concentration of 500 µg/mL. It is not unexpected that the potencies of individual cyclic peptides will vary The cyclic peptide N-Ac-CAHAVDC-NH$_2$ (SEQ ID NO:13; FIG. 9) had a slight effect while N-Ac-CSHAVSSC-NH$_2$ (SEQ ID NO:28; FIG. 10) disrupted the endothelial cell monolayer and caused the cells to retract from one another.

EXAMPLE 4

Disruption of Human Ovarian Cancer Cell Adhesion

This Example illustrates the use of a representative cyclic peptide to disrupt adhesion of human ovarian cancer cells.

The human ovarian cancer cell line SKOV3 (ATCC #HTB-77) expresses N-cadherin. SKOV3 cells were cultured in a modified MEM-based media containing 10% FCS. Cells were grown in T-250 culture flasks and maintained by periodic subculturing. Cyclic peptides were tested on cells grown in individual wells of 96-well culture dishes (surface area of each well was 0.32 cm$^2$). Cells were harvested from flasks and seeded at a density of 50,000 cells per well in 0.1 mL media containing the cyclic peptides at concentrations of 1, 0.1, or 0.01 mg/mL, or in the absence of cyclic peptide. Media control wells were also established. Cultures were evaluated periodically by microscopic examination under both bright field and phase contrast conditions. Cultures were maintained for 48 hours.

Figure 11A:
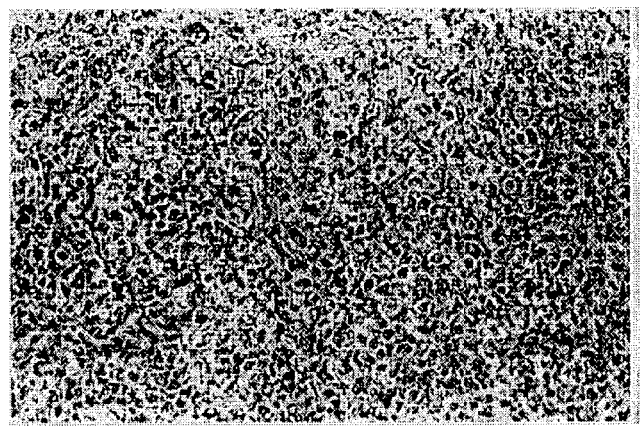
FIGS. 11A–11F are photographs showing monolayer cultures of human ovarian cancer cells (SKOV3) in the presence (FIGS. 11A and D–F) and absence (FIG. 11C) of a representative cyclic peptide or in the presence of an inactive control peptide (FIG. 11B).
Figure 11B:
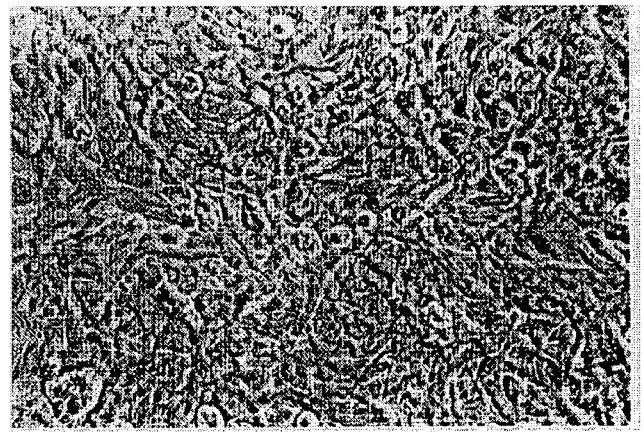
Figure 11C:
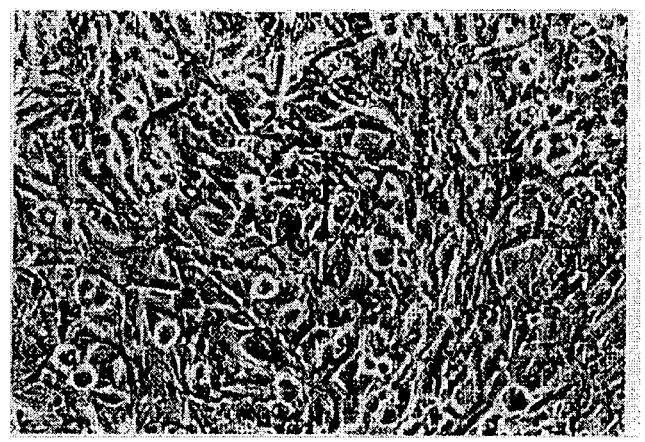
Figure 11D:
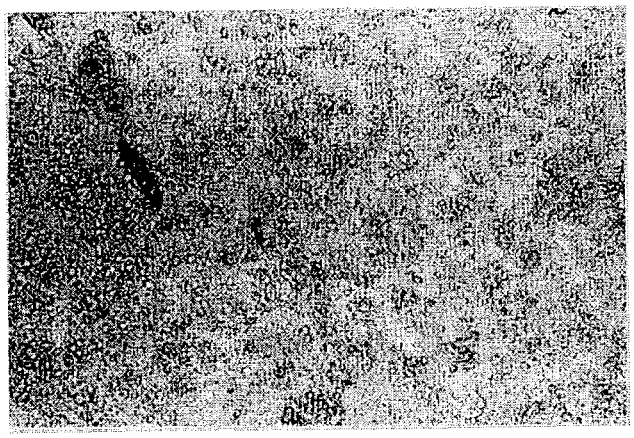
Figure 11E:
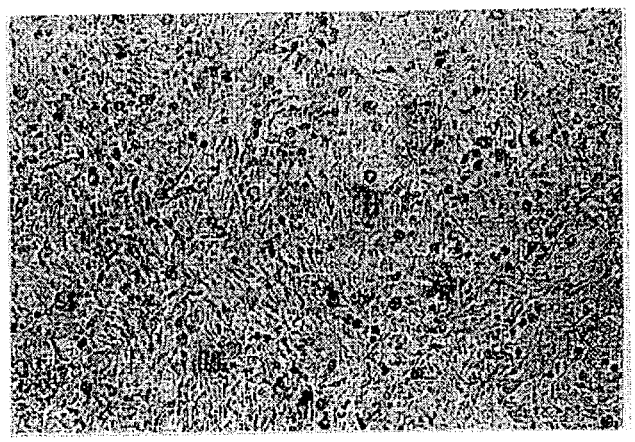
Figure 11F:
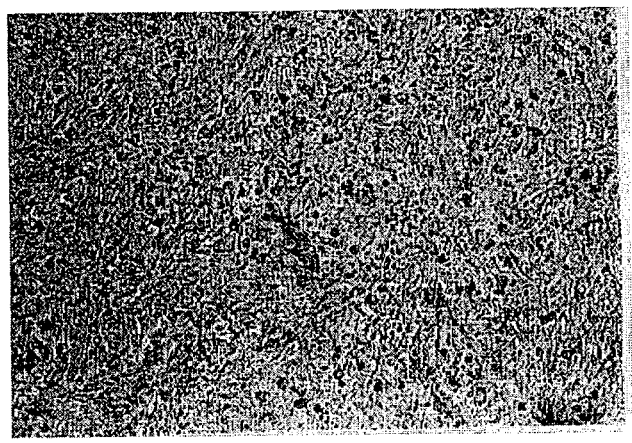
Figure 12A:
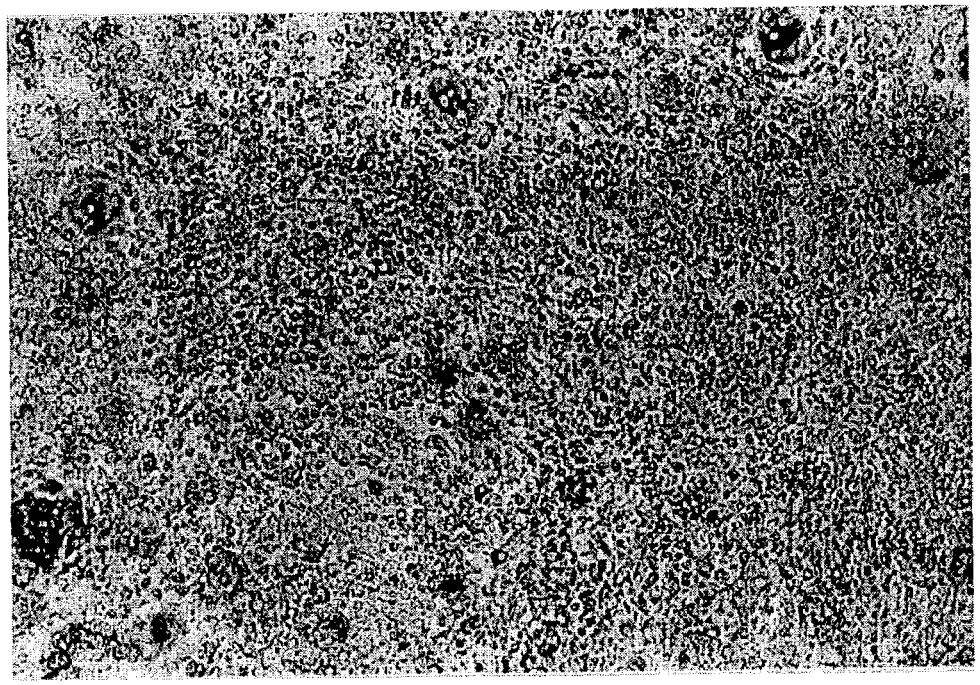
FIGS. 12A and 12B are photographs showing monolayer cultures of human ovarian cancer cells (SKOV3) 24 hours after exposure to 500 μg/mL of the representative cyclic peptide N-Ac-CHAVC-NH$_2$ (SEQ ID NO:10) (FIG. 12A) or the control peptide N-Ac-CHGVC-NH$_2$ (SEQ ID NO:20) (FIG. 12B). Note that the SKOV3 cells round-up when cultured in the presence of 0.5 mg/ml N-Ac-CHAVC-NH$_2$ (SEQ ID NO:10).
Figure 12B:
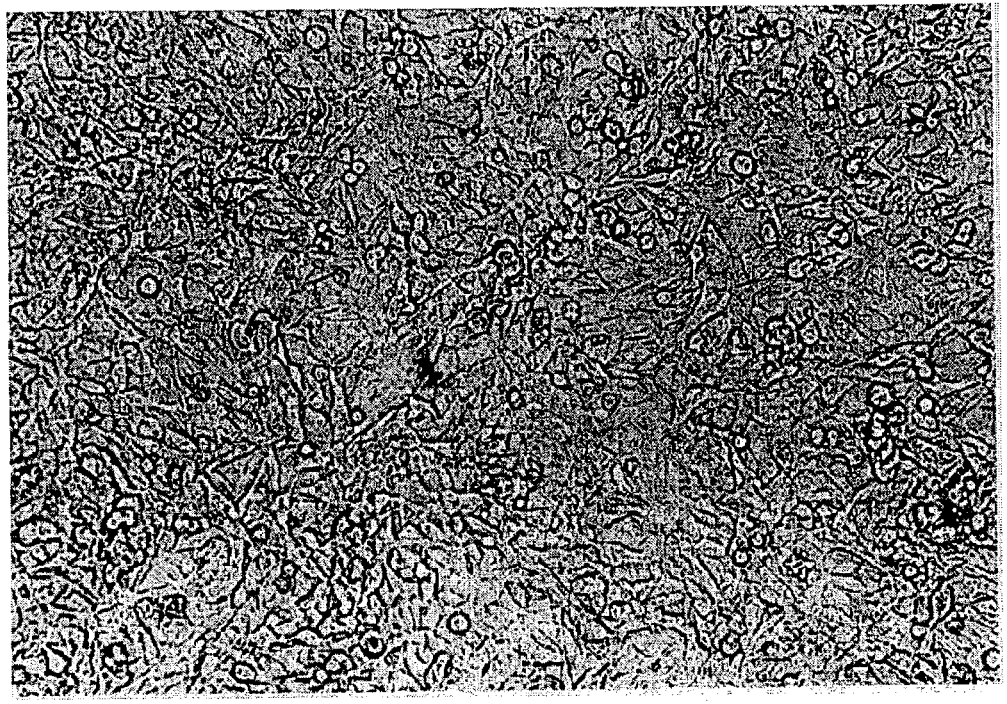

As shown in FIGS. 11A (compare to FIG. 11C) and 12A, the peptide N-Ac-CHAVC-NH$_2$ (SEQ ID NO:10; final concentration of 1 mg/mL media) disrupted SKOV3 cell adhesion within 24 hours, whereas the control N-Ac-CHGVC-NH$_2$ (SEQ ID NO:20) had no affect on cell adhesion (FIGS. 11B and 12B). The effect of different amounts of N-Ac-CHAVC-NH$_2$ (SEQ ID NO:10) after 48 hours is shown in FIGS. 11D–F. In the presence of N-Ac-CHGVC-NH$_2$, (SEQ ID NO:20; FIGS. 11B and 12B) the SKOV3 cells formed tightly adherent monolayers. In contrast, the SKOV3 cells did not spread onto the substrata, nor did they form tightly adherent monolayers in the presence of N-Ac-CHAVC-NH$_2$ (SEQ ID NO:10; FIGS. 11A, D and 12A). These data demonstrate that N-Ac-CHAVC-NH$_2$ (SEQ ID NO:10) is capable of inhibiting the function of human N-cadherin.

The cyclic peptides N-Ac-CAHAVDIC-NH$_2$ (SEQ ID NO:14), N-Ac-CAHAVDC-NH$_2$ (SEQ ID NO:13) and N-Ac-KHAVD-NH, (SEQ ID NO:37) were inactive in the SKOV3 cells, indicating that not all cyclic HAV-containing peptides are capable of disrupting epithelial cell adhesion at concentrations of 0.01–1 mg/mL It is not unexpected that the potencies of the cyclic peptides will vary.

EXAMPLE 5

Disruption of Angiogenesis

Blood vessels are composed of adherent endothelial cells. This Example illustrates the use of a representative cyclic peptide to block angiogenesis (the growth of blood vessels from pre-existing blood vessels).

The chick chorioallantoic membrane assay was used to assess the effects of cyclic peptides on angiogenesis (Iruela-Arispe et al., *Molecular Biology of the Cell* 6:327–343, 1995). Cyclic peptides were embedded in a mesh composed of vitrogen at concentrations of 3, 17, and 33 µg/mesh. The meshes were then applied to 12-day-old chick embryonic chorioallantoic membranes. After 24 hours, the effects of the peptides on angiogenesis were assessed by computer assisted morphometric analysis.

The ability of representative cyclic peptides to inhibit angiogenesis is illustrated by the results presented in Table 2. For each concentration of cyclic peptide, the percent inhibition of angiogenesis (relative to the level of angiogenesis in the absence of cyclic peptide) is provided. Assays were performed in the presence (+) or absence (−) of 0.01 mM VEGF. For example, the cyclic peptide N-Ac-CHAVC-NH$_2$ (SEQ ID NO:10) inhibited angiogenesis by 46%, 51%, and 51% at concentrations of 3, 17, and 33 µg/mesh, respectively. The N-cadherin selective peptides N-Ac-CAHAVDIC-NH$_2$ (SEQ ID NO:14) and N-Ac-CAHAVDC-NH$_2$ (SEQ ID NO:13) also inhibited angiogenesis significantly. The E-cadherin selective cyclic peptides N-Ac-CAHVSC-NH$_2$ (SEQ ID NO:27) and N-Ac-CSHAVSSC-NH$_2$ (SEQ ID NO:28), as well as the scrambled peptide N-Ac-CVAHC-NH$_2$ (SEQ ID NO:54), were found to be relatively inactive in this assay.

TABLE 2

| Compound | Concentration, µg/mesh ± VEGF | | | | | |
|---|---|---|---|---|---|---|
| | 3(−) | 3(+) | 17(−) | 17(+) | 33(−) | 33(+) |
| H-CHAVC-NH$_2$ (SEQ ID NO:10) | 11% | 27% | 13% | 34% | 17% | 35% |
| N-Ac-CHAVSC-NH$_2$ (SEQ ID NO:27) | 11% | 17% | 12% | 16% | 17% | 19% |
| N-Ac-CVAHC-NH$_2$ (SEQ ID NO:54) | −1% | 7% | 13% | 24% | 12% | 25% |
| N-Ac-CHAVC-NH$_2$ (SEQ ID NO:10) | 12% | 46% | 22% | 51% | 28% | 51% |

TABLE 2-continued

| Compound | Concentration, µg/mesh ± VEGF | | | | | |
|---|---|---|---|---|---|---|
| | 3(−) | 3(+) | 17(−) | 17(+) | 33(−) | 33(+) |
| N-Ac-CAHAVDIC-NH$_2$ (SEQ ID NO:14) | −1% | 21% | 15% | 37% | 33% | 49% |
| N-Ac-CAHAVDC-NH$_2$ (SEQ ID NO:13) | 21% | 59% | 27% | 72% | 31% | 79% |
| N-Ac-CSHAVSSC-NH$_2$ (SEQ ID NO:28) | 1% | −3% | −3% | 12% | 17% | 7% |

EXAMPLE 6

Disruption of Normal Rat Kidney (NRK) Cell Adhesion

NRK cells express E-cadherin, and monolayer cultures of these cells exhibit a cobblestone morphology. This Example illustrates the ability of a representative cyclic peptide to disrupt NRK cell adhesion.

NRK cells (ATCC #1571-CRL) were plated at 10–20,000 cells per 35 mm tissue culture flasks containing DMEM with 10% FCS and sub-cultured periodically (Laird et al., *J. Cell Biol.* 131:1193–1203, 1995). Cells were harvested and replated in 35 mm tissue culture flasks containing 1 mm coverslips and incubated until 50–65% confluent (24–36 hours). At this time, coverslips were transferred to a 24-well plate, washed once with fresh DMEM and exposed to cyclic peptide solutions (N-Ac-CHAVC-NH$_2$ (SEQ ID NO:10) and N-Ac-CHGVC-NH$_2$ (SEQ ID NO:20)) at a concentration of 1 mg/mL for 24 hours. Fresh peptide solutions were then added and the cells were left for an additional 24 hours. Cells were fixed with 100% methanol for 10 minutes and then washed three times with PBS. Coverslips were blocked for 1 hour in 2% BSA/PBS and incubated for a further 1 hour in the presence of mouse anti-E-cadherin antibody (Transduction Labs, Lexington, Ky.; 1:250 dilution). Primary and secondary antibodies were diluted in 2% BSA/PBS. Following incubation in the primary antibody, coverslips were washed three times for 5 minutes each in PBS and incubated for 1 hour with donkey anti-mouse antibody conjugated to fluorescein (Jackson Immuno Research, West Grove, Pa.; diluted 1:200). Following a further wash in PBS (3×5 min) coverslips were mounted and viewed by confocal microscopy.

Figure 13A:
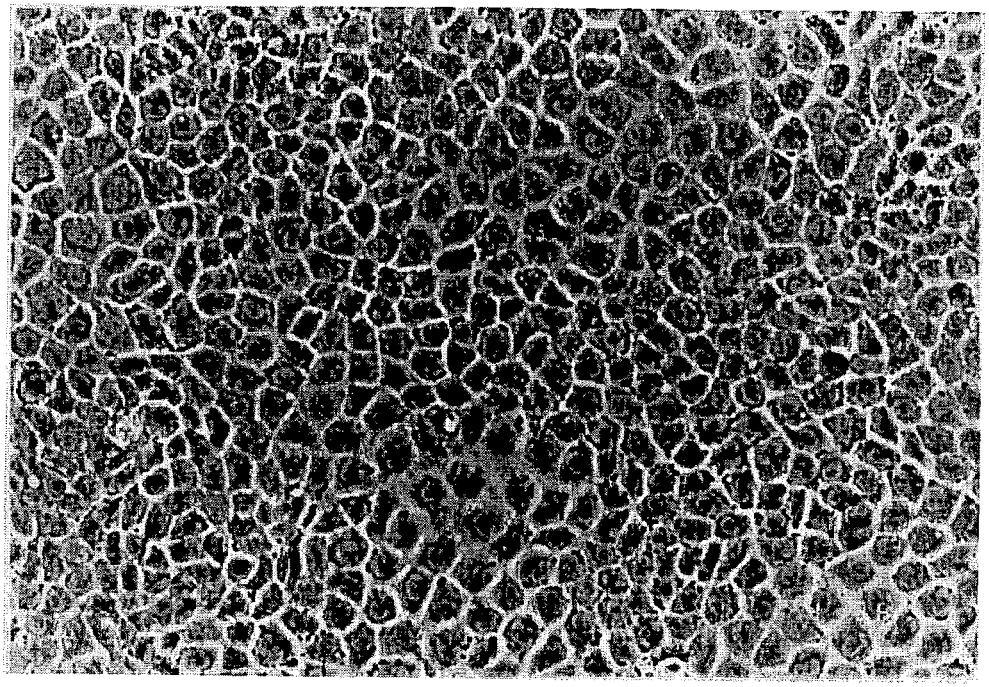
FIGS. 13A–13D are photographs of monolayer cultures of normal rat kidney (NRK) cells untreated (FIG. 13A) or after 48 hours of exposure to 1 mg/mL H-CHAVSC-OH (SEQ ID NO:27) (FIG. 13B), the control peptide N-Ac-CHGVC-NH$_2$ (SEQ ID NO:20), (FIG. 13C) or the representative cyclic peptide N-Ac-CHAVC-NH$_2$ (SEQ ID NO:10), (FIG. 13D). Note that NRK cells retract from one another when cultured in the presence of N-Ac-CHAVC-NH$_2$ (SEQ ID NO:10). Furthermore the NRK cells do not form cobblestone-like monolayers when exposed to this peptide.
Figure 13B:
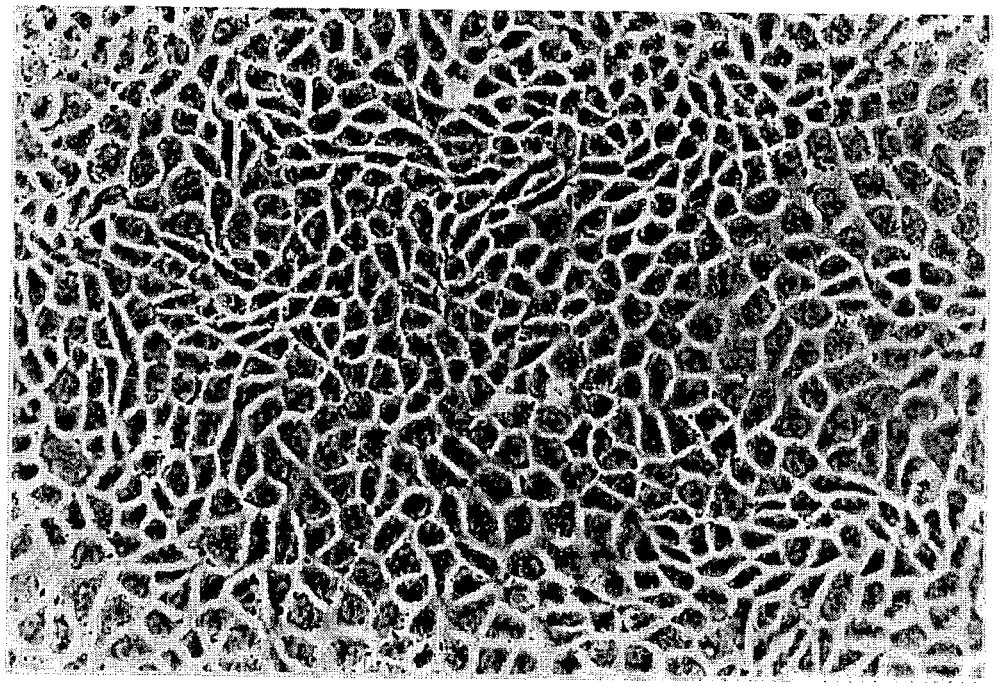
Figure 13C:
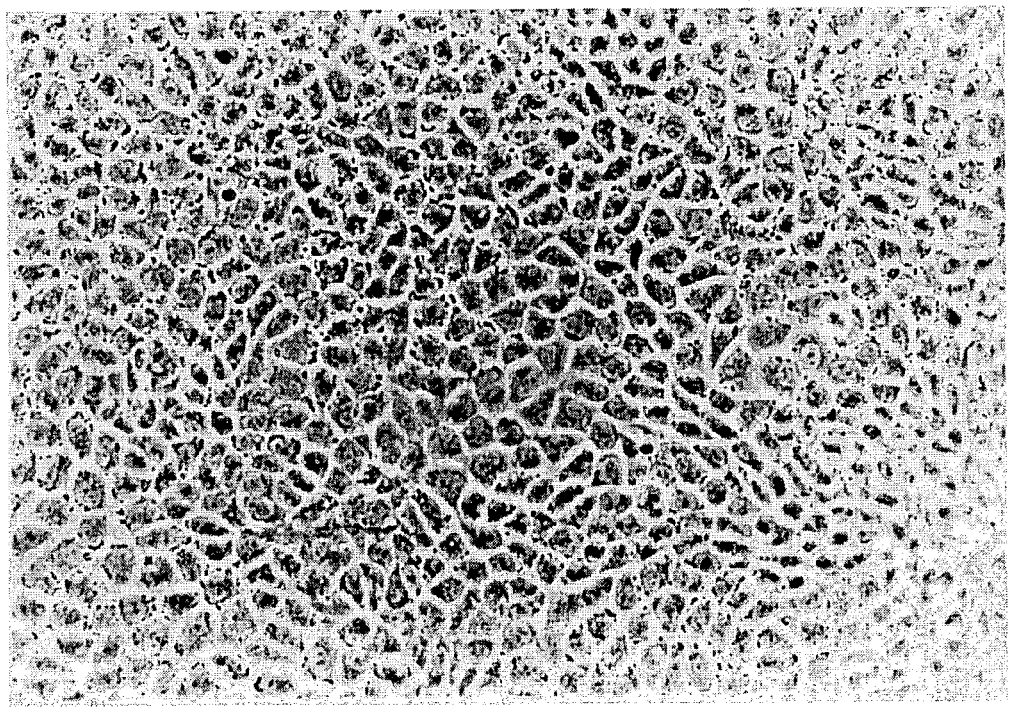
Figure 13D:
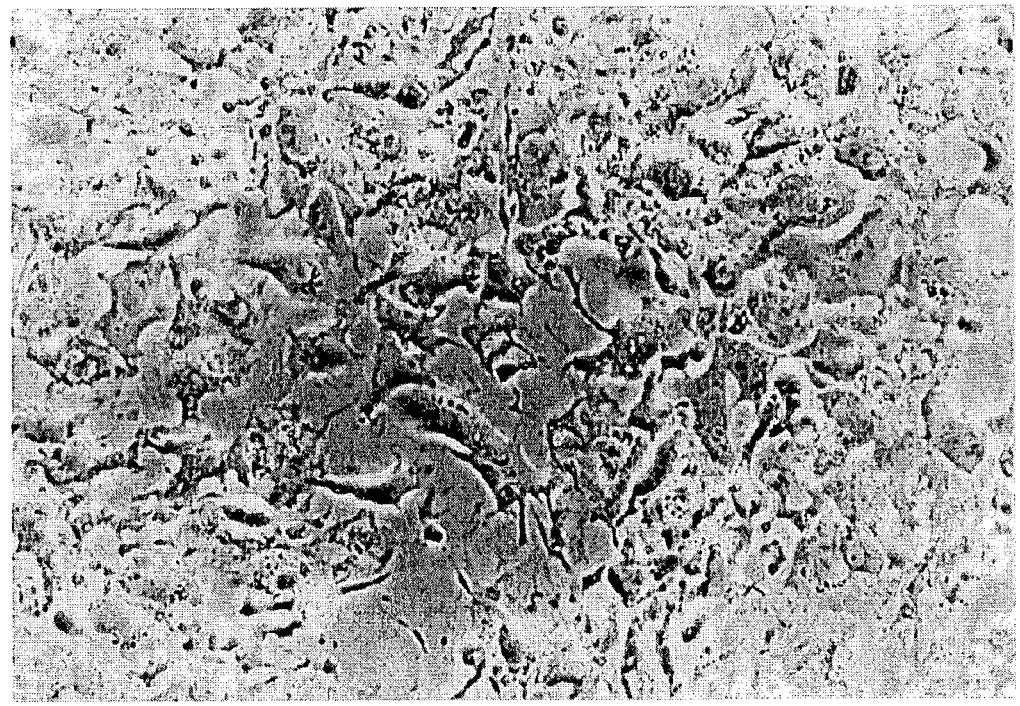
Figure 14A:
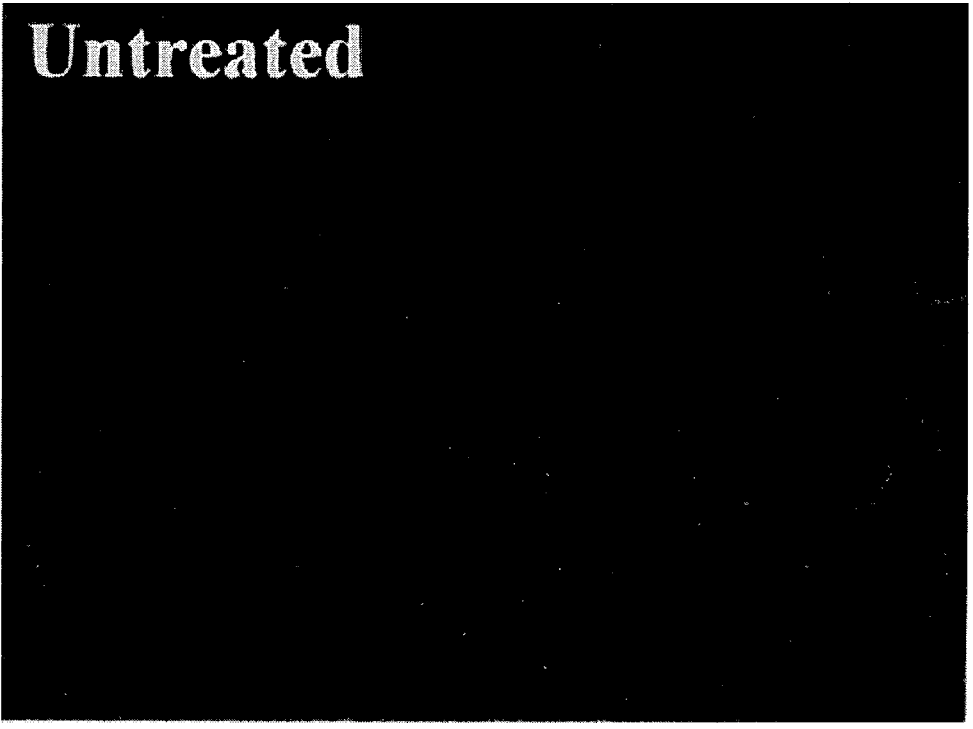
FIGS. 14A–14D are immunofluorescence photographs of the monolayer normal rat kidney (NRK) cultures shown in FIGS. 13A–D immunolabeled for E-cadherin.
Figure 14B:
Figure 14C:
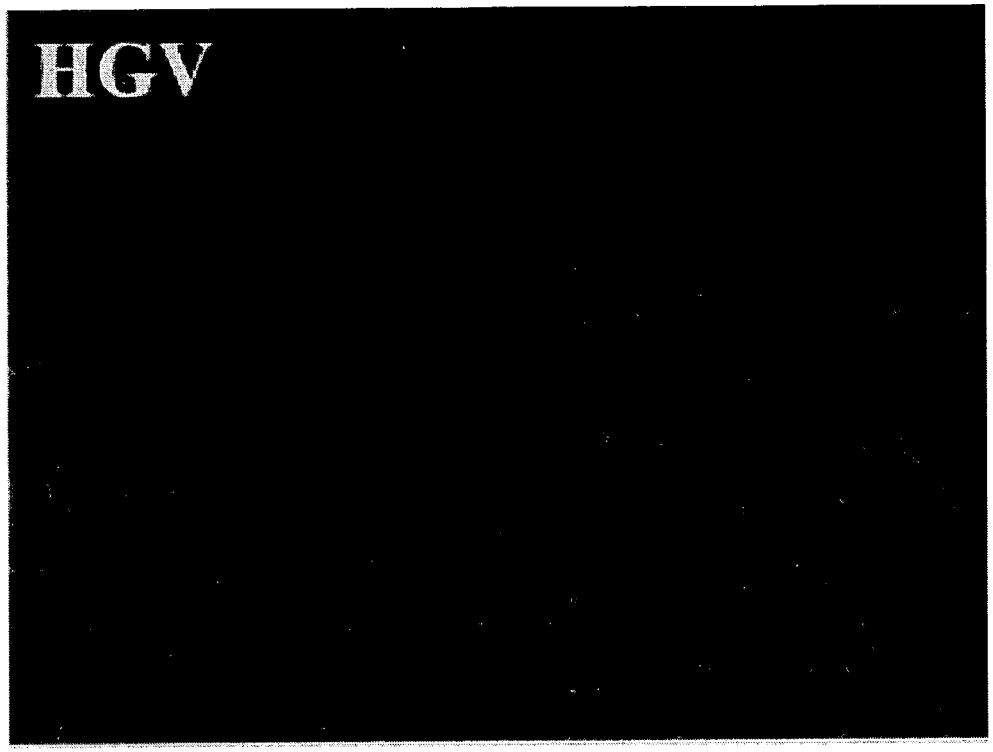
Figure 14D:
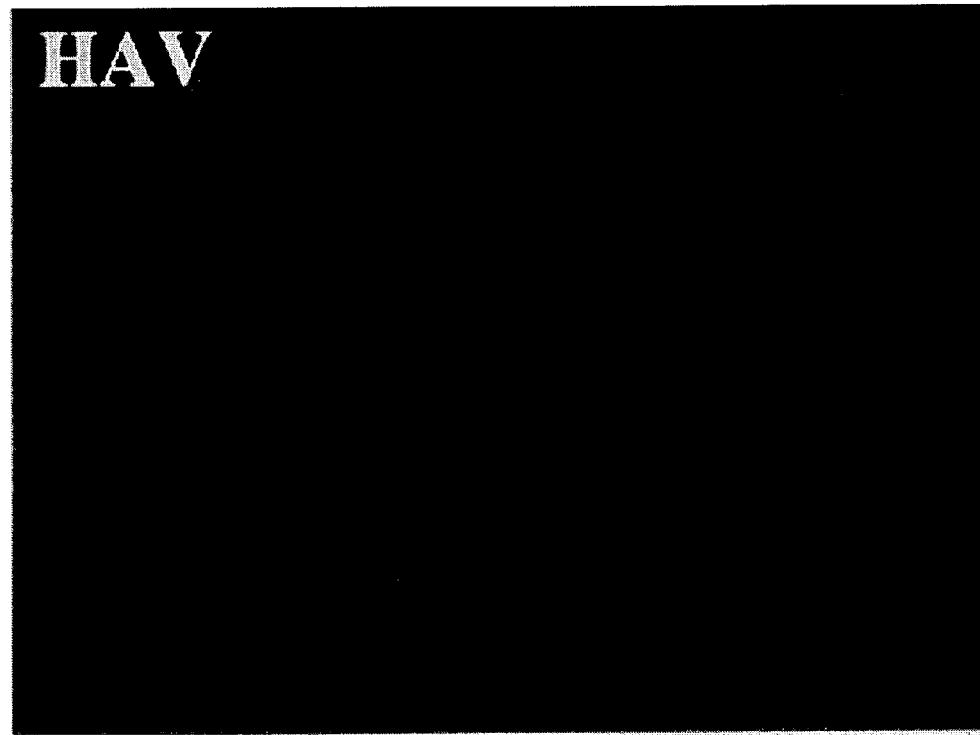

The peptide N-Ac-CHAVC-NH$_2$ (SEQ ID NO:10) disrupted NRK cell adhesion FIG. 13D, compare to 13A), whereas N-Ac-CHGVC-NH$_2$ (SEQ ID NO:20) had no affect on cell adhesion (FIG. 13C). In the presence of N-Ac-CHGVC-NH$_2$ (SEQ ID NO:20), the NRK cells formed tightly adherent monolayers with a cobblestone morphology. They also expressed E-cadherin, as judged by immunofluorescent staining protocols (Laird et al., *J. Cell Biol.* 131: 1193–1203, 1995) (FIG. 14C). In contrast, the NRK cells which were treated with N-Ac-CHAVC-NH$_2$ (SEQ ID NO:10) did not adhere to one another and failed to form a contiguous monolayer (FIG. 13D). Furthermore, these cells expressed greatly reduced levels of E-cadherin (FIG. 14D). These data demonstrate that N-Ac-CHAVC-NH$_2$ (SEQ ID NO:10) is capable of disrupting NRK cell adhesion.

EXAMPLE 7

Enhancement of Human Skin Permeability

The epithelial cells of the skin (known as keratinocytes) express E-cadherin. This Example illustrates the use of a representative cyclic peptide to enhance the permeability of human skin.

Abdominal skin from humans at autopsy within 24 hours of death was used in these assays. The effect of N-Ac-CHAVC-NH$_2$ (SEQ ID NO:10) and N-Ac-CHGVC-NH$_2$ (SEQ ID NO:20), used at a concentration of 500 μg/ml or 2.5 mg/ml, on the penetration of two fluorescent markers, Oregon Green 488 (charge −1, MW 386 daltons) and Rhodamine Green 3000 Dextran (no charge, MW 3000 daltons) through human skin was then evaluated utilizing a Franz Cell apparatus (Franz, *Curr. Prob. Dermatol.* 7:58–68, 1978; Franz, *J. Invest. Dermatol.* 64:190–195, 1975). The peptides and markers were dissolved in sterile phosphate buffer, pH 7.2, and phosphate buffer was used as the receptor fluid. 150 μl of solution containing 0.2 mg Oregon Green and 1.0 mg Rhodamine Green was used to evaluate 500 μg/ml peptide; 200 μl of solution containing 0.05 mg Oregon Green and 1.250 mg Rhodamine Green was used to evaluate 2.5 mg/ml peptide. The solution was placed on top of the epidermal side of the skin, and the penetration of the markers through the skin was assessed using a fluorescent spectrophotometric method (in a Perkin Elmer 650-105 Fluorescence Spectrophotometer, and comparing the reading to a standard curve) at 6, 12, 24, 36, and 48 hours after the start of the experiment. The fluorescent units were converted to a concentration unit of microgram/5 ml (volume of the receiver compartment) using a standard curve and regression analysis equations. The curve was linear for the concentrations tested for both markers ($r_2$=1 for OrG and 0.997 for RhG). For each peptide and marker combination, the experiment was performed in triplicate.

Figure 18:
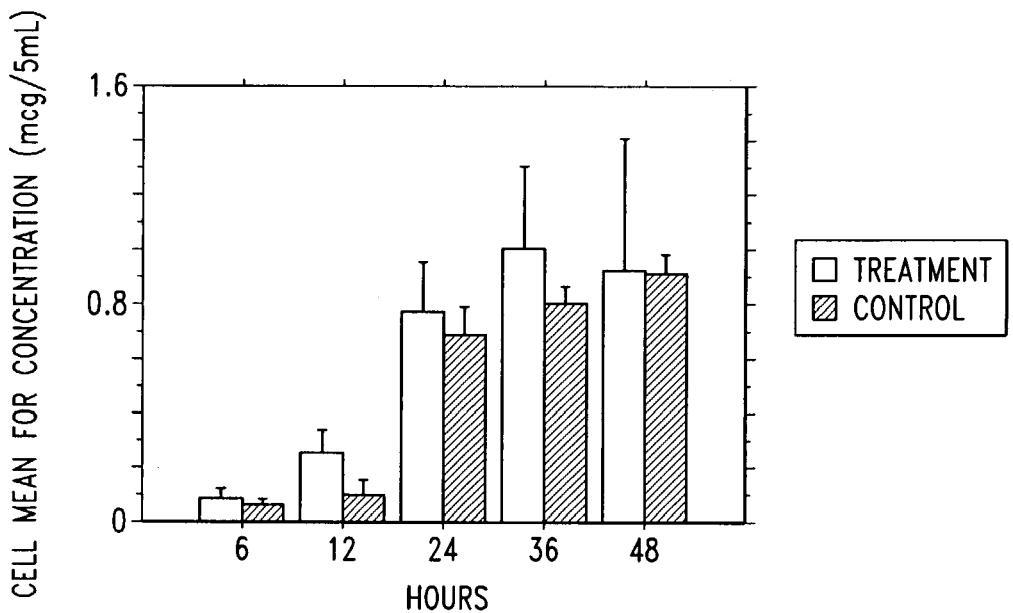
FIG. 18 is a histogram illustrating the effect of 500 µg/ml of a representative cyclic peptide (N-Ac-CHAVC-NH$_2$; SEQ ID NO:10; treatment bars) on the penetration of Oregon Green through the skin, as compared to the effect of the control peptide N-Ac-CHGVC-NH$_2$ (SEQ ID NO:20; control bars). Penetration was determined by converting fluorescent units to a concentration unit of microgram/5 ml (volume of the receiver compartment) using a standard curve and regression analysis equations.
Figure 19:
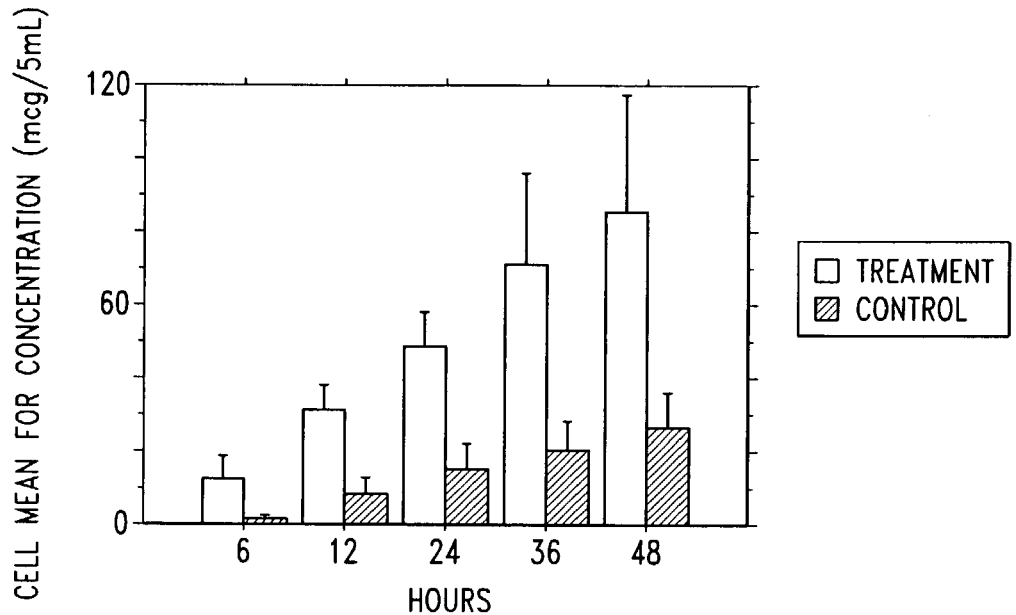
FIG. 19 is a histogram illustrating the effect of 500 µg/ml of a representative cyclic peptide (N-Ac-CHAVC-NH$_2$ (SEQ ID NO:10); treatment bars) on the penetration of Rhodamine Green through the skin, as compared to the effect of the control peptide N-Ac-CHGVC-NH$_2$ (SEQ ID NO:20; control bars). Penetration was determined by converting fluorescent units to a concentration unit of microgram/5 ml (volume of the receiver compartment) using a standard curve and regression analysis equations.

At 500 μg/ml, N-Ac-CHAVC-NH$_2$ (SEQ ID NO:10; sample #1) slightly increased the penetration of Oregon Green through the skin, as compared to the effect of N-Ac-CHGVC-NH$_2$ (SEQ ID NO:20; sample #3) on the penetration of this marker (Table 3 and FIG. 18). The penetration of Rhodamine Green through the skin was significantly increased in the presence of N-Ac-CHAVC-NH$_2$ (SEQ ID NO:10), in comparison to N-Ac-CHGVC-NH$_2$ (SEQ ID NO:20) (Table 4 and FIG. 19).

Figure 20:
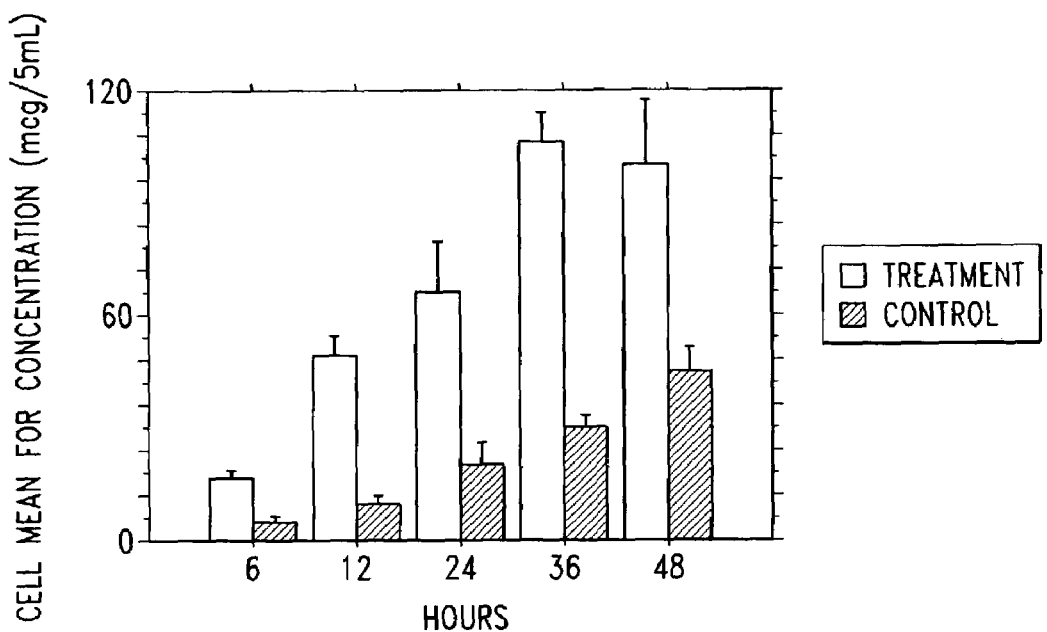
FIG. 20 is a histogram illustrating the effect of 2.5 mg/ml of a representative cyclic peptide (N-Ac-CHAVC-NH$_2$ (SEQ ID NO:10); treatment bars) on the penetration of Oregon Green through the skin, as compared to the effect of the control peptide N-Ac-CHGVC-NH$_2$ (SEQ ID NO:20; control bars). Penetration was determined by converting fluorescent units to a concentration unit of microgram/5 ml (volume of the receiver compartment) using a standard curve and regression analysis equations.
Figure 21:
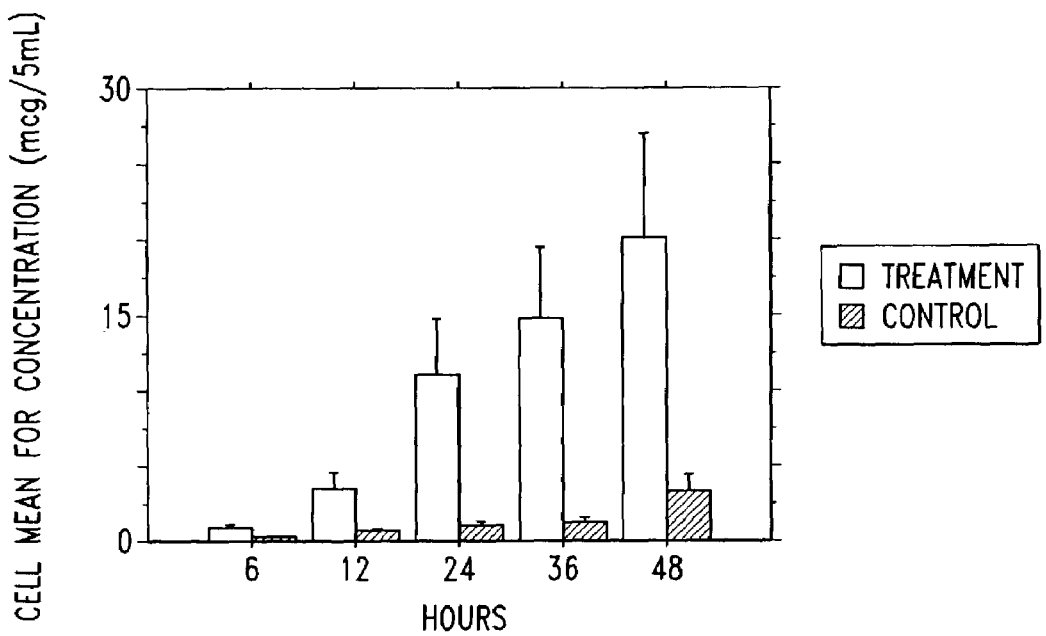
FIG. 21 is a histogram illustrating the effect of 2.5 mg/ml of a representative cyclic peptide (N-Ac-CHAVC-NH$_2$ (SEQ ID NO:10); treatment bars) on the penetration of Rhodamine Green through the skin, as compared to the effect of the control peptide N-Ac-CHGVC-NH$_2$ (SEQ ID NO:20; control bars). Penetration was determined by converting fluorescent units to a concentration unit of microgram/5 ml (volume of the receiver compartment) using a standard curve and regression analysis equations.

At 2.5 mg/ml, N-Ac-CHAVC-NH$_2$ (SEQ ID NO:10; sample #1) increased the penetration of Oregon Green through the skin, as compared to the effect of N-Ac-CHGVC-NH$_2$ (SEQ ID NO:20; sample #3) on the penetration of this marker (Table 3 and FIG. 20). The penetration of Rhodamine Green through the skin was significantly increased in the presence of N-Ac-CHAVC-NH$_2$ (SEQ ID NO:11), in comparison to N-Ac-CHGVC-NH$_2$ (SEQ ID NO:20) (Table 4 and FIG. 21).

TABLE 3

*Percutaneous absorption concentration (mg/5 ml) for Oregon Green ™ 488 as a function of time

| # Sample # | t = 6 hours | t = 12 hours | t = 24 hours | t = 36 hours | t = 48 hours |
|---|---|---|---|---|---|
| 500 μg/ml Peptide | | | | | |
| 1 Sample #1 | 0.028 | 0.096 | 0.470 | 0.544 | 0.665 |
| 2 Sample #1 | 0.167 | 0.322 | 1.096 | 1.56 | 1.725 |
| 3 Sample #1 | 0.058 | 0.352 | 0.773 | 0.902 | 0.971 |
| Mean Sample #1 | 0.084 | 0.225 | 0.780 | 1.00 | 1.120 |
| 1 Sample #3 | 0.098 | 0.200 | 0.709 | 0.769 | 0.923 |
| 2 Sample #3 | 0.022 | 0.107 | 0.864 | 0.923 | 1.021 |
| 3 Sample #3 | 0.045 | 0.088 | 0.522 | 0.714 | 0.764 |
| Mean Sample #3 | 0.055 | 0.132 | 0.698 | 0.802 | 0.902 |
| 2.5 mg/ml Peptide | | | | | |
| 1 Sample #1 | 0.14 | 0.44 | 0.67 | 0.76 | 0.83 |
| 2 Sample #1 | 0.11 | 0.32 | 0.33 | 0.88 | 0.56 |
| 3 Sample #1 | 0.16 | 0.45 | 0.63 | 0.99 | 1.06 |
| Mean Sample #1 | 0.14 | 0.40 | 0.54 | 0.88 | 0.82 |
| 1 Sample #3 | 0.04 | 0.11 | 0.12 | 0.23 | 0.36 |
| 2 Sample #3 | 0.01 | 0.04 | 0.11 | 0.22 | 0.26 |
| 3 Sample #3 | 0.06 | 0.08 | 0.26 | 0.29 | 0.46 |
| Mean Sample #3 | 0.04 | 0.07 | 0.16 | 0.25 | 0.36 |
| no dye | 0 | 0 | 0 | 0 | 0 |
| no dye | 0 | 0 | 0 | 0 | 0 |

*Defined as amount found in the receiver compartment (volume = 5 ml)

TABLE 4

*Percutaneous absorption concentration (mg/5 ml) for Dextran Rhodamine Green 3000 as a function of time

| # Sample # | t = 6 hours | t = 12 hours | t = 24 hours | t = 36 hours | t = 48 hours |
|---|---|---|---|---|---|
| 500 μg/ml Peptide | | | | | |
| 1 Sample #1 | 0.4 | 3.0 | 16.174 | 21.044 | 25.747 |
| 2 Sample #1 | 0.8 | 2.0 | 4.074 | 5.556 | 6.481 |
| 3 Sample #1 | 1.2 | 5.556 | 13.158 | 17.565 | 27.826 |

TABLE 4-continued

*Percutaneous absorption concentration (mg/5 ml) for
Dextran Rhodamine Green 3000 as a function of time

| # Sample # | t = 6 hours | t = 12 hours | t = 24 hours | t = 36 hours | t = 48 hours |
|---|---|---|---|---|---|
| Mean Sample #1 | 0.8 | 3.52 | 11.15 | 14.72 | 20.02 |
| 1 Sample #3 | 0.2 | 0.6 | 1.0 | 1.0 | 1.8 |
| 2 Sample #3 | 0.3 | 1.0 | 1.4 | 1.6 | 5.370 |
| 3 Sample #3 | 0.2 | 0.4 | 0.8 | 1.0 | 1.8 |
| Mean Sample #3 | 0.23 | 0.67 | 1.07 | 1.2 | 2.99 |
| 2.5 mg/ml Peptide | | | | | |
| 1 Sample #1 | 24.52 | 45.35 | 66.28 | 120.0 | 146.79 |
| 2 Sample #1 | 2.4 | 25.22 | 35.22 | 42.36 | 47.00 |
| 3 Sample #1 | 11.05 | 23.83 | 44.85 | 51.50 | 60.1 |
| Mean Sample #1 | 12.66 | 31.47 | 48.78 | 71.28 | 133.56 |
| 1 Sample #3 | 1.8 | 17.02 | 27.47 | 33.06 | 40.86 |
| 2 Sample #3 | 0.2 | 2.0 | 5.56 | 5.79 | 8.25 |
| 3 Sample #3 | 3.8 | 7.89 | 13.9 | 20.35 | 27.48 |
| Mean Sample #3 | 1.93 | 8.97 | 15.64 | 19.73 | 25.53 |
| no dye | 0 | 0 | 0 | 0 | 0 |
| no dye | 0 | 0 | 0 | 0 | 0 |

*Defined as amount found in the receiver compartment (volume = 5 ml)

EXAMPLE 8

Disruption of Human Ovarian Cancer Cell Adhesion

This Example further illustrates the ability of representative cyclic peptides to disrupt human ovarian cancer-cell adhesion.

Figure 15A:
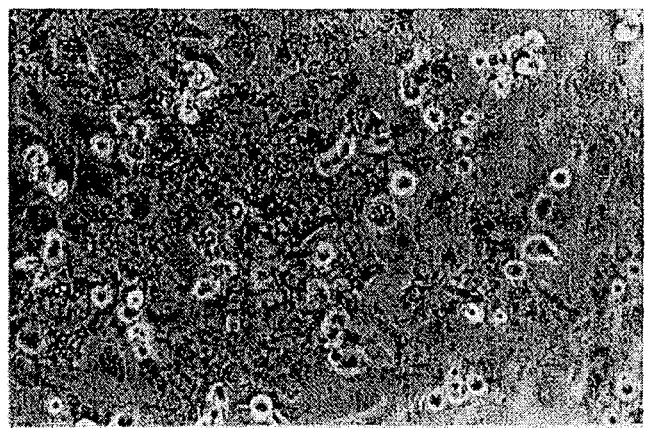
FIGS. 15A–15C are photographs showing monolayer cultures of human ovarian cancer cells (OVCAR3) in the presence of varying concentrations of a representative cyclic peptide.
Figure 15B:
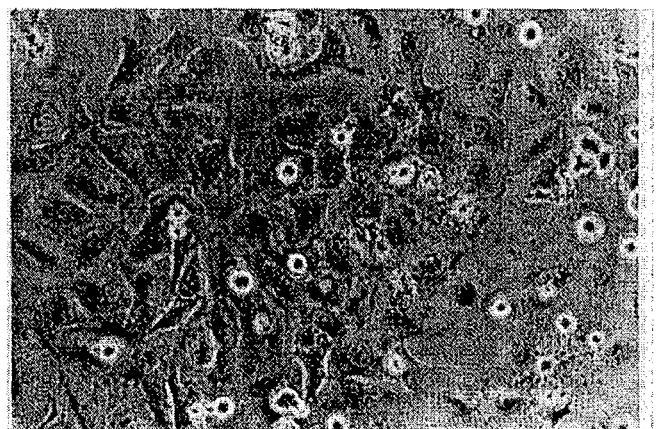
Figure 15C:
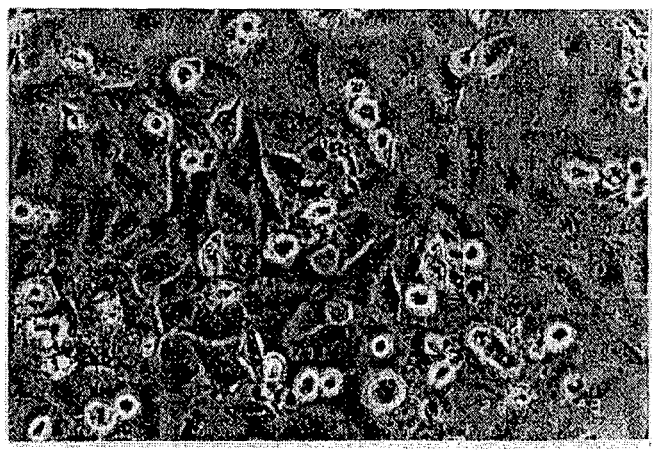

The human ovarian cancer cell line OVCAR-3, which expresses E-cadherin, was used in these experiments. Cells were cultured in RPMI supplemented with insulin and containing 20% FCS. Cells were grown in T-250 culture flasks and maintained by periodic subculturing. Cells were harvested from flasks and seeded in individual wells of 96-well culture dishes (surface area of each well was 0.32 cm$^2$) at a density of 50,000 cells per well in 0.1 ml media containing the cyclic peptides (at concentrations of 1, 0.1, or 0.01 mg/ml). Media control wells were also established. Cultures were evaluated periodically by microscopic examination under both bright field and phase contrast conditions, and were maintained for 48 hours. N-Ac-CHAVC-NH$_2$ (SEQ ID NO:10) was found to be inactive within this assay at these concentrations. However, the cyclic peptide N-Ac-CAHVSC-NH$_2$ (SEQ ID NO:27) disrupted OVCAR-3 adhesion (FIGS. 15A–C)). This data demonstrates that N-Ac-CAHVSC-NH$_2$ (SEQ ID NO:27) specifically affects cells that express E-cadherin.

EXAMPLE 9

Disruption of Melanoma Cell Adhesion

This Example illustrates the ability of a representative cyclic peptide to disrupt melanoma cell adhesion.

Melanoma ME115 cells (kindly provided by Meenhard Herlyn, Wistar Institute, Philadelphia, Pa.) were plated on glass coverslips and cultured for 24 hours in 50% keratinocyte growth medium (Clonetics, San Diego, Calif.) and 50% L15. Fresh medium containing the cyclic peptides (final concentration 500 µg/mL media) N-Ac-CHAVC-NH$_2$ (SEQ ID NO:10) or N-Ac-CHGVC-NH$_2$ (SEQ ID NO:20) was then added. Following 24 hours of culture in the presence of the peptides, the medium was removed and fresh medium containing the peptides was added. The cells were fixed 24 hours later with cold methanol and stored in phosphate buffered saline (PBS).

Coverslips were blocked for 1 hour in 3% ovalbumin/PBS and incubated for a further 1 hour in the presence of rabbit pan-cadherin antibody (Sigma Chemical Co., St. Louis, Mo.) diluted 1:500. Primary and secondary antibodies were diluted in PBS containing 6% normal goat serum. Following incubation in the primary antibody, coverslips were washed 3 times for 5 minutes each in PBS and incubated for 1 hour in goat anti-rabbit immunoglobulin G conjugated to fluorescein (Kiekegard and Perry, South San Francisco, Calif.) diluted 1:100. Following a further wash in PBS (3×5 minutes) coverslips were mounted in Vectashield (Vector Labs, Burlingame, Calif.) and viewed with a Zeiss infinity corrected microscope.

Figure 16A:
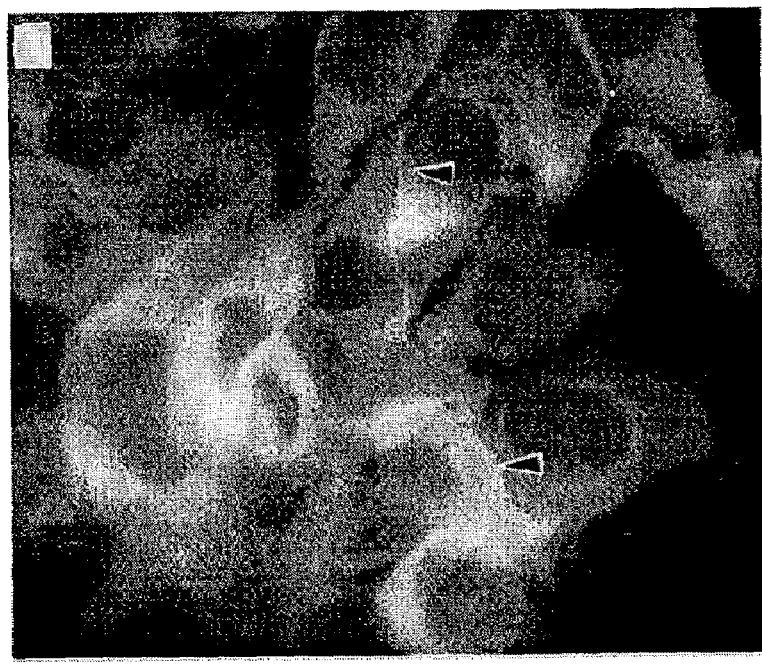
FIGS. 16A and 16B are photographs showing cultures of human melanoma ME115 cells in the presence (FIG. 16B) and absence (FIG. 16A) of a representative cyclic peptide. The cells have been immunolabeled for cadherin.
Figure 16B:

Photographs, shown in FIG. 16, show an absence of cell membrane staining and the appearance of bright intracellular vesicular staining in cells treated with N-Ac-CHAVC-NH$_2$ (SEQ ID NO:10). In contrast, cells exposed to N-Ac-CHGVC-NH$_2$ (SEQ ID NO:20) displayed cadherin staining all over the cell membrane. Occasionally, the staining concentrated at points of cell-cell contact. These results indicate that the representative cyclic peptide N-Ac-CHAVC-NH$_2$ (SEQ ID NO:10) disrupts melanoma cell adhesion.

EXAMPLE 10

Disruption of Breast Cancer Cell Adhesion

This Example illustrates the ability of a representative cyclic peptide to disrupt human breast epithelial cell adhesion.

A1N4 human breast epithelial cells (kindly provided by Martha Stampfer, Lawrence Berkeley Laboratory, Berkeley, Calif.) were plated on glass coverslips and cultured in F12/DME containing 0.5% FCS and 10 ng/mL EGF for 24 hours. Fresh medium containing the cyclic peptides (final concentration 500 µg/mL media) N-Ac-CHAVC-NH$_2$ (SEQ ID NO:10) or N-Ac-CHGVC-NH$_2$ (SEQ ID NO:20) was then added. Following 24 hours of culture in the presence of the peptides, the medium was removed and fresh medium containing the peptides was added. The cells were fixed 24 hours later with cold methanol and stored in phosphate buffered saline (PBS).

Coverslips were blocked for 1 hour in 3% ovalbumin/PBS and incubated for a further 1 hour in the presence of 1 µg/mL mouse anti-E-cadherin antibody (Zymed, Gaithersburg, Md.). Primary and secondary antibodies were diluted in PBS containing 6% normal goat serum. Following incubation in the primary antibody, coverslips were washed 3 times for 5 minutes each in PBS and incubated for 1 hour with goat anti-mouse conjugated to fluorescein (Kiekegard and Perry, South San Francisco, Calif.) diluted 1:100. Following a further wash in PBS (3×5 minutes) coverslips were mounted in Vectashield (Vector Labs, Burlingame, Calif.) and viewed with a Zeiss infinity corrected microscope.

Figure 17A:
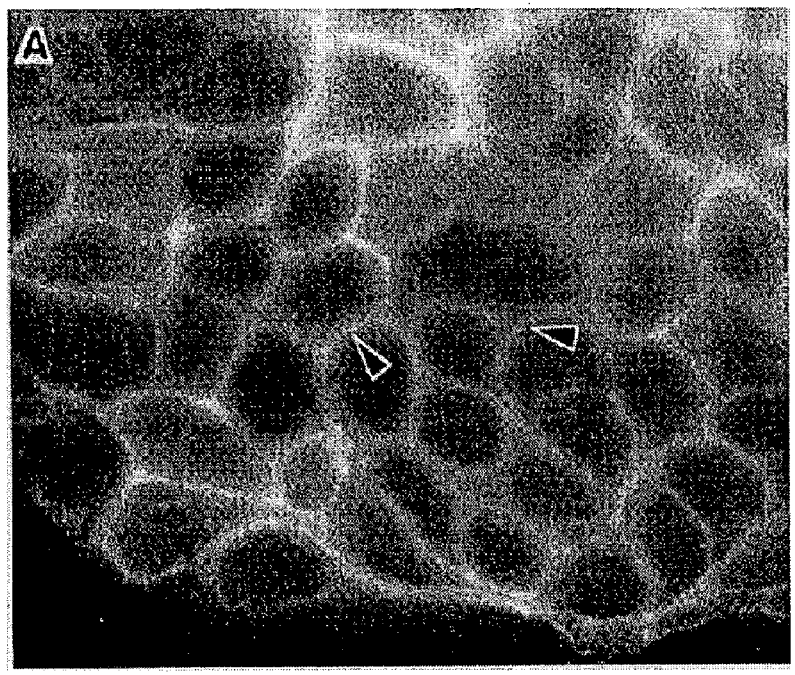
FIGS. 17A and 17B are photographs showing monolayer cultures of A1N4 human breast epithelial cells in the presence (FIG. 17B) and absence (FIG. 17A) of a representative cyclic peptide. The cells have been immunolabeled for E-cadherin.
Figure 17B:

Photographs, shown in FIGS. 17A and B, show reduced E-cadherin staining with a stitched appearance in cells treated with N-Ac-CHAVC-NH$_2$ (SEQ ID NO:10). In addition, holes are present in the monolayer where the cells have retracted from one another. In contrast, cells exposed to N-Ac-CHGVC-NH$_2$ (SEQ ID NO:20) displayed E-cadherin staining concentrated at points of cell-cell contact and formed a tightly adherent monolayer.

EXAMPLE 11

Toxicity and Cell Proliferation Studies

This Example illustrates the initial work to evaluate the cytotoxic effects of representative cyclic peptides.

N-Ac-CHAVC-NH$_2$ (SEQ ID NO:10) and the control peptide N-Ac-CHGVC-NH$_2$ (SEQ ID NO:20) were evaluated for possible cytotoxic effects on human microvascular endothelial (HMVEC; Clonetics), human umbilical vein endothelial (HUVEC; ATCC #CRL-1730), IAFp2 (human fibroblast cell line; Institute Armand-Frapier, Montreal, Quebec), WI-38 (human fibroblast cell line; ATCC #CCL-75), MDA-MB231 (human breast cancer cell line; ATCC #HTB-26), and PC-3 (human prostate cancer cell line; ATCC #CRL-1435) cells utilizing the MTT assay (Plumb et al., *Cancer Res.* 49:4435–4440, 1989). Neither of the peptides was cytotoxic at concentrations up to and including 100 µM. Similarly, neither of the peptides was capable of inhibiting the proliferation of the above cell lines at concentrations up to 100 µM, as judged by $^3$H-thymidine incorporation assays.

In fact, none of the compounds tested thus far show any cytotoxicity at concentrations up to and including 100 µM (Table 5 and 6). However, N-Ac-CAHVSC-NH$_2$ (SEQ ID NO:27), N-Ac-CHGVSC-NH$_2$ (SEQ ID NO:48), N-Ac-CVAHC-NH$_2$ (SEQ ID NO:54), N-Ac-CVGHC-NH$_2$ (SEQ ID NO:55) and N-Ac-CSHAVSSC-NH$_2$ (SEQ ID NO:28) inhibited the proliferation of HUVEC at concentrations (IC$_{50}$ values) of 57 µM, 42 µM, 8 µM, 30 µM and 69 µM respectively, as judged by $^3$H-thymidine incorporation assays. N-Ac-CSHAVSSC-NH$_2$ (SEQ ID NO:28) also inhibited the proliferation of MDA-MB231 cells at a concentration of 76 µM and HMVEC cells at a concentration of 70 µM (Tables 5 and 6). N-Ac-CAHVSC-NH$_2$ (SEQ ID NO:27) inhibited the proliferation of MDA-MB231 cells at a concentration of 52 µM.

TABLE 5

Evaluation of Peptides for Cytotoxicity and Capacity to Inhibit Cell Proliferation of Normal Cells (IC$_{50}$ in µM)

| Peptide | SEQ ID | Normal Cells | | | | | | | |
|---|---|---|---|---|---|---|---|---|---|
| | | HMVEC | | HUVEC | | IAFp2 | | WI-38 | |
| | | Cell prol | Cytotox | Cell Prol | Cytotox | Cell Prol | Cytotox | Cell Prol | Cytotox |
| N-Ac-CHGVC-NH$_2$ (control for #1) | 20 | >100 µM | >100 µM | >100 µM | >100 µM | >100 µM | >100 µM | >100 µM | >100 µM |
| N-Ac-CHAVC-NH$_2$ (#1) | 10 | >100 µM | >100 µM | >100 µM | >100 µM | >100 µM | >100 µM | >100 µM | >100 µM |
| H-CHGVC-NH$_2$ (control for #2) | 20 | >100 µM | >100 µM | >100 µM | >100 µM | >100 µM | >100 µM | >100 µM | >100 µM |
| H-CHAVC-NH$_2$ (#2) | 10 | >100 µM | >100 µM | >100 µM | >100 µM | >100 µM | >100 µM | >100 µM | >100 µM |
| N-Ac-CHGVSC-NH$_2$ (control for #18) | 48 | >100 µM | >100 µM | 42 µM | >100 µM | >100 µM | >100 µM | >100 µM | >100 µM |
| N-Ac-CHAVSC-NH$_2$ * (#18) | 27 | >100 µM | >100 µM | 57 µM | >100 µM | >100 µM | >100 µM | >100 µM | >100 µM |
| N-Ac-CSHGVC-NH$_2$ (control for #16) | 47 | >100 µM | >100 µM | >100 µM | >100 µM | >100 µM | >100 µM | >100 µM | >100 µM |
| N-Ac-CSHAVC-NH$_2$ (#16) | 26 | >100 µM | >100 µM | >100 µM | >100 µM | >100 µM | >100 µM | >100 µM | >100 µM |
| N-Ac-CAHGVDC-NH$_2$ (control for #22) | 46 | >100 µM | >100 µM | >100 µM | >100 µM | >100 µM | >100 µM | >100 µM | >100 µM |
| N-Ac-CAHAVDC-NH$_2$ (#22) | 13 | >100 µM | >100 µM | >100 µM | >100 µM | >100 µM | >100 µM | >100 µM | >100 µM |
| N-Ac-KHGVD-NH$_2$ (control for #26) | 38 | >100 µM | >100 µM | >100 µM | >100 µM | >100 µM | >100 µM | >100 µM | >100 µM |
| N-Ac-KHAVD-NH$_2$ (#26) | 37 | >100 µM | >100 µM | >100 µM | >100 µM | >100 µM | >100 µM | >100 µM | >100 µM |
| H-CAHGVDC-NH$_2$ (control for #45) | 46 | >100 µM | >100 µM | >100 µM | >100 µM | >100 µM | >100 µM | >100 µM | >100 µM |
| H-CAHAVDC-NH$_2$ (#45) | 13 | >100 µM | >100 µM | >100 µM | >100 µM | >100 µM | >100 µM | >100 µM | >100 µM |

TABLE 5-continued

Evaluation of Peptides for Cytotoxicity and Capacity to Inhibit Cell Proliferation of Normal Cells (IC$_5$0 in μM)

| Peptide | SEQ ID | HMVEC Cell prol | HMVEC Cytotox | HUVEC Cell Prol | HUVEC Cytotox | IAFp2 Cell Prol | IAFp2 Cytotox | WI-38 Cell Prol | WI-38 Cytotox |
|---|---|---|---|---|---|---|---|---|---|
| H-CAHGVDIC-NH$_2$ (control for #47) | 41 | >100 μM | >100 μM | >100 μM | >100 μM | >100 μM | >100 μM | >100 μM | >100 μM |
| H-CAHAVDIC-NH$_2$ (#47) | 14 | >100 μM | >100 μM | >100 μM | >100 μM | >100 μM | >100 μM | >100 μM | >100 μM |
| N-Ac-CVGHC-NH$_2$ (control for #32) | 55 | >100 μM | >100 μM | 30 μM | >100 μM | >100 μM | >100 μM | >100 μM | >100 μM |
| N-Ac-CVAHC-NH$_2$ (#32) | 54 | >100 μM | >100 μM | 8 μM | >100 μM | >100 μM | >100 μM | >100 μM | >100 μM |
| N-Ac-CAHGVDIC-NH$_2$ (control for #14) | 41 | >100 μM | >100 μM | >100 μM | >100 μM | >100 μM | >100 μM | >100 μM | >100 μM |
| N-Ac-CAHAVDIC-NH$_2$ (#14) | 14 | >100 μM | >100 μM | >100 μM | >100 μM | >100 μM | >100 μM | >100 μM | >100 μM |
| N-Ac-CSHGVSSC-NH$_2$ (control for #24) | 51 | >100 μM | >100 μM | >100 μM | >100 μM | >100 μM | >100 μM | >100 μM | >100 μM |
| N-Ac-CSHAVSSC-NH$_2$ * (#24) | 28 | 70 μM | >100 μM | 69 μM | >100 μM | >100 μM | >100 μM | >100 μM | >100 μM |

* Incompletely soluble in RPMI at 1 mM

TABLE 6

Evaluation of Peptides for Cytotoxicity and Capacity to Inhibit Cell Proliferation of Tumoral Cells (IC$_5$0 in μM)

| Peptide | SEQ ID | MDA-MB231 Cell Prol | MDA-MB231 Cytotox | PC-3 Cell Prol | PC-3 Cytotox |
|---|---|---|---|---|---|
| N-Ac-CHGVC-NH$_2$ (control for #1) | 20 | >100 μM | >100 μM | >100 μM | >100 μM |
| N-Ac-CHAVC-NH$_2$ (#1) | 10 | >100 μM | >100 μM | >100 μM | >100 μM |
| H-CHGVC-NH$_2$ (control for #2) | 20 | >100 μM | >100 μM | >100 μM | >100 μM |
| H-CHAVC-NH$_2$ (#2) | 10 | >100 μM | >100 μM | >100 μM | >100 μM |
| N-Ac-CHGVSC-NH$_2$ (control for #18) | 48 | >100 μM | >100 μM | >100 μM | >100 μM |
| N-Ac-CHAVSC-NH$_2$*(#18) | 27 | 52 μM | >100 μM | >100 μM | >100 μM |
| N-Ac-CSHGVC-NH$_2$ (control for #16) | 47 | >100 μM | >100 μM | >100 μM | >100 μM |
| N-Ac-CSHAVC-NH$_2$ (#16) | 26 | >100 μM | >100 μM | >100 μM | >100 μM |
| N-Ac-CAHGVDC-NH$_2$ (control for #22) | 46 | >100 μM | >100 μM | >100 μM | >100 μM |
| N-Ac-CAHAVDC-NH$_2$ (#22) | 13 | >100 μM | >100 μM | >100 μM | >100 μM |
| N-Ac-KHGVD-NH$_2$ (control for #26) | 38 | >100 μM | >100 μM | >100 μM | >100 μM |
| N-Ac-KHAVD-NH$_2$ (#26) | 37 | >100 μM | >100 μM | >100 μM | >100 μM |
| H-CAHGVDC-NH$_2$ (control for #45) | 46 | >100 μM | >100 μM | >100 μM | >100 μM |
| H-CAHAVDC-NH$_2$ (#45) | 13 | >100 μM | >100 μM | >100 μM | >100 μM |

TABLE 6-continued

Evaluation of Peptides for Cytotoxicity and Capacity to Inhibit Cell Proliferation of Tumoral Cells (IC$_{50}$ in μM)

| Peptide | SEQ ID | Tumoral Cells | | | |
|---|---|---|---|---|---|
| | | MDA-MB231 | | PC-3 | |
| | | Cell Prol | Cytotox | Cell Prol | Cytotox |
| H-CAHGVDIC-NH$_2$ (control for #47) | 41 | >100 μM | >100 μM | >100 μM | >100 μM |
| H-CAHAVDIC-NH$_2$ (#47) | 14 | >100 μM | >100 μM | >100 μM | >100 μM |
| N-Ac-CVGHC-NH$_2$ (control for #32) | 55 | >100 μM | >100 μM | >100 μM | >100 μM |
| N-Ac-CVAHC-NH$_2$ (#32) | 54 | >100 μM | >100 μM | >100 μM | >100 μM |
| N-Ac-CAHGVDIC-NH$_2$ (control for #14) | 41 | >100 μM | >100 μM | >100 μM | >100 μM |
| N-Ac-CAHAVDIC-NH$_2$ (#14) | 14 | >100 μM | >100 μM | >100 μM | >100 μM |
| N-Ac-CSHGVSSC-NH$_2$ (control for #24) | 51 | >100 μM | >100 μM | >100 μM | >100 μM |
| N-Ac-CSHAVSSC-NH$_2$ * (#24) | 28 | 76 μM | >100 μM | >100 μM | >100 μM |

EXAMPLE 12

Chronic Toxicity Study

This Example illustrates a toxicity study performed using a representative cyclic peptide.

Figure 22:
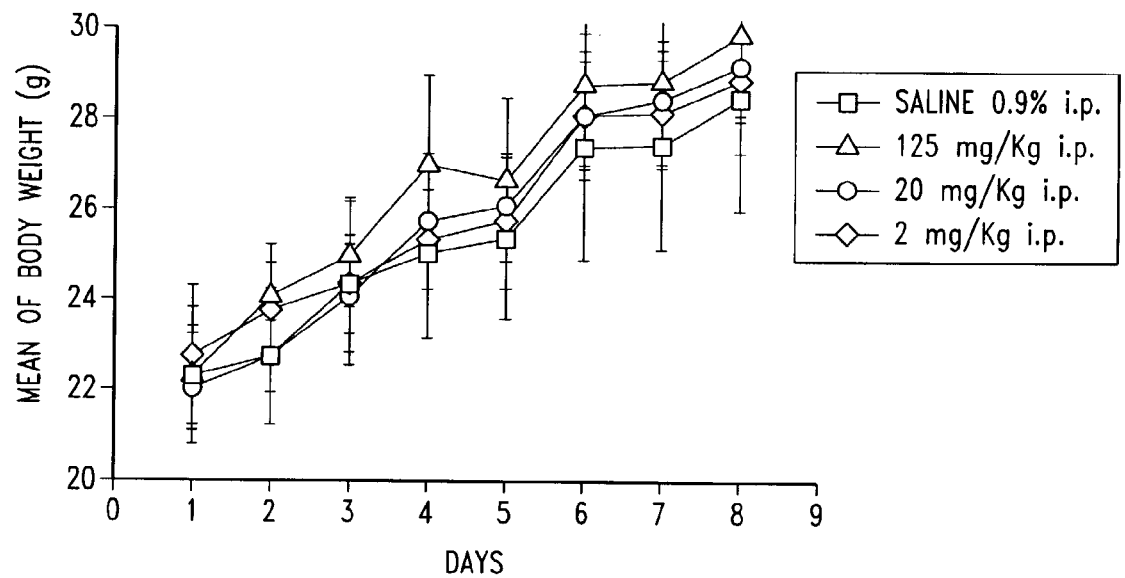
FIG. 22 is a graph illustrating the results of a study to assess the chronic toxicity of a representative cyclic peptide. The graph presents the mean body weight during the three-day treatment period (one intraperitoneal injection per day) and the four subsequent recovery days. Three different doses are illustrated, as indicated.

Varying amounts of H-CHAVC-NH$_2$ (SEQ ID NO:10; 2 mg/kg, 20 mg/kg and 125 mg/kg) were injected into mice intraperitoneally every day for three days. During the recovery period (days 4–8), animals were observed for clinical symptoms. Body weight was measured (FIG. 22) and no significant differences occurred. In addition, no clinical symptoms were observed on the treatment or recovery days. Following the four day recovery period, autopsies were performed and no abnormalities were observed.

EXAMPLE 13

Stability of Cyclic Peptide in Blood

This Example illustrates the stability of a representative cyclic peptide in mouse whole blood.

Figure 23:
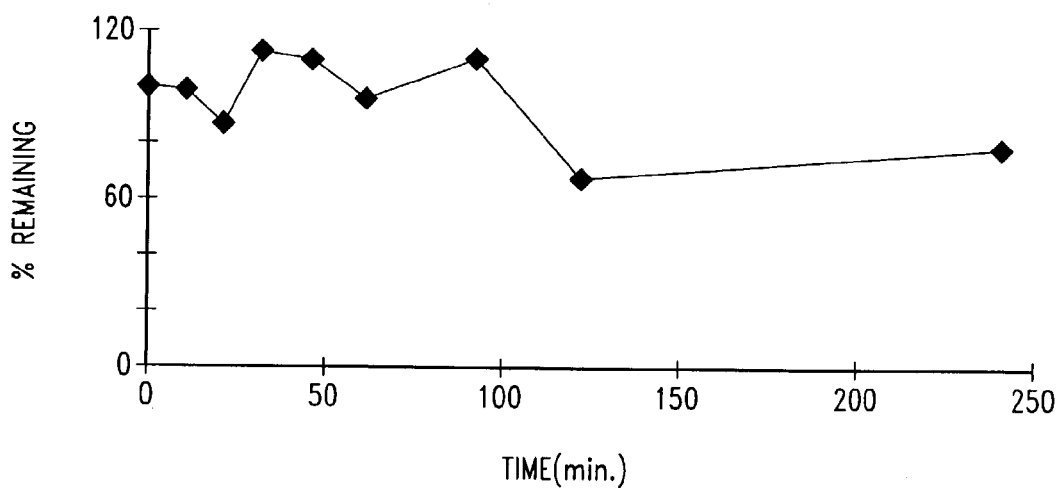
FIG. 23 is a graph illustrating the stability of a representative cyclic peptide in mouse whole blood. The percent of the cyclic peptide remaining in the blood was assayed at various time points, as indicated.

50 μl of a stock solution containing 12.5 μg/ml H-CHAVC-NH$_2$ (SEQ ID NO:10) was added to mouse whole blood and incubated at 37° C. Aliquots were removed at intervals up to 240 minutes, precipitated with acetonitrile, centrifuged and analyzed by HPLC. The results (Table 7 and FIG. 23) are expressed as % remaining at the various time points, and show generally good stability in blood.

TABLE 7

Stability of Representative Cyclic Peptide in Mouse Whole Blood

| Time (Min.) | Area 1 | Area 2 | Average | % Remaining |
|---|---|---|---|---|
| 0 | 341344 | 246905 | 294124.5 | 100.00 |
| 10 | 308924 | 273072 | 290998 | 98.94 |

TABLE 7-continued

Stability of Representative Cyclic Peptide in Mouse Whole Blood

| Time (Min.) | Area 1 | Area 2 | Average | % Remaining |
|---|---|---|---|---|
| 20 | 289861 | 220056 | 254958.5 | 86.68 |
| 30 | 353019 | 310559 | 331789 | 112.81 |
| 45 | 376231 | 270860 | 323545.5 | 110.00 |
| 60 | 373695 | 188255 | 280975 | 95.53 |
| 90 | 435555 | 216709 | 326132 | 110.88 |
| 120 | 231694 | 168880 | 200287 | 68.10 |
| 240 | 221952 | 242148 | 232050 | 78.90 |

EXAMPLE 14

Use of Flanking Sequences to Influence Cadherin Receptor Specificity

This Example illustrates the effect of sequences that flank the HAV sequence on specificity for N-cadherin-mediated responses.

Cell culture and neurite outgrowth assays. Co-cultures of cerebellar neurons on monolayers of control 3T3 cells and monolayers of transfected 3T3 cells that express physiological levels of chick N-cadherin or human L1 were established as previously described (Williams et al., *Neuron* 13:583–594, 1994). In brief, 80,000 3T3 cells (control and transfected) were plated into individual chambers of an eight-chamber tissue culture slide coated with polylysine and fibronectin and cultured in DMEM/10% FCS. After 24 hours, when confluent monolayers had formed, the medium was removed and 3000 cerebellar neurons isolated from post-natal day 2–3 rats were plated into each well in SATO media (Doherty et al., *Nature* 343:464–466, 1990) supplemented with 2% FCS. All of the test peptides were added immediately before the neurons as a 2× stock prepared in SATO/2% FCS. The co-cultures were maintained for 16–18 hours, at which time they were fixed and immunostained for GAP-43 which is present only in the neurons and delineates the neuritic processes. The mean length of the longest neurite per cell was measured for 150–200 neurons sampled in replicate cultures as previously described (Williams et al., *Neuron* 13:583–594, 1994). The percentage inhibition of neurite outgrowth at various peptide concentrations was calculated as the average of at least three independent experiments. Dose-response curves were evaluated and the $EC_{50}$ values determined.

Peptide Synthesis. All peptides were synthesized using the solid-phase method (Merrifield, *Journal of the American Chemical Society* 85:2149, 1963; Stewart and Young, (1969) *Solid Phase Peptide Synthesis*, W. H. Freeman, San Francisco). The peptides were assembled on methylbenzhydrylamine resin for the C-terminal amide peptides and the traditional Merrifield resins were used for the C-terminal acid peptides. Acetylation of the N-terminal was performed by reacting the peptide resins with a solution of acetic anhydride in dichloromethane in the presence of diisopropylethylamine after removal of the N-α-Boc by acidolysis using trifluoroacetic acid. All of the cyclic peptides bear the disulfide tether Cys-S—S-Cys. Cyclization was accomplished by reacting the side chain thiol functionalities of the two cysteine residues with a 10% solution of iodine in methanol.

All peptides with the exception of N-Ac-CAHVDIC-NH$_2$ (SEQ ID NO:62) were prepared as a stock solution at a concentration of 5–10 mg/ml in distilled water, and stored in small aliquots at −70° C. until needed. For solubility reasons N-Ac-CAHVDIC-NH$_2$ (SEQ ID NO:62) was made up in tissue culture DMSO at a concentration of 20 mg/mL.

Figure 24:
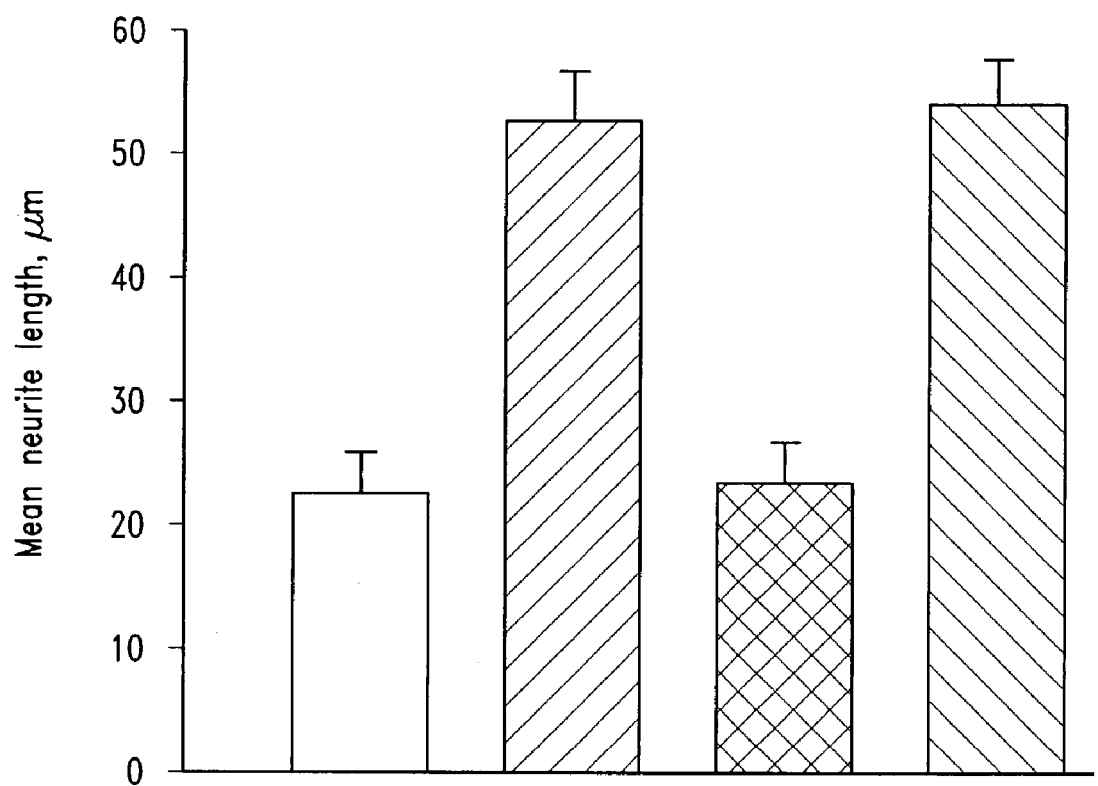
FIG. 24 is a bar graph showing the effect of N-Ac-CHAVC-NH$_2$ (SEQ ID NO:10) and N-Ac-CHGVC-NH$_2$ (SEQ ID NO:20) on N-cadherin-mediated neurite outgrowth. Mean neurite length is shown for cerebellar neurons cultured for 14 hours on monolayers of control 3T3 cells (unshaded), on N-cadherin expressing 3T3 cells (diagonal rising right), on N-cadherin expressing 3T3 cells in media supplemented with N-Ac-CHAVC-NH$_2$ (SEQ ID NO:10; diagonal cross hatch) and on N-cadherin expressing 3T3 cells in media supplemented with N-Ac-CHGVC-NH$_2$ (SEQ ID NO:20; diagonal rising left). The results show the mean length of the longest neurite measured in a single representative experiment, and the error bars show the s.e.m.

Effects of cyclic HAV peptides on N-cadherin function. The ability of N-Ac-CHAVC-NH$_2$ (SEQ ID NO:10; compound 1) to inhibit neurite outgrowth was initially tested. This cyclic peptide has the cadherin CAR sequence (HAV) and no flanking amino acid residues. Neurons were cultured on confluent monolayers of control (untransfected) and N-cadherin expressing 3T3 cells for 16–18 hours. The cells were then fixed and the length of the longest neurite on 150–200 neurons was determined by standard assay, as described above. FIG. 24 gives the mean neurite length in a representative experiment where cerebellar neurons have been cultured over control and N-cadherin expressing cells. In the absence of peptide, the mean length of the longest neurite per cell was approximately double on the N-cadherin expressing cells, as compared to 3T3 cells. This response requires N-cadherin function in both the neuron and transfected fibroblast. FIG. 24 also illustrates inhibition of neurite outgrowth in neurons cultured over N-cadherin expressing cells in the presence of N-Ac-CHAVC-NH$_2$ (SEQ ID NO:10; compound 1, 500 µg/mL). In addition, the corresponding control peptide N-Ac-CHGVC-NH$_2$ (SEQ ID NO:20; compound 2, 500 µg/mL) had no effect on neurite outgrowth over N-cadherin expressing monolayers (FIG. 24).

Figure 25:
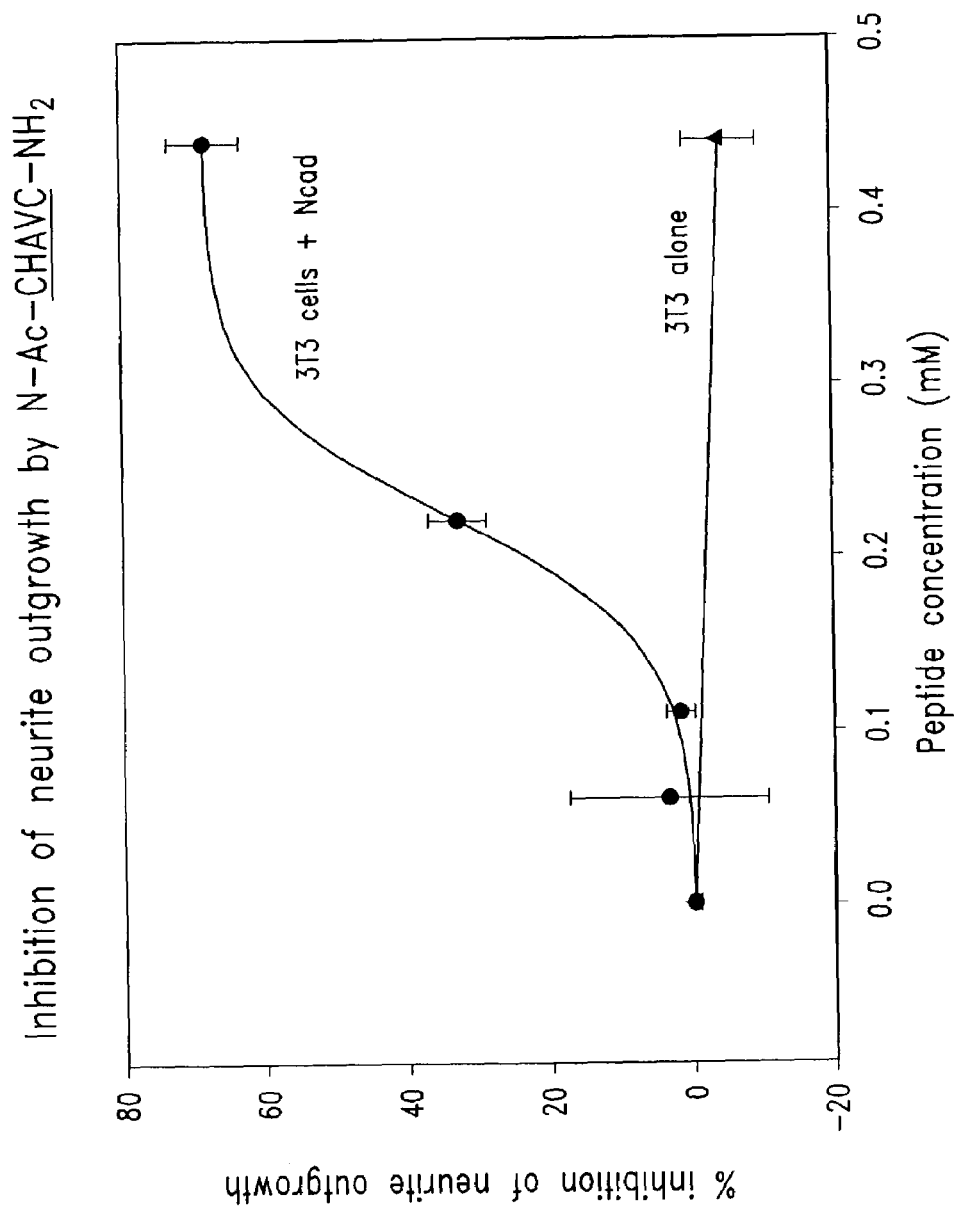
FIG. 25 is a graph showing dose-response curves that illustrate the inhibition of neurite outgrowth over both 3T3 cells and N-cadherin expressing 3T3 cells in the presence of increasing concentrations of N-Ac-CHAVC-NH$_2$ (SEQ ID NO:10). The peptide had no effect on the basal growth over 3T3 cells. The EC$_{50}$ value was determined to be 0.22 mM.

FIG. 25 gives the pooled data from a number of experiments where the neurons have been cultured over control and N-cadherin expressing cells in the presence of increasing concentrations of N-Ac-CHAVC-NH$_2$ (SEQ ID NO:10; compound 1). This compound has no significant effect on the N-cadherin response at concentrations up to 62 µg/ml. A significant inhibition (33.2+/−4.0%) of the response was seen at a peptide concentration of 125 µg/ml (mean+/−s.e.m, n=3 independent experiments), with a more complete inhibition at 250 µg/ml. Results pooled from four independent experiments demonstrated a 68.2+/−5.1% inhibition of the N-cadherin response when the peptide was present at 250 µg/ml (see Table 8). An $EC_{50}$ value of 0.22 mM was obtained from the dose-response curve. In contrast to the effects of the peptide on neurite outgrowth over N-cadherin expressing cells, it had no significant effect on neurite extension over control 3T3 cells (FIG. 25). This observation demonstrates that N-Ac-CHAVC-NH$_2$ (SEQ ID NO:10) is capable of acting as an antagonist and inhibiting cadherin function. Additionally, N-Ac-CHAVC-NH$_2$ (SEQ ID NO:10) does not inhibit integrin receptor function, as the latter is required for neurite extension over 3T3 cells. Compound 1 alone elicits a biological response of similar potency to the linear 10-mer N-Ac-LRAHAVDING-NH$_2$ (SEQ ID NO:83; % inhibition at 250 mg/mL, 68.8+/−4.1). In contrast, compound 3, with a free amino group at the N-terminal region, was inactive (Table 8).

Peptides included in Table 8 are placed into one of three groups. The first group, comprising compounds 1 and 3 can be viewed as potential general or non-specific cadherin inhibitors. The second group, which includes compounds 23, 25, 27, 29, and 31, were designed as putative E-cadherin specific inhibitors by incorporation of flanking amino acids from the HAV region of native human E-cadherin. The remaining HAV-containing compounds were designed as putative N-cadherin inhibitors by virtue of their HAV flanking amino acids being derived from the native human N-cadherin sequence.

Figure 26:
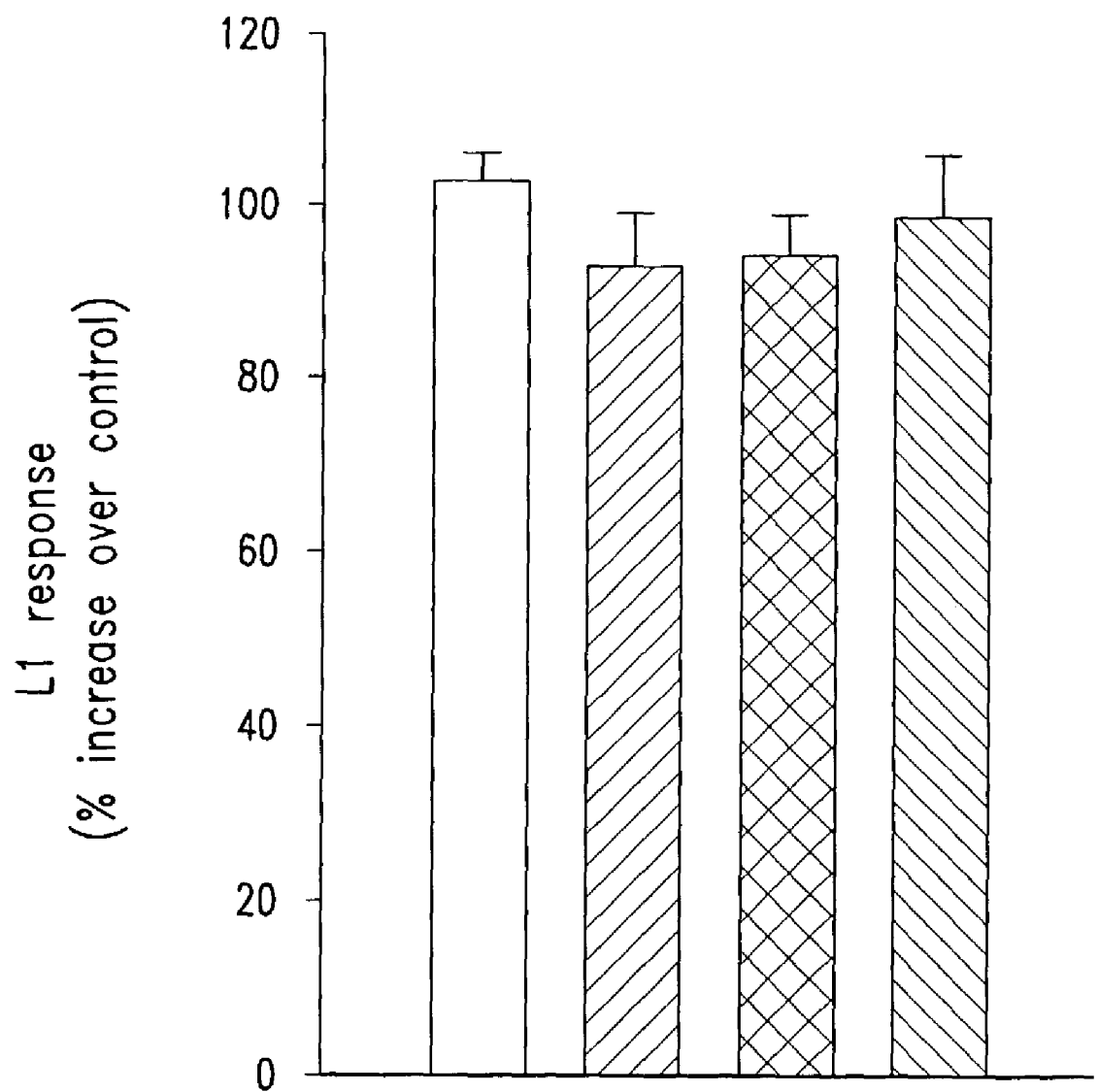
FIG. 26 is a bar graph illustrating the effects of the cyclic peptides N-Ac-CAHVDC-NH$_2$ (SEQ ID NO:11), N-Ac-CAHVDIC-NH$_2$ (SEQ ID NO:62) and N-Ac-CAHVDINC-NH$_2$ (SEQ ID NO:63) on L1 function. Cerebellar neurons were cultured on monolayers of control 3T3 cells and L1 expressing 3T3 cells for 16–18 hours in control media (unshaded) or control media supplemented with peptides N-Ac-CAHVDC-NH$_2$ (SEQ ID NO:11; diagonal rising right), N-Ac-CAHVDIC-NH$_2$ (SEQ ID NO:62); diagonal cross hatch) or N-Ac-CAHVDINC-NH$_2$ (SEQ ID NO:63; diagonal rising left) at a concentration of 100 µg/mL. The cultures were then fixed and neurite outgrowth determined by measuring the length of the longest neurite from a total of 150–200 neurons sampled in replicate cultures for each experimental condition. The results show L1 response, measured as a percentage increase in the mean length of the longest neurite relative to the 3T3 control value, for neurons grown in the absence or presence of the test peptide. The results are pooled from three independent experiments, and the bars show the s.e.m.

Placement of amino acids derived from the N-cadherin sequence on the N-terminus of the HAV sequence appears to either have little affect (compound 7, N-Ac-CAHAVC-NH$_2$; SEQ ID NO:12) or a detrimental affect (e.g., compound 17, N-Ac-CLRAHAVC-NH$_2$; SEQ ID NO:43) on activity. In contrast, addition of an aspartic acid residue on the C-terminus (compound 5, N-Ac-CAHVDC-NH$_2$; SEQ ID NO:11) dramatically increased the inhibitory activity of the peptides (Table 8). Addition of amino acid residues on the N-terminus of the CAR sequence in compound 5 (compound 11, N-Ac-CAHAVDC-NH$_2$, SEQ ID NO:13; compound 17, N-Ac-CRAHAVDC-NH$_2$; SEQ ID NO:15) completely eliminated inhibitory activity. Addition of a second amino acid on the C-terminus (Ile) to yield N-Ac-CAHVDIC-NH$_2$ (compound 33; SEQ ID NO:11) further increased activity from that found for compound 5 and addition of an amino acid to the N-terminus (compound 13, N-Ac-CAHAVDIC-NH$_2$; SEQ ID NO:14) reduced, but did not eliminate, the activity. Again, removal of the N-terminus blocking group to yield H-CAHAVDIC-NH$_2$ (compound 11; SEQ ID NO:14) resulted in total loss of activity. Further extension of the C-terminus to yield N-Ac-CAHVDINC-NH$_2$ (compound 34; SEQ ID NO:63) resulted in only a slight loss in activity as exemplified by the small difference in the $EC_{50}$ values for these two compounds (Table 9). A further addition of a glycine residue (compound 35, N-Ac-CHAVDINGC-NH$_2$ (SEQ ID NO:70) completely abrogates activity. Furthermore, the most active N-cadherin antagonists (N-Ac-CAHVDIC-NH$_2$ (SEQ ID NO:62) $EC_{50}$=0.060 mM, N-Ac-CAHVDINC-NH$_2$ (SEQ ID NO:63), $EC_{50}$=0.070 mM and N-Ac-CAHVDC-NH$_2$ (SEQ ID NO:11), $EC_{50}$=0.093 mM) did not interfere with the ability of neurons to extend neurites over 3T3 cells expressing L1 at concentrations that substantially inhibited the N-cadherin response (FIG. 26).

TABLE 8

Effects of Non-Specific, N-Cadherin Specific and E-Cadherin Specific Antagonists on N-Cadherin Dependent Neurite Outgrowth

| Test Peptide (250 μg/mL) | ID | % Inhibition | Control Peptide (250 μg/mL) | ID | % Inhibition |
|---|---|---|---|---|---|
| Non-Specific | | | | | |
| 1. N-Ac-CHAVC-NH$_2$ | 10 | 68.2 ± 5.1 (4) | 2. N-Ac-CHGVC-NH$_2$ | 20 | 4.8 ± 5.3 |
| 3. H-CHAVC-NH$_2$ | 10 | 1.7 ± 1.1 (3) | 4. H-CHGVC-NH$_2$ | 20 | 7.8 ± 7.1 |
| N-cadherin Specific | | | | | |
| 5. N-Ac-CHAVDC-NH$_2$ | 11 | 88.4 ± 3.7 (3) | 6. N-Ac-CHGVDC-NH$_2$ | 39 | -8.6 ± 5.8 |
| 7. N-Ac-CAHAVC-NH$_2$ | 12 | 58.5 ± 1.0 (3) | 8. N-Ac-CAHGVC-NH$_2$ | 40 | -6.4 ± 5.6 |
| 9. N-Ac-CAHAVDC-NH$_2$ | 13 | 13.3 ± 8.3 (3) | 10. N-Ac-CAHGVDC-NH$_2$ | 46 | 4.0 ± 6.9 |
| 11. H-CAHAVDC-NH$_2$ | 13 | 1.3 ± 13.0 (3) | 12. H-CAHGVDC-NH$_2$ | 46 | 5.7 ± 7.8 |
| 13. N-Ac-CAHAVDIC-NH$_2$ | 14 | 89.4 (2) | 14. N-Ac-CAHGVDIC-NH$_2$ | 41 | 4.8 ± 6.5 |
| 15. H-CAHAVDIC-NH$_2$ | 14 | -3.7 ± 2.9 (3) | 16. H-CAHGVDIC-NH$_2$ | 41 | 7.2 ± 8.1 |
| 17. N-Ac-CLRAHAVC-NH$_2$ | 43 | 9.9 ± 6.6 (3) | 18. N-Ac-CLRAHGVC-NH$_2$ | 44 | -0.5 ± 7.1 |
| 19. N-Ac-CRAHAVDC-NH$_2$ | 15 | -5.0 ± 4.9 (3) | 20. N-Ac-CRAHGVDC-NH$_2$ | 42 | -8.0 ± 6.0 |
| 21. N-Ac-CLRAHAVDC-NH$_2$ | 16 | 76.3 ± 6.6 (3) | 22. N-Ac-CLRAHGVDC-NH$_2$ | 45 | -6.8 ± 6.2 |
| E-cadherin Specific | | | | | |
| 23. N-Ac-CSHAVC-NH$_2$ | 26 | 11.0 ± 8.6 | 24. N-Ac-CSHGVC-NH$_2$ | 47 | 12.5 ± 7.5 |
| 25. N-Ac-CHAVSC-NH$_2$ | 27 | -2.5 ± 7.4 | 26. N-Ac-CHGVSC-NH$_2$ | 48 | -6.7 ± 5.8 |
| 27. N-Ac-CSHAVSC-NH$_2$ | 49 | 8.3 ± 7.3 | 28. N-Ac-CSHGVSC-NH$_2$ | 50 | 10.8 ± 7.6 |
| 29. N-Ac-CSHAVSSC-NH$_2$ | 58 | -12.6 ± 6.4 | 30. N-Ac-CSHGVSSC-NH$_2$ | 51 | -5.6 ± 5.9 |
| 31. N-Ac-CHAVSSC-NH$_2$ | 52 | 34.4 ± 11.3 (3) | 32. N-Ac-CHGVSSC-NH$_2$ | 53 | 14.8 ± 6.5 |

Structure/Activity Relationships for the Inhibition of Neurite Outgrowth with Cyclic HAV-Containing Peptides. In order to further assess the effects of modifying the amino acids flanking the HAV sequence on receptor selectivity, a series of HAV-containing peptides were evaluated for their ability to inhibit neurite outgrowth. These peptides correspond to cyclized sequences derived from the human N-cadherin (RFHLRAHAVDINGN; SEQ ID NO:71) and E-cadherin (TLFSHAVSSNGN; SEQ ID NO:72) sequences immediately adjacent to the surrounding the active site (HAV).

Figure 27:
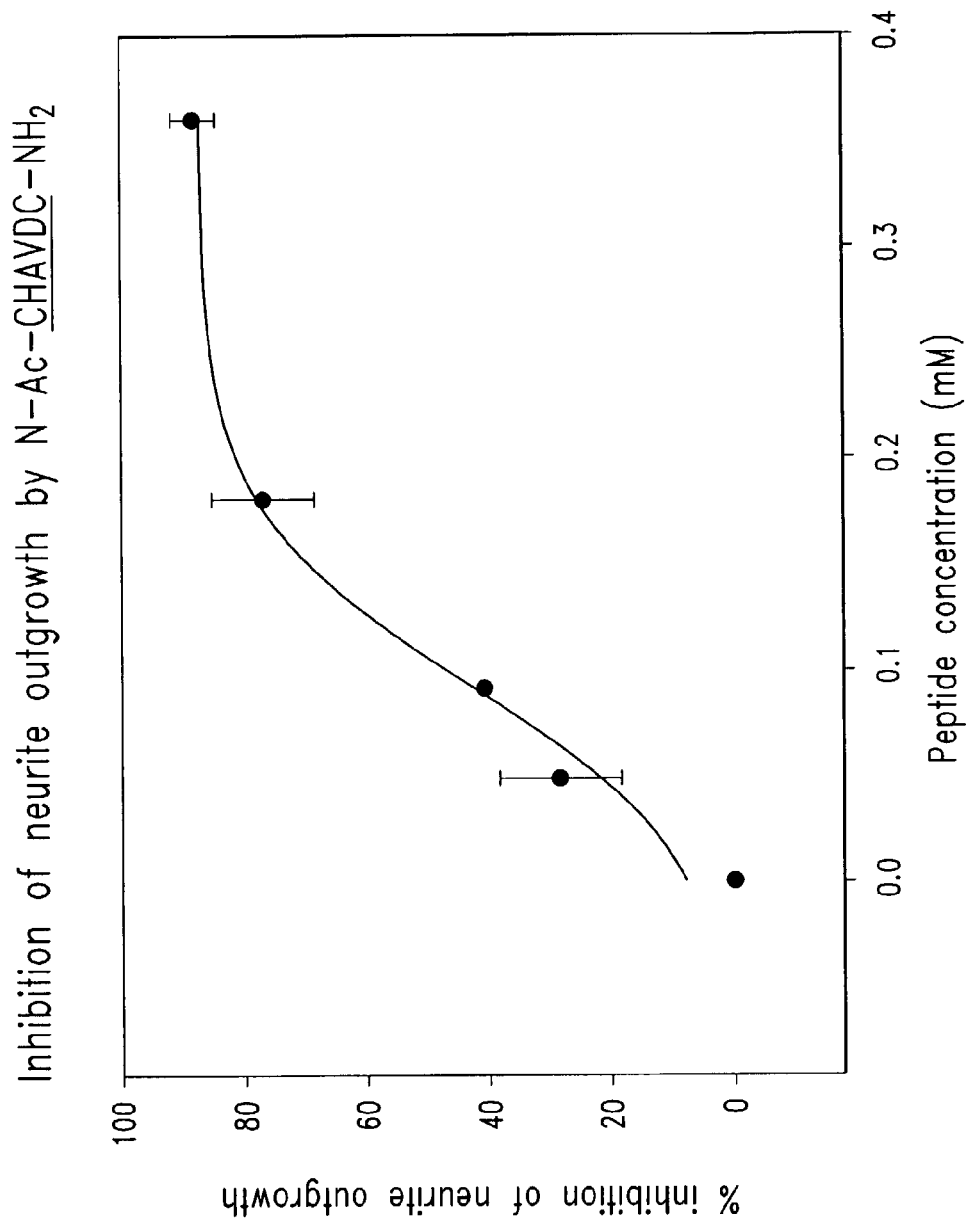
FIG. 27 is a graph dose-response curve that illustrates the inhibition of neurite outgrowth over N-cadherin expressing 3T3 cells in the presence of increasing concentrations of N-Ac-CAHVDC-NH$_2$ (SEQ ID NO:11).
Figure 28:
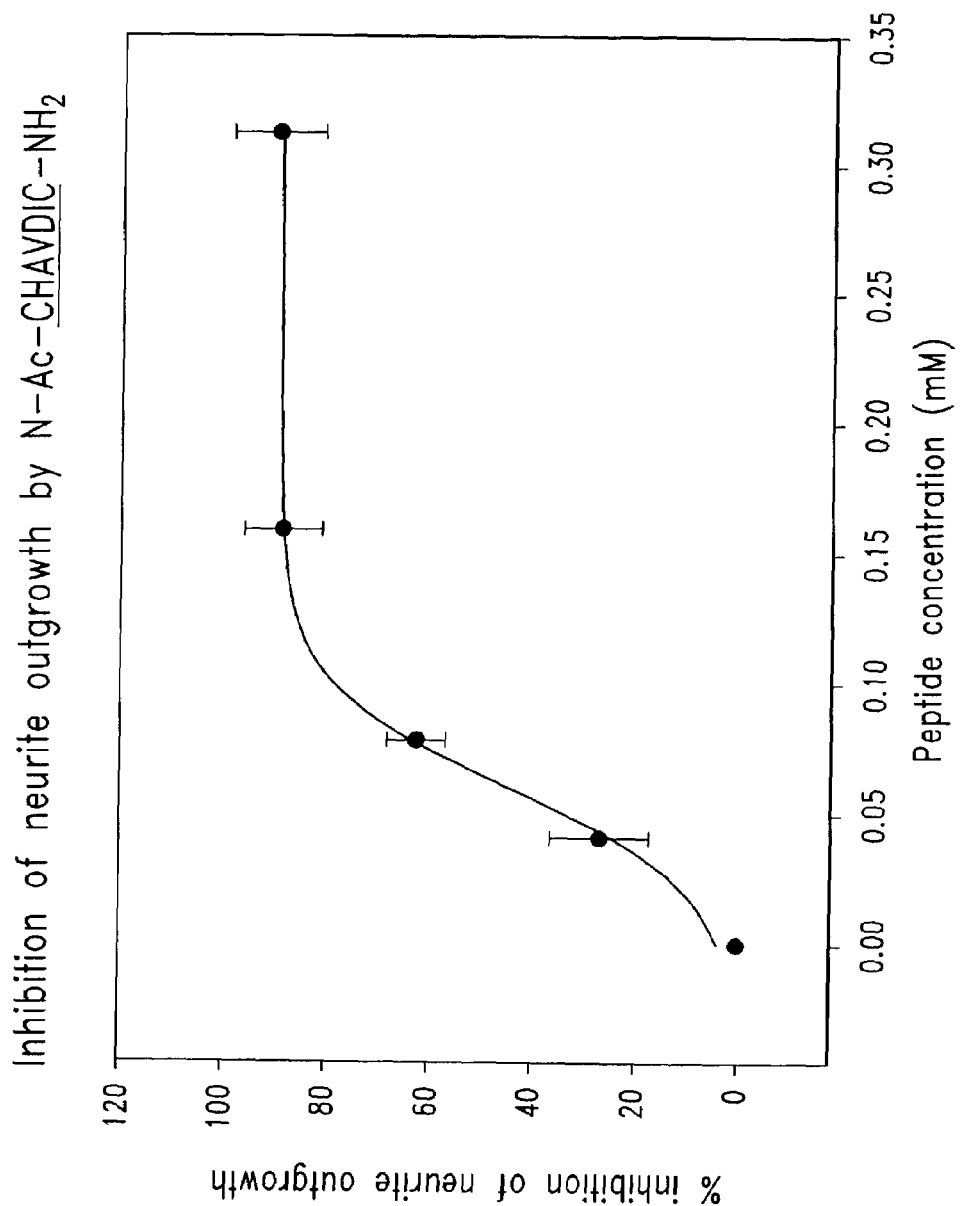
FIG. 28 is a graph dose-response curve that illustrates the inhibition of neurite outgrowth over N-cadherin expressing 3T3 cells in the presence of increasing concentrations of N-Ac-CAHVDIC-NH$_2$ (SEQ ID NO:62).
Figure 29:
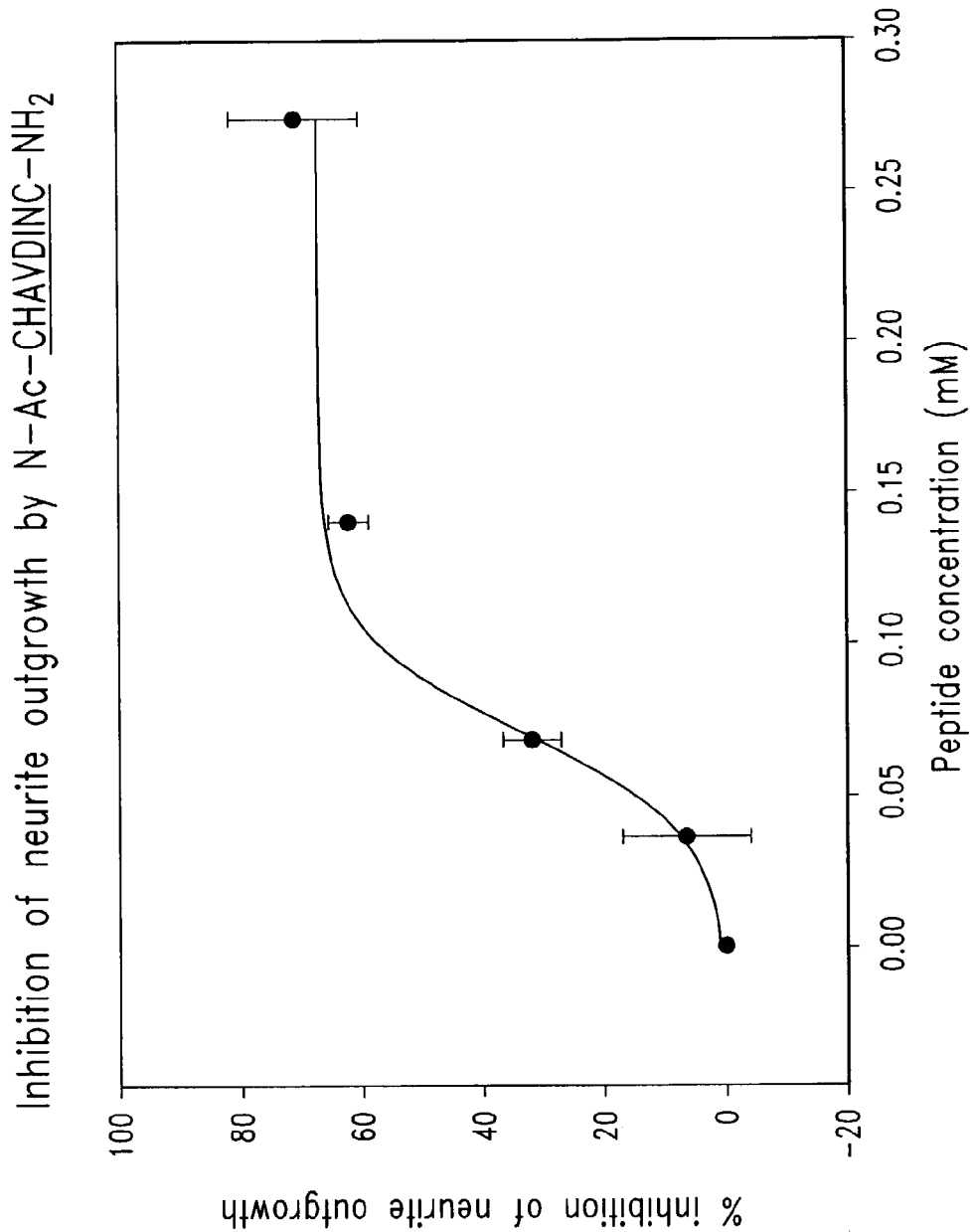
FIG. 29 is a graph dose-response curve that illustrates the inhibition of neurite outgrowth over N-cadherin expressing 3T3 cells in the presence of increasing concentrations of N-Ac-CAHVDINC-NH$_2$ (SEQ ID NO:63).
Figure 30A:
FIGS. 30A–30D are photographs illustrating the ability of a representative cyclic peptide to induce apoptosis in cancer cells. SKOV3 human ovarian cancer cells containing either N-Ac-CHAVC-NH$_2$ (SEQ ID NO:10) or a control peptide (N-Ac-CHGVC-NH$_2$; SEQ ID NO:20) in MEM with 10% FBS were plated onto poly-L-lysine coated glass slides. The cells were cultured for 48 hours and fixed with 4% paraformaldehyde for 30 minutes at room temperature. The slides were then washed three times with PBS and assessed for cell death using the In situ cell death detection kit (Boehringer Mannheim; Laval, Quebec).
Figure 30B:
Figure 30C:
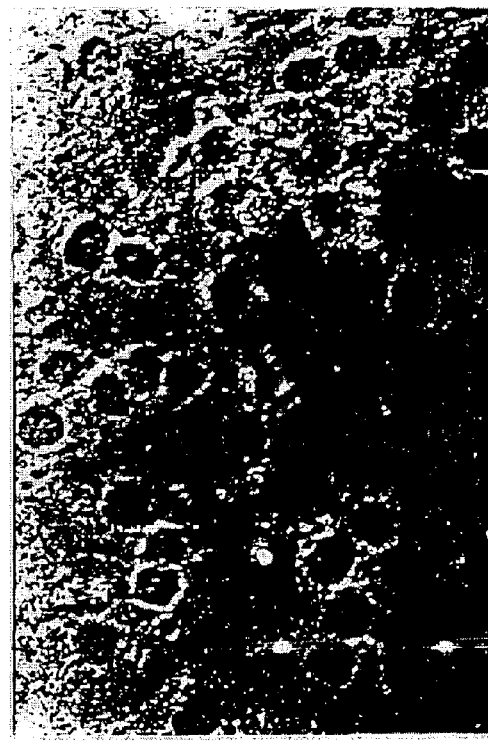
Figure 30D:
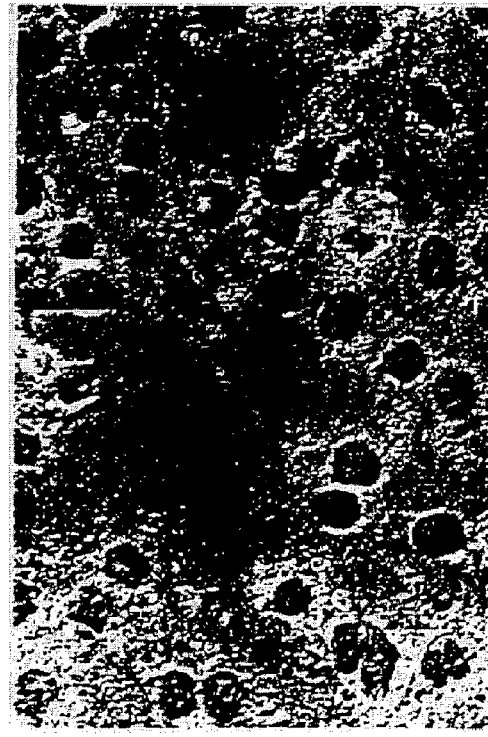
Figure 31:
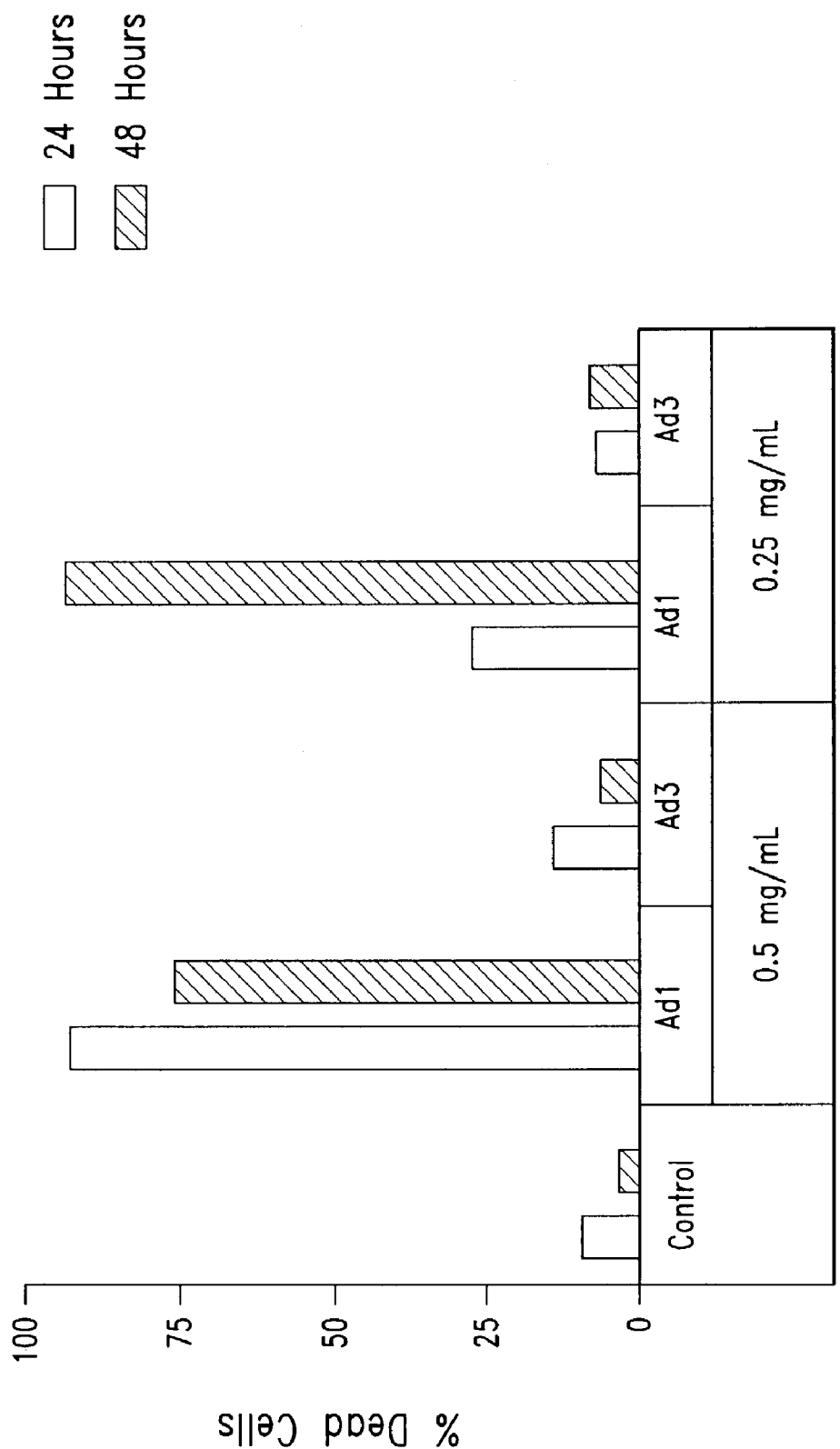
FIG. 31 is a histogram showing the percentage of dead cells following treatment with a representative cyclic peptide or a control peptide. SKOV human ovarian cancer cells containing either N-Ac-CHAVC-NH$_2$ (Ad1; SEQ ID NO:10) or a control peptide (N-Ac-CHGVC-NH$_2$; Ad3; SEQ ID NO:20) in MEM with 10% FBS were plated onto poly-L-lysine coated glass slides. The cells were cultured for 24 or 48 hours and fixed with 4% paraformaldehyde for 30 minutes at room temperature. The slides were then washed three times with PBS and assessed for cell death. Cells were treated with 0.5 or 0.25 mg/mL of N-Ac-CHAVC-NH$_2$ (SEQ ID NO:10) or the control N-Ac-CHGVC-NH$_2$ (SEQ ID NO:20). as indicated. Cell death was measured as described by Gavrieli et al, *J. Cell. Biol.* 119:493–501, 1992 and using the In situ cell death detection kit (Boehringer Mannheim; Laval, Quebec).

The results shown in Table 8 identify four "N-cadherin" peptides (N-Ac-CAHVDC-NH$_2$ (compound 5; SEQ ID NO:11), N-Ac-CAHAVC-NH$_2$ (compound 7; SEQ ID NO:12), N-Ac-CAHAVDIC-NH$_2$ (compound 13; SEQ ID NO:14) and N-Ac-CLRAHAVDC-NH$_2$ (compound 21; SEQ ID NO:16)) which are potent inhibitors of neurite outgrowth when used at a concentration of 250 μg/mL. All of these peptides except peptide N-Ac-CAHVDC-NH$_2$ (SEQ ID NO:11) lost activity at concentrations of 125 mg/mL or below. A dose response curve (FIG. 27) for N-Ac-CAHVDC-NH$_2$ (SEQ ID NO:11) indicated that significant activity remained at 33 μg/mL (% inhibition 28.5+/−10) and an EC$_{50}$ value of 0.093 mM was obtained. These results indicated that the aspartic acid on the carboxy terminus of the HAV motif was likely a key residue for N-cadherin receptor binding. To further explore the influence of the C-terminus residues on activity, N-Ac-CAHVDIC-NH$_2$ (compound 33; SEQ ID NO:62), N-Ac-CAHVDINC-NH$_2$ (compound 34; SEQ ID NO:63) and N-Ac-CHAVDINGC-NH$_2$ (compound 35; SEQ ID NO:70) were synthesized. Both N-Ac-CAHVDIC-NH$_2$ (SEQ ID NO:62) and N-Ac-CAHVDINC-NH$_2$ (SEQ ID NO:63) turned out to be potent inhibitors (Table 9) and dose response curves for these two compounds yield EC$_{50}$ values of 0.060 mM (FIG. 28) and 0.070 mM (FIG. 29), respectively.

TABLE 9

Effect of Additional C-terminal Residues on Neurite Outgrowth

| Test Peptide (125 μg/mL) | SEQ ID NO. | % Inhibition | EC$_{50}$ (mM) |
|---|---|---|---|
| 5. N-Ac-CHAVDC-NH$_2$ | 11 | 77.1 ± 8.4 | 0.093 |
| 33. N-Ac-CHAVDIC-NH$_2$ | 62 | 88.3 ± 7.5 | 0.060 |
| 34. N-Ac-CHAVDINC-NH$_2$ | 63 | 62.0 ± 3.4 | 0.070 |
| 35. N-Ac-CHAVDINGC-NH$_2$ | 70 | 1.5 ± 2.2 | |

Interestingly, flanking of the HAV motif with amino acids found in human E-cadherin sequence resulted in either a complete (peptides 23, 25, 27 and 29) or substantial (peptide 31) reduction in inhibitory activity (Table 8). In addition, a series of corresponding control peptides, in which the HAV sequence had been replaced by HGV, were also tested in the screen. All sixteen control peptides failed to inhibit the N-cadherin response (see Table 8). Finally, if the N-terminal blocking group was removed these peptides lost activity (Table 8, compounds 3, 15).

Effects of HAV-containing peptides on the L1 response. Other cell adhesion molecules, such as L1, can stimulate neurite outgrowth, and this response shares the same downstream signaling steps as the N-cadherin response. In order to ascertain the specificity of the most active N-cadherin antagonists (N-Ac-CAHVDC-$NH_2$ (compound 5; SEQ ID NO:11), N-Ac-CAHVDIC-$NH_2$ (compound 33; SEQ ID NO:62) and N-Ac-CAHVDINC-$NH_2$ (compound 34; SEQ ID NO:63), cerebellar neurons were cultured over either control 3T3 cell monolayers, or monolayers of 3T3 cells stably transfected with cDNA encoding L1 in the presence and absence of each peptide. As previously reported, L1 stimulated neurite outgrowth from cerebellar neurons. This response was not inhibited by any of the above cyclic peptides at concentrations that prevented N-cadherin-mediated neurite outgrowth (FIG. 26).

These results demonstrate that cyclic HAV peptides containing flanking amino acids found in N-cadherin are potent inhibitors of neurite outgrowth, whereas cyclic HAV-containing peptides containing flanking amino acids found in E-cadherin are inactive for such purposes. In addition, specificity for the N-cadherin receptor can be built into the peptides by adding flanking amino acids derived from native N-cadherin to the C-terminus, while addition of one or two amino acid residues on the N-terminus appears to be detrimental to activity (addition of a third amino acid on the N-terminus to give N-Ac-CLRAHAVDC-$NH_2$ (compound 21; SEQ ID NO:16) resulted in partial recovery of activity). Collectively, these results show that the information needed for non-specific cadherin binding resides in the HAV sequence, whereas the role of the surrounding amino acids is to constrain the side chains of His and Val into a conformation required for specific cadherin (e.g., N-cadherin) recognition.

EXAMPLE 15

Expression of N-cadherin in Metastatic Carcinoma Cells

This Example illustrates the correlation between N-cadherin and metastatic potential in ovarian carcinoma cell lines.

E-cadherin and N-cadherin expression was evaluated in a series of ovarian carcinoma cell lines, using the RT-PCR approach described above. The E-cadherin specific primer used were:

Forward 5'-CCTTCCCCCAACACGTCCCCCC-3' (SEQ ID NO:73); and

Reverse 5'-TCTCCACCTCCTTCTTCATC-3' (SEQ ID NO:74)

(Munro and Blaschuk, *Biol. Reprod.* 55:822–827, 1996). The N-cadherin specific primers used were:

Forward 5'-CAAGAGCTTGTCACAATCAGG-3' (SEQ ID NO:75); and

Reverse 5'-CATTTGGATCATCCGCATC-3' (SEQ ID NO:76)

(Munro and Blaschuk, *Biol. Reprod.* 55:822–827, 1996).

Cell lines examined included OVCAR-3 (Hamilton et al., *Cancer Research* 43:5379–89,1983); SW626 (Ripamonti et al., *Cancer Immunology, Immunotherapy* 24:13–18, 1987); CaOV3, SKOV3 and HEY (Buick et al., *Cancer Research* 45:3668–76, 1985). These cells (except HEY) are also available from American Type Culture Collection (Manassas, Va.).

The results of these analyses are presented in Table 10, below, in which detectable PCR product is indicated as a "+" and no detectable PCR product is indicated by a "–".

TABLE 10

N- and E-Cadherin Expression in Ovarian Carcinoma Cell Lines

| Cell Line | Phenotype | Differentiation Stage and Metastatic Potential | Cadherin E | Cadherin N |
|---|---|---|---|---|
| Normal | Epithelial | None | + | – |
| OVCAR-3 | Adenocarcinoma | Differentiated; low metastatic | + | – |
| SW626 | Adenocarcinoma | Differentiated; low metastatic | + | – |
| CaOV3 | Adenocarcinoma | ? | + | + |
| SKOV3 | Adenocarcinoma | Poor differentiation; high metastatic | – | + |
| HEY | Adenocarcinoma | Poor differentiation; high metastatic | – | + |

EXAMPLE 16

Induction of Apoptosis in Cancer Cells

This Example illustrates the use of a representative modulating agent for killing human ovarian cancer cells.

SKOV3 human ovarian cancer cells cultured in the presence of either N-Ac-CHAVC-$NH_2$ (SEQ ID NO:10) or a control peptide (N-Ac-CHGVC-$NH_2$; SEQ ID NO:20) in MEM with 10% FBS were plated onto poly-L-lysine coated glass slides. The cells were cultured for 24 or 48 hours and fixed with 4% paraformaldehyde for 30 minutes at room temperature. The slides were then washed three times with PBS and assessed for cell death. Cells were treated with 0.5 or 0.25 mg/mL of N-Ac-CHAVC-$NH_2$ (SEQ ID NO:10) or the control N-Ac-CHGVC-$NH_2$ (SEQ ID NO:20), as indicated. Cell death was measured as described by Gavrieli et al, *J. Cell. Biol.* 119:493–501, 1992 and using the In situ cell death detection kit (Boehringer Mannheim; Laval, Quebec).

FIGS. 30A–30D show the results of such an assay, in which the cells were treated with the peptides for 48 hours. The fluorescent green nuclei evident in FIGS. 30C and 30D (cells treated with N-Ac-CHAVC-$NH_2$ (SEQ ID NO:10)) indicate that the cells are dead. In contrast, cells treated with the control peptide (FIGS. 30A and 30B) did not die. A bar graph further illustrating the ability of N-Ac-CHAVC-$NH_2$ (SEQ ID NO:10) to induce apoptosis is shown in FIG. 31. These observations indicate that this cyclic peptide can cause human ovarian cancer cell death.

From the foregoing, it will be evident that although specific embodiments of the invention have been described herein for the purpose of illustrating the invention, various modifications may be made without deviating from the spirit and scope of the invention. Accordingly, the present invention is not limited except as by the appended claims.

What is claimed is:

1. A method for inducing apoptosis in a classical cadherin-expressing cell, comprising contacting a classical cadherin-expressing cell with a modulating agent that comprises a cyclic peptide in which nonadjacent amino acid residues are covalently linked to form a peptide ring, wherein the peptide ring comprises the sequence His-Ala-Val and contains from 4 to 15 amino acid residues.

2. A method according to claim 1, wherein the cyclic peptide has the formula:

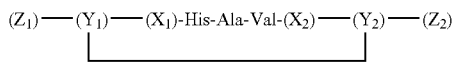

wherein $X_1$, and $X_2$ are optional, and if present, are independently selected from the group consisting of amino acid residues and combinations thereof in which the residues are linked by peptide bonds, and wherein $X_1$ and $X_2$ independently range in size from 0 to 10 residues, such that the sum of residues contained within $X_1$ and $X_2$ ranges from 1 to 12;

wherein $Y_1$ and $Y_2$ are independently selected from the group consisting of amino acid residues, and wherein a covalent bond is formed between residues $Y_1$ and $Y_2$; and wherein $Z_1$ and $Z_2$ are optional, and if present, are independently selected from the group consisting of amino acid residues and combinations thereof in which the residues are linked by peptide bonds.

3. A method according to claim 2, wherein $Z_1$ is not present and $Y_1$ comprises an N-acetyl group.

4. A method according to claim 2, wherein $Z_2$ is not present and $Y_2$ comprises a C-terminal amide group.

5. A method according to claim 2, wherein $Y_1$ and $Y_2$ are covalently linked via a disulfide bond.

6. A method according to claim 5, wherein $Y_1$ and $Y_2$ are each independently selected from the group consisting of penicillamine, β,β-tetramethylene cysteine, β,β-pentamethylene cysteine, β-mercaptopropionic acid, β,β-pentamethylene-β-mercaptopropionic acid, 2-mercaptobenzene, 2-mercaptoaniline, 2-mercaptoproline and derivatives thereof.

7. A method according to claim 5, wherein $Y_1$ and $Y_2$ are cysteine residues or derivatives thereof.

8. A method according to claim 2, wherein $Y_1$ and $Y_2$ are covalently linked via an amide bond.

9. A method according to claim 8, wherein the amide bond is formed is formed between terminal functional groups.

10. A method according to claim 8, wherein the amide bond is formed between residue side-chains.

11. A method according to claim 8, wherein the amide bond is formed between one terminal functional group and one residue side chain.

12. A method according to claim 8, wherein:
   (a) $Y_1$ is selected from the group consisting of lysine, ornithine, and derivatives thereof and $Y_2$ is selected from the group consisting of aspartate, glutamate and derivatives thereof, or
   (b) $Y_2$ is selected from the group consisting of lysine, ornithine and derivatives thereof and $Y_1$ is selected from the group consisting of aspartate, glutamate and derivatives thereof.

13. A method according to claim 2, wherein $Y_1$ and $Y_2$ are covalently linked via a thioether bond.

14. A method according to claim 2, wherein $Y_1$ and $Y_2$ are each tryptophan or a derivative thereof, such that the covalent bond generates a $δ_1,δ_1$-ditryptophan, or a derivative thereof.

15. A method according to claim 1, wherein the modulating agent comprises a sequence selected from the group consisting of CHAVC (SEQ ID NO:10), CHAVDC (SEQ ID NO:11), CHAVDIC (SEQ ID NO:62), CHAVDINC (SEQ ID NO:63), CHAVDINGC (SEQ ID NO:70), CAHAVC (SEQ ID NO:12), CAHAVDC (SEQ ID NO:36), CAHAVDIC (SEQ ID NO:14), CRAHAVDC (SEQ ID NO:15), CLRAHAVC (SEQ ID NO:43), CLRAHAVDC (SEQ ID NO:16), CSHAVC (SEQ ID NO:26), CHAVSC (SEQ ID NO:27), CSHAVSC (SEQ ID NO:49), CSHAVSSC (SEQ ID NO:28), CHAVSSC (SEQ ID NO:52), KHAVD (SEQ ID NO:37), DHAVK (SEQ ID NO:17),KHAVE (SEQ ID NO:18), AHAVDI (SEQ ID NO:19), SHAVDSS (SEQ ID NO:78), KSHAVSSD (SEQ ID NO:60) and derivatives of the foregoing sequences having one or more C-terminal, N-terminal and/or side chain modifications.

16. A method according to claim 1, wherein the classical cadherin is N-cadherin.

17. A method according to claim 1, wherein the modulating agent is linked to a drug.

18. A method according to claim 1, wherein the modulating agent is linked to a targeting agent.

19. A method according to claim 1, wherein the modulating agent further comprises one or more of:
   (a) a cell adhesion recognition sequence that is bound by an adhesion molecule other than a classical cadherin, wherein the cell adhesion recognition sequence is separated from any HAV sequence(s) by a linker; and/or
   (b) an antibody or antigen-binding fragment thereof that specifically binds to a cell adhesion recognition sequence bound by an adhesion molecule other than a classical cadherin.

20. A method according to claim 19, wherein the cell adhesion recognition sequence is selected from the group consisting of RGD, DDK, EEY, EAQ, NQK, NRN, NKD, EKD, ERD and LYHY (SEQ ID NO:64).

21. A method according to claim 1, wherein the modulating agent is present within a pharmaceutical composition that comprises a pharmaceutically acceptable carrier.

22. A method according to claim 21, wherein the composition further comprises a drug.

23. A method according to claim 21, wherein the cell adhesion modulating agent is present within a sustained-release formulation.

24. A method according to claim 21, wherein the pharmaceutical composition further comprises one or more of:
   (a) a modulator of cell adhesion comprising a cell adhesion recognition sequence that is bound by an adhesion molecule other than a classical cadherin; and/or
   (b) an antibody or antigen-binding fragment thereof that specifically binds to a cell adhesion recognition sequence bound by an adhesion molecule other than a classical cadherin.

25. A method according to claim 24, wherein the cell adhesion recognition sequence is selected from the group consisting of RGD, DDK, EEY, EAQ, NQK, NRN, NKD, EKD, ERD and LYHY (SEQ ID NO:64).

26. A method according to claim 1, wherein the cadherin-expressing cell is a cancer cell.

27. A method according to claim 1, wherein the cancer cell is present within a patient, and wherein the step of contacting is performed by administering the modulating agent to the patient.

28. A method according to claim 27, wherein the modulating agent is administered topically to a tumor in the patient.

29. A method according to claim 27, wherein the modulating agent is administered systemically.

* * * * *

SEQUENCE LISTING

```
<160> NUMBER OF SEQ ID NOS: 81
<210> SEQ ID NO 1
<211> LENGTH: 108
<212> TYPE: PRT
<213> ORGANISM: Homo sapiens

<400> SEQUENCE: 1
```

Asp Trp Val Ile Pro Pro Ile Asn Leu Pro Glu Asn Ser Arg Gly Pro
1               5                   10                  15

Phe Pro Gln Glu Leu Val Arg Ile Arg Ser Asp Arg Asp Lys Asn Leu
            20                  25                  30

Ser Leu Arg Tyr Ser Val Thr Gly Pro Gly Ala Asp Gln Pro Pro Thr
        35                  40                  45

Gly Ile Phe Ile Leu Asn Pro Ile Ser Gly Gln Leu Ser Val Thr Lys
    50                  55                  60

Pro Leu Asp Arg Glu Gln Ile Ala Arg Phe His Leu Arg Ala His Ala
65                  70                  75                  80

Val Asp Ile Asn Gly Asn Gln Val Glu Asn Pro Ile Asp Ile Val Ile
                85                  90                  95

Asn Val Ile Asp Met Asn Asp Asn Arg Pro Glu Phe
            100                 105

```
<210> SEQ ID NO 2
<211> LENGTH: 108
<212> TYPE: PRT
<213> ORGANISM: Mus musculus

<400> SEQUENCE: 2
```

Asp Trp Val Ile Pro Pro Ile Asn Leu Pro Glu Asn Ser Arg Gly Pro
1               5                   10                  15

Phe Pro Gln Glu Leu Val Arg Ile Arg Ser Asp Arg Asp Lys Asn Leu
            20                  25                  30

Ser Leu Arg Tyr Ser Val Thr Gly Pro Gly Ala Asp Gln Pro Pro Thr
        35                  40                  45

Gly Ile Phe Ile Ile Asn Pro Ile Ser Gly Gln Leu Ser Val Thr Lys
    50                  55                  60

Pro Leu Asp Arg Glu Leu Ile Ala Arg Phe His Leu Arg Ala His Ala
65                  70                  75                  80

Val Asp Ile Asn Gly Asn Gln Val Glu Asn Pro Ile Asp Ile Val Ile
                85                  90                  95

Asn Val Ile Asp Met Asn Asp Asn Arg Pro Glu Phe
            100                 105

```
<210> SEQ ID NO 3
<211> LENGTH: 108
<212> TYPE: PRT
<213> ORGANISM: Bos taurus

<400> SEQUENCE: 3
```

Asp Trp Val Ile Pro Pro Ile Asn Leu Pro Glu Asn Ser Arg Gly Pro
1               5                   10                  15

Phe Pro Gln Glu Leu Val Arg Ile Arg Ser Asp Arg Asp Lys Asn Leu
            20                  25                  30

Ser Leu Arg Tyr Ser Val Thr Gly Pro Gly Ala Asp Gln Pro Pro Thr
        35                  40                  45

Gly Ile Phe Ile Ile Asn Pro Ile Ser Gly Gln Leu Ser Val Thr Lys

```
                50              55              60
Pro Leu Asp Arg Glu Leu Ile Ala Arg Phe His Leu Arg Ala His Ala
 65                  70                  75                  80

Val Asp Ile Asn Gly Asn Gln Val Asn Pro Ile Asp Ile Val Ile
                 85                  90                  95

Asn Val Ile Asp Met Asn Asp Asn Arg Pro Glu Phe
            100                 105

<210> SEQ ID NO 4
<211> LENGTH: 108
<212> TYPE: PRT
<213> ORGANISM: Homo sapiens

<400> SEQUENCE: 4

Asp Trp Val Val Ala Pro Ile Ser Val Pro Glu Asn Gly Lys Gly Pro
  1               5                  10                  15

Phe Pro Gln Arg Leu Asn Gln Leu Lys Ser Asn Lys Asp Arg Asp Thr
             20                  25                  30

Lys Ile Phe Tyr Ser Ile Thr Gly Pro Gly Ala Asp Ser Pro Pro Glu
         35                  40                  45

Gly Val Phe Ala Val Glu Lys Glu Thr Gly Trp Leu Leu Leu Asn Lys
 50                  55                  60

Pro Leu Asp Arg Glu Glu Ile Ala Lys Tyr Glu Leu Phe Gly His Ala
 65                  70                  75                  80

Val Ser Glu Asn Gly Ala Ser Val Glu Asp Pro Met Asn Ile Ser Ile
                 85                  90                  95

Ile Val Thr Asp Gln Asn Asp His Lys Pro Lys Phe
            100                 105

<210> SEQ ID NO 5
<211> LENGTH: 108
<212> TYPE: PRT
<213> ORGANISM: Mus musculus

<400> SEQUENCE: 5

Glu Trp Val Met Pro Pro Ile Phe Val Pro Glu Asn Gly Lys Gly Pro
  1               5                  10                  15

Phe Pro Gln Arg Leu Asn Gln Leu Lys Ser Asn Lys Asp Arg Gly Thr
             20                  25                  30

Lys Ile Phe Tyr Ser Ile Thr Gly Pro Gly Ala Asp Ser Pro Pro Glu
         35                  40                  45

Gly Val Phe Thr Ile Glu Lys Glu Ser Gly Trp Leu Leu Leu His Met
 50                  55                  60

Pro Leu Asp Arg Glu Lys Ile Val Lys Tyr Glu Leu Tyr Gly His Ala
 65                  70                  75                  80

Val Ser Glu Asn Gly Ala Ser Val Glu Glu Pro Met Asn Ile Ser Ile
                 85                  90                  95

Ile Val Thr Asp Gln Asn Asp Asn Lys Pro Lys Phe
            100                 105

<210> SEQ ID NO 6
<211> LENGTH: 108
<212> TYPE: PRT
<213> ORGANISM: Homo sapiens

<400> SEQUENCE: 6

Asp Trp Val Ile Pro Pro Ile Ser Cys Pro Glu Asn Glu Lys Gly Pro
  1               5                  10                  15
```

-continued

```
Phe Pro Lys Asn Leu Val Gln Ile Lys Ser Asn Lys Asp Lys Glu Gly
            20                  25                  30

Lys Val Phe Tyr Ser Ile Thr Gly Gln Gly Ala Asp Thr Pro Pro Val
        35                  40                  45

Gly Val Phe Ile Ile Glu Arg Glu Thr Gly Trp Leu Lys Val Thr Glu
    50                  55                  60

Pro Leu Asp Arg Glu Arg Ile Ala Thr Tyr Thr Leu Phe Ser His Ala
65                  70                  75                  80

Val Ser Ser Asn Gly Asn Ala Val Glu Asp Pro Met Glu Ile Leu Ile
                85                  90                  95

Thr Val Thr Asp Gln Asn Asp Asn Lys Pro Glu Phe
            100                 105

<210> SEQ ID NO 7
<211> LENGTH: 108
<212> TYPE: PRT
<213> ORGANISM: Mus musculus

<400> SEQUENCE: 7

Asp Trp Val Ile Pro Pro Ile Ser Cys Pro Glu Asn Glu Lys Gly Glu
1               5                   10                  15

Phe Pro Lys Asn Leu Val Gln Ile Lys Ser Asn Arg Asp Lys Glu Thr
            20                  25                  30

Lys Val Phe Tyr Ser Ile Thr Gly Gln Gly Ala Asp Lys Pro Pro Val
        35                  40                  45

Gly Val Phe Ile Ile Glu Arg Glu Thr Gly Trp Leu Lys Val Thr Gln
    50                  55                  60

Pro Leu Asp Arg Glu Ala Ile Ala Lys Tyr Ile Leu Tyr Ser His Ala
65                  70                  75                  80

Val Ser Ser Asn Gly Glu Ala Val Glu Asp Pro Met Glu Ile Val Ile
                85                  90                  95

Thr Val Thr Asp Gln Asn Asp Asn Arg Pro Glu Phe
            100                 105

<210> SEQ ID NO 8
<211> LENGTH: 5
<212> TYPE: PRT
<213> ORGANISM: Unknown
<220> FEATURE:
<221> NAME/KEY: MOD_RES
<222> LOCATION: (2)
<223> OTHER INFORMATION: Where Xaa is any amino acid
<220> FEATURE:
<223> OTHER INFORMATION: Description of Unknown Organism: Cadherin
      Calcium Binding Motif

<400> SEQUENCE: 8

Asp Xaa Asn Asp Asn
1               5

<210> SEQ ID NO 9
<211> LENGTH: 4
<212> TYPE: PRT
<213> ORGANISM: Unknown
<220> FEATURE:
<223> OTHER INFORMATION: Description of Unknown Organism: Cadherin
      Calcium Binding Motif

<400> SEQUENCE: 9

Leu Asp Arg Glu
1
```

-continued

```
<210> SEQ ID NO 10
<211> LENGTH: 5
<212> TYPE: PRT
<213> ORGANISM: Artificial Sequence
<220> FEATURE:
<223> OTHER INFORMATION: Description of Artificial Sequence: Cyclic
      Peptide with Classical Cell Adhesion Recognition Sequence
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 10

Cys His Ala Val Cys
 1               5

<210> SEQ ID NO 11
<211> LENGTH: 6
<212> TYPE: PRT
<213> ORGANISM: Artificial Sequence
<220> FEATURE:
<223> OTHER INFORMATION: Description of Artificial Sequence:  Cyclic
      peptide with classical cadherin cell adhesion
      recognition sequence
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 11

Cys His Ala Val Asp Cys
 1               5

<210> SEQ ID NO 12
<211> LENGTH: 6
<212> TYPE: PRT
<213> ORGANISM: Artificial Sequence
<220> FEATURE:
<223> OTHER INFORMATION: Description of Artificial Sequence:  Cyclic
      peptide with classical cadherin cell adhesion
      recognition sequence
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 12

Cys Ala His Ala Val Cys
 1               5

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence:  Cyclic
      peptide with classical cadherin cell adhesion
      recognition sequence
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 13

Cys Ala His Ala Val Asp Cys
 1               5
```

```
<210> SEQ ID NO 14
<211> LENGTH: 8
<212> TYPE: PRT
<213> ORGANISM: Artificial Sequence
<220> FEATURE:
<223> OTHER INFORMATION: Description of Artificial Sequence:  Cyclic
      peptide with classical cadherin cell adhesion
      recognition sequence
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 14

Cys Ala His Ala Val Asp Ile Cys
 1               5

<210> SEQ ID NO 15
<211> LENGTH: 8
<212> TYPE: PRT
<213> ORGANISM: Artificial Sequence
<220> FEATURE:
<223> OTHER INFORMATION: Description of Artificial Sequence:  Cyclic
      peptide with classical cadherin cell adhesion
      recognition sequence
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 15

Cys Arg Ala His Ala Val Asp Cys
 1               5

<210> SEQ ID NO 16
<211> LENGTH: 9
<212> TYPE: PRT
<213> ORGANISM: Artificial Sequence
<220> FEATURE:
<223> OTHER INFORMATION: Description of Artificial Sequence:  Cyclic
      peptide with classical cadherin cell adhesion
      recognition sequence
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 16

Cys Leu Arg Ala His Ala Val Asp Cys
 1               5

<210> SEQ ID NO 17
<211> LENGTH: 5
<212> TYPE: PRT
<213> ORGANISM: Artificial Sequence
<220> FEATURE:
<223> OTHER INFORMATION: Description of Artificial Sequence:  Cyclic
      peptide with cadherin cell adhesion recognition
      sequence
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 17

Asp His Ala Val Lys
```

-continued

<210> SEQ ID NO 18
<211> LENGTH: 5
<212> TYPE: PRT
<213> ORGANISM: Artificial Sequence
<220> FEATURE:
<223> OTHER INFORMATION: Description of Artificial Sequence: Cyclic
      peptide with classical cadherin cell adhesion
      recognition sequence
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 18

Lys His Ala Val Glu
 1               5

<210> SEQ ID NO 19
<211> LENGTH: 6
<212> TYPE: PRT
<213> ORGANISM: Artificial Sequence
<220> FEATURE:
<223> OTHER INFORMATION: Description of Artificial Sequence: Cyclic
      peptide with classical cadherin cell adhesion
      recognition sequence
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 19

Ala His Ala Val Asp Ile
 1               5

<210> SEQ ID NO 20
<211> LENGTH: 5
<212> TYPE: PRT
<213> ORGANISM: Artificial Sequence
<220> FEATURE:
<223> OTHER INFORMATION: Description of Artificial Sequence: Cyclic
      control peptide
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 20

Cys His Gly Val Cys
 1               5

<210> SEQ ID NO 21
<211> LENGTH: 5
<212> TYPE: PRT
<213> ORGANISM: Unknown
<220> FEATURE:
<223> OTHER INFORMATION: Description of Unknown Organism: Cadherin cell
      adhesion recognition sequencebound by
      alpha-6-beta-1 integrin

<400> SEQUENCE: 21

Tyr Ile Gly Ser Arg
 1               5

<210> SEQ ID NO 22
<211> LENGTH: 10

```
<212> TYPE: PRT
<213> ORGANISM: Unknown
<220> FEATURE:
<223> OTHER INFORMATION: Description of Unknown Organism: Cadherin cell
      adhesion recognition sequence bound by N-CAM

<400> SEQUENCE: 22

Lys Tyr Ser Phe Asn Tyr Asp Gly Ser Glu
 1               5                  10

<210> SEQ ID NO 23
<211> LENGTH: 10
<212> TYPE: PRT
<213> ORGANISM: Artificial Sequence
<220> FEATURE:
<223> OTHER INFORMATION: Description of Artificial Sequence:
      Synthesized Peptide
<220> FEATURE:
<221> NAME/KEY: MOD_RES
<222> LOCATION: (1)
<223> OTHER INFORMATION: BLOCKED by 9-fluorenymethyloxycarbonyl
<220> FEATURE:
<221> NAME/KEY: MOD_RES
<222> LOCATION: (2)
<223> OTHER INFORMATION: tert-butyl protecting group
<220> FEATURE:
<221> NAME/KEY: MOD_RES
<222> LOCATION: (4)
<223> OTHER INFORMATION: tert-butyl protecting group
<220> FEATURE:
<221> NAME/KEY: MOD_RES
<222> LOCATION: (6)
<223> OTHER INFORMATION: t-Butoxycarbonyl protecting group
<220> FEATURE:
<221> NAME/KEY: MOD_RES
<222> LOCATION: (7)
<223> OTHER INFORMATION: tert-butyl protecting group
<220> FEATURE:
<221> NAME/KEY: MOD_RES
<222> LOCATION: (9)
<223> OTHER INFORMATION: tert-butyl protecting group
<220> FEATURE:
<221> NAME/KEY: MOD_RES
<222> LOCATION: (10)
<223> OTHER INFORMATION: Methoxy terminal group

<400> SEQUENCE: 23

Cys Asp Gly Tyr Pro Lys Asp Cys Lys Gly
 1               5                  10

<210> SEQ ID NO 24
<211> LENGTH: 10
<212> TYPE: PRT
<213> ORGANISM: Artificial Sequence
<220> FEATURE:
<223> OTHER INFORMATION: Description of Artificial Sequence:
      Synthesized peptide
<220> FEATURE:
<221> NAME/KEY: MOD_RES
<222> LOCATION: (1)
<223> OTHER INFORMATION: Residue has t-butoxycarbonyl, and Trityl or
      Acetamidomethyl protecting groups
<220> FEATURE:
<221> NAME/KEY: MOD_RES
<222> LOCATION: (5)..(6)
<223> OTHER INFORMATION: tert-butyl protecting group
<220> FEATURE:
<221> NAME/KEY: MOD_RES
<222> LOCATION: (7)
<223> OTHER INFORMATION: Trityl or acetaminomethly protecting group

<400> SEQUENCE: 24

Cys Gly Asn Leu Ser Thr Cys Met Leu Gly
 1               5                  10
```

```
<210> SEQ ID NO 25
<211> LENGTH: 9
<212> TYPE: PRT
<213> ORGANISM: Artificial Sequence
<220> FEATURE:
<223> OTHER INFORMATION: Description of Artificial Sequence:
      Synthesized peptide
<220> FEATURE:
<221> NAME/KEY: MOD_RES
<222> LOCATION: (2)
<223> OTHER INFORMATION: Residue has Acetamidomethyl or
      tert-Acetaminomethyl or tert-butyl protecting
      group
<220> FEATURE:
<221> NAME/KEY: MOD_RES
<222> LOCATION: (6)
<223> OTHER INFORMATION: Residue has Acetamidomethyl, tert-
      Acetamidomethyl or tert-butyl protecting group
<220> FEATURE:
<221> NAME/KEY: MOD_RES
<222> LOCATION: (9)
<223> OTHER INFORMATION: AMIDATION

<400> SEQUENCE: 25

Cys Tyr Ile Gln Asn Cys Pro Leu Gly
 1               5

<210> SEQ ID NO 26
<211> LENGTH: 6
<212> TYPE: PRT
<213> ORGANISM: Artificial Sequence
<220> FEATURE:
<223> OTHER INFORMATION: Description of Artificial Sequence:  Cyclic
      peptide with classical cadherin cell adhesion
      recognition sequence
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 26

Cys Ser His Ala Val Cys
 1               5

<210> SEQ ID NO 27
<211> LENGTH: 6
<212> TYPE: PRT
<213> ORGANISM: Artificial Sequence
<220> FEATURE:
<223> OTHER INFORMATION: Description of Artificial Sequence:  Cyclic
      peptide with classical cadherin cell adhesion
      recognition sequence
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 27

Cys His Ala Val Ser Cys
 1               5

<210> SEQ ID NO 28
<211> LENGTH: 8
<212> TYPE: PRT
<213> ORGANISM: Artificial Sequence
<220> FEATURE:
<223> OTHER INFORMATION: Description of Artificial Sequence:  Cyclic
      peptide with classical cadherin cell adhesion
      recognition sequence
```

```
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 28

Cys Ser His Ala Val Ser Ser Cys
 1               5

<210> SEQ ID NO 29
<211> LENGTH: 5
<212> TYPE: PRT
<213> ORGANISM: Artificial Sequence
<220> FEATURE:
<223> OTHER INFORMATION: Description of Artificial Sequence:  Cyclic
      peptide with classical cadherin cell adhesion
      recognition sequence
<220> FEATURE:
<223> OTHER INFORMATION: Cyclic Peptide may comprise N-terminal
      modification such as acetyl or alkoxybenzyl group
      and/or C-terminal modifications such as amide or
      ester group
<220> FEATURE:
<221> NAME/KEY: MOD_RES
<222> LOCATION: (5)
<223> OTHER INFORMATION: Where Xaa is beta,beta-dimethyl cysteine

<400> SEQUENCE: 29

Cys His Ala Val Xaa
 1               5

<210> SEQ ID NO 30
<211> LENGTH: 10
<212> TYPE: PRT
<213> ORGANISM: Artificial Sequence
<220> FEATURE:
<223> OTHER INFORMATION: Description of Artificial Sequence:  Cyclic
      Peptide with classical cadherin cell adhesion
      recognition sequence
<220> FEATURE:
<223> OTHER INFORMATION: Cyclic Peptide may comprise N-terminal
      modification such as acetyl or alkoxybenzyl group
      and/or C-terminal modifications such as amide or
      ester group
<220> FEATURE:
<221> NAME/KEY: MOD_RES
<222> LOCATION: (2)
<223> OTHER INFORMATION: Where Xaa is beta,beta-tetramethylene cysteine

<400> SEQUENCE: 30

Ile Xaa Tyr Ser His Ala Val Ser Cys Glu
 1               5                  10

<210> SEQ ID NO 31
<211> LENGTH: 10
<212> TYPE: PRT
<213> ORGANISM: Artificial Sequence
<220> FEATURE:
<223> OTHER INFORMATION: Description of Artificial Sequence:  Cyclic
      Peptide with classical cadherin cell adhesion
      recognition sequence
<220> FEATURE:
<223> OTHER INFORMATION: Cyclic Peptide may comprise N-terminal
      modification such as acetyl or alkoxybenzyl group
      and/or C-terminal modifications such as amide or
      ester group
<220> FEATURE:
<221> NAME/KEY: MOD_RES
<222> LOCATION: (2)
<223> OTHER INFORMATION: Where Xaa is beta,beta-pentamethylene cysteine

<400> SEQUENCE: 31
```

```
Ile Xaa Tyr Ser His Ala Val Ser Ser Cys
 1               5                  10

<210> SEQ ID NO 32
<211> LENGTH: 9
<212> TYPE: PRT
<213> ORGANISM: Artificial Sequence
<220> FEATURE:
<223> OTHER INFORMATION: Description of Artificial Sequence: Cyclic
      peptide with classical cadherin cell adhesion
      recognition sequence
<220> FEATURE:
<223> OTHER INFORMATION: Cyclic Peptide may comprise N-terminal
      modification such as acetyl or alkoxybenzyl group
      and/or C-terminal modifications such as amide or
      ester group
<220> FEATURE:
<221> NAME/KEY: MOD_RES
<222> LOCATION: (1)
<223> OTHER INFORMATION: Where Xaa is beta-mercaptopropionic acid

<400> SEQUENCE: 32

Xaa Tyr Ser His Ala Val Ser Ser Cys
 1               5

<210> SEQ ID NO 33
<211> LENGTH: 9
<212> TYPE: PRT
<213> ORGANISM: Artificial Sequence
<220> FEATURE:
<223> OTHER INFORMATION: Description of Artificial Sequence: Cyclic
      peptide with classical cadherin cell adhesion
      recognition sequence
<220> FEATURE:
<223> OTHER INFORMATION: Cyclic Peptide may comprise N-terminal
      modification such as acetyl or alkoxybenzyl group
      and/or C-terminal modifications such as amide or
      ester group
<220> FEATURE:
<221> NAME/KEY: MOD_RES
<222> LOCATION: (1)
<223> OTHER INFORMATION: Where Xaa is
      beta,beta-pentamethylene-beta-mercaptopropionic
      acid

<400> SEQUENCE: 33

Xaa Tyr Ser His Ala Val Ser Ser Cys
 1               5

<210> SEQ ID NO 34
<211> LENGTH: 6
<212> TYPE: PRT
<213> ORGANISM: Artificial Sequence
<220> FEATURE:
<223> OTHER INFORMATION: Description of Artificial Sequence: Cyclic
      peptide with classical cadherin cell adhesion
      recognition sequence
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 34

Ser His Ala Val Ser Ser
 1               5

<210> SEQ ID NO 35
<211> LENGTH: 5
<212> TYPE: PRT
<213> ORGANISM: Artificial Sequence
```

```
<220> FEATURE:
<223> OTHER INFORMATION: Description of Artificial Sequence:  Cyclic
      peptide with classical cadherin cell adhesion
      recognition sequence
<220> FEATURE:
<221> NAME/KEY: MOD_RES
<222> LOCATION: (4)
<223> OTHER INFORMATION: Where Serine is D-Serine

<400> SEQUENCE: 35

His Ala Val Ser Ser
 1               5

<210> SEQ ID NO 36
<211> LENGTH: 4
<212> TYPE: PRT
<213> ORGANISM: Artificial Sequence
<220> FEATURE:
<223> OTHER INFORMATION: Description of Artificial Sequence:
      Synthesized cyclic peptide

<400> SEQUENCE: 36

Trp Gly Gly Trp
 1

<210> SEQ ID NO 37
<211> LENGTH: 5
<212> TYPE: PRT
<213> ORGANISM: Artificial Sequence
<220> FEATURE:
<223> OTHER INFORMATION: Description of Artificial Sequence:  Cyclic
      peptide with cadherin cell adhesion recognition
      sequence
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 37

Lys His Ala Val Asp
 1               5

<210> SEQ ID NO 38
<211> LENGTH: 5
<212> TYPE: PRT
<213> ORGANISM: Artificial Sequence
<220> FEATURE:
<223> OTHER INFORMATION: Description of Artificial Sequence:  Cyclic
      control peptide
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 38

Lys His Gly Val Asp
 1               5

<210> SEQ ID NO 39
<211> LENGTH: 6
<212> TYPE: PRT
<213> ORGANISM: Artificial Sequence
<220> FEATURE:
<223> OTHER INFORMATION: Description of Artificial Sequence:  Cyclic
      control peptide
<220> FEATURE:
<223> OTHER INFORMATION: Cyclic Peptide may comprise N-terminal
      modification such as acetyl or alkoxybenzyl group
      and/or C-terminal modifications such as amide or
``` ester group

<400> SEQUENCE: 39

Cys His Gly Val Asp Cys
1               5

<210> SEQ ID NO 40
<211> LENGTH: 6
<212> TYPE: PRT
<213> ORGANISM: Artificial Sequence
<220> FEATURE:
<223> OTHER INFORMATION: Description of Artificial Sequence:  Cyclic
      control peptide
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 40

Cys Ala His Gly Val Cys
1               5

<210> SEQ ID NO 41
<211> LENGTH: 8
<212> TYPE: PRT
<213> ORGANISM: Artificial Sequence
<220> FEATURE:
<223> OTHER INFORMATION: Description of Artificial Sequence:  Cyclic
      control peptide
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 41

Cys Ala His Gly Val Asp Ile Cys
1               5

<210> SEQ ID NO 42
<211> LENGTH: 8
<212> TYPE: PRT
<213> ORGANISM: Artificial Sequence
<220> FEATURE:
<223> OTHER INFORMATION: Description of Artificial Sequence:  Cyclic
      control peptide
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 42

Cys Arg Ala His Gly Val Asp Cys
1               5

<210> SEQ ID NO 43
<211> LENGTH: 8
<212> TYPE: PRT
<213> ORGANISM: Artificial Sequence
<220> FEATURE:
<223> OTHER INFORMATION: Description of Artificial Sequence:  Cyclic
      peptide with classical cadherin cell adhesion
      recognition sequence
<220> FEATURE:
<223> OTHER INFORMATION: Cyclic Peptide may comprise N-terminal
      modification such as acetyl or alkoxybenzyl group
      and/or C-terminal modifications such as amide or
      ester group

```
<400> SEQUENCE: 43

Cys Leu Arg Ala His Ala Val Cys
 1               5

<210> SEQ ID NO 44
<211> LENGTH: 8
<212> TYPE: PRT
<213> ORGANISM: Artificial Sequence
<220> FEATURE:
<223> OTHER INFORMATION: Description of Artificial Sequence:  Cyclic
      control peptide
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 44

Cys Leu Arg Ala His Gly Val Cys
 1               5

<210> SEQ ID NO 45
<211> LENGTH: 9
<212> TYPE: PRT
<213> ORGANISM: Artificial Sequence
<220> FEATURE:
<223> OTHER INFORMATION: Description of Artificial Sequence:  Cyclic
      control peptide
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 45

Cys Leu Arg Ala His Gly Val Asp Cys
 1               5

<210> SEQ ID NO 46
<211> LENGTH: 7
<212> TYPE: PRT
<213> ORGANISM: Artificial Sequence
<220> FEATURE:
<223> OTHER INFORMATION: Description of Artificial Sequence:  Cyclic
      control peptide
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 46

Cys Ala His Gly Val Asp Cys
 1               5

<210> SEQ ID NO 47
<211> LENGTH: 6
<212> TYPE: PRT
<213> ORGANISM: Artificial Sequence
<220> FEATURE:
<223> OTHER INFORMATION: Description of Artificial Sequence:  Cyclic
      control peptide
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 47

Cys Ser His Gly Val Cys
```

<210> SEQ ID NO 48
<211> LENGTH: 6
<212> TYPE: PRT
<213> ORGANISM: Artificial Sequence
<220> FEATURE:
<223> OTHER INFORMATION: Description of Artificial Sequence: Cyclic
      control peptide
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 48

Cys His Gly Val Ser Cys
 1               5

<210> SEQ ID NO 49
<211> LENGTH: 7
<212> TYPE: PRT
<213> ORGANISM: Artificial Sequence
<220> FEATURE:
<223> OTHER INFORMATION: Description of Artificial Sequence: Cyclic
      peptide with classical cadherin cell adhesion
      recognition sequence
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 49

Cys Ser His Ala Val Ser Cys
 1               5

<210> SEQ ID NO 50
<211> LENGTH: 7
<212> TYPE: PRT
<213> ORGANISM: Artificial Sequence
<220> FEATURE:
<223> OTHER INFORMATION: Description of Artificial Sequence: Cyclic
      control peptide
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 50

Cys Ser His Gly Val Ser Cys
 1               5

<210> SEQ ID NO 51
<211> LENGTH: 8
<212> TYPE: PRT
<213> ORGANISM: Artificial Sequence
<220> FEATURE:
<223> OTHER INFORMATION: Description of Artificial Sequence: Cyclic
      control peptide
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 51

Cys Ser His Gly Val Ser Ser Cys
 1               5

```
<210> SEQ ID NO 52
<211> LENGTH: 7
<212> TYPE: PRT
<213> ORGANISM: Artificial Sequence
<220> FEATURE:
<223> OTHER INFORMATION: Description of Artificial Sequence: Cyclic
      peptide with classical cadherin cell adhesion
      recognition sequence
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 52

Cys His Ala Val Ser Ser Cys
  1               5

<210> SEQ ID NO 53
<211> LENGTH: 7
<212> TYPE: PRT
<213> ORGANISM: Artificial Sequence
<220> FEATURE:
<223> OTHER INFORMATION: Description of Artificial Sequence: Cyclic
      control peptide
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 53

Cys His Gly Val Ser Ser Cys
  1               5

<210> SEQ ID NO 54
<211> LENGTH: 5
<212> TYPE: PRT
<213> ORGANISM: Artificial Sequence
<220> FEATURE:
<223> OTHER INFORMATION: Description of Artificial Sequence: Cyclic
      peptide with classical cadherin cell adhesion
      recognition sequence
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 54

Cys Val Ala His Cys
  1               5

<210> SEQ ID NO 55
<211> LENGTH: 5
<212> TYPE: PRT
<213> ORGANISM: Artificial Sequence
<220> FEATURE:
<223> OTHER INFORMATION: Description of Artificial Sequence: Cyclic
      control peptide
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 55

Cys Val Gly His Cys
  1               5
```

```
<210> SEQ ID NO 56
<211> LENGTH: 5
<212> TYPE: PRT
<213> ORGANISM: Artificial Sequence
<220> FEATURE:
<223> OTHER INFORMATION: Description of Artificial Sequence:  Cyclic
      control peptide
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 56

Asp His Gly Val Lys
 1               5

<210> SEQ ID NO 57
<211> LENGTH: 5
<212> TYPE: PRT
<213> ORGANISM: Artificial Sequence
<220> FEATURE:
<223> OTHER INFORMATION: Description of Artificial Sequence:  Cyclic
      control peptide
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 57

Lys His Gly Val Glu
 1               5

<210> SEQ ID NO 58
<211> LENGTH: 6
<212> TYPE: PRT
<213> ORGANISM: Artificial Sequence
<220> FEATURE:
<223> OTHER INFORMATION: Description of Artificial Sequence:  Cyclic
      control peptide
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 58

Ala His Gly Val Asp Ile
 1               5

<210> SEQ ID NO 59
<211> LENGTH: 6
<212> TYPE: PRT
<213> ORGANISM: Artificial Sequence
<220> FEATURE:
<223> OTHER INFORMATION: Description of Artificial Sequence:  Cyclic
      control peptide
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 59

Ser His Gly Val Ser Ser
 1               5

<210> SEQ ID NO 60
<211> LENGTH: 8
<212> TYPE: PRT
```

```
<213> ORGANISM: Artificial Sequence
<220> FEATURE:
<223> OTHER INFORMATION: Description of Artificial Sequence:  Cyclic
      peptide with classical cadherin cell adhesion
      recognition sequence
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 60

Lys Ser His Ala Val Ser Ser Asp
  1               5

<210> SEQ ID NO 61
<211> LENGTH: 8
<212> TYPE: PRT
<213> ORGANISM: Artificial Sequence
<220> FEATURE:
<223> OTHER INFORMATION: Description of Artificial Sequence:  Cyclic
      control peptide
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 61

Lys Ser His Gly Val Ser Ser Asp
  1               5

<210> SEQ ID NO 62
<211> LENGTH: 7
<212> TYPE: PRT
<213> ORGANISM: Artificial Sequence
<220> FEATURE:
<223> OTHER INFORMATION: Description of Artificial Sequence:  Cyclic
      peptide with classical cadherin cell adhesion
      recognition sequence
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 62

Cys His Ala Val Asp Ile Cys
  1               5

<210> SEQ ID NO 63
<211> LENGTH: 8
<212> TYPE: PRT
<213> ORGANISM: Artificial Sequence
<220> FEATURE:
<223> OTHER INFORMATION: Description of Artificial Sequence:  Cyclic
      peptide with classical cadherin cell adhesion
      recognition sequence
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 63

Cys His Ala Val Asp Ile Asn Cys
  1               5

<210> SEQ ID NO 64
<211> LENGTH: 4
<212> TYPE: PRT
```

```
<213> ORGANISM: Unknown
<220> FEATURE:
<223> OTHER INFORMATION: Description of Unknown Organism:  Occluding
      cell adhesion recognition sequence

<400> SEQUENCE: 64

Leu Tyr His Tyr
 1

<210> SEQ ID NO 65
<211> LENGTH: 9
<212> TYPE: PRT
<213> ORGANISM: Unknown
<220> FEATURE:
<223> OTHER INFORMATION: Description of Unknown Organism:  Nonclassical
      cadherin cell adhesion recognition sequence
<220> FEATURE:
<221> NAME/KEY: MOD_RES
<222> LOCATION: (1)
<223> OTHER INFORMATION: Where Xaa is an independently selected amino
      acid residue
<220> FEATURE:
<221> NAME/KEY: MOD_RES
<222> LOCATION: (3)
<223> OTHER INFORMATION: Where Xaa is an independently selected amino
      acid residue
<220> FEATURE:
<221> NAME/KEY: MOD_RES
<222> LOCATION: (4)
<223> OTHER INFORMATION: Where Xaa is Isoleucine, Leucine or Valine
<220> FEATURE:
<221> NAME/KEY: MOD_RES
<222> LOCATION: (5)
<223> OTHER INFORMATION: Where Xaa is Aspartic Acid, Asparagine or
      Glutamic Acid
<220> FEATURE:
<221> NAME/KEY: MOD_RES
<222> LOCATION: (6)..(7)
<223> OTHER INFORMATION: Where Xaa is an independently selected amino
      acid residue
<220> FEATURE:
<221> NAME/KEY: MOD_RES
<222> LOCATION: (8)
<223> OTHER INFORMATION: Where Xaa is Serine, Threonine or Asparagine

<400> SEQUENCE: 65

Xaa Phe Xaa Xaa Xaa Xaa Xaa Xaa Gly
 1               5

<210> SEQ ID NO 66
<211> LENGTH: 4
<212> TYPE: PRT
<213> ORGANISM: Unknown
<220> FEATURE:
<223> OTHER INFORMATION: Description of Unknown Organism:
       Representative claudin cell adhesion recognition sequence

<400> SEQUENCE: 66

Ile Tyr Ser Tyr
 1

<210> SEQ ID NO 67
<211> LENGTH: 4
<212> TYPE: PRT
<213> ORGANISM: Unknown
<220> FEATURE:
<223> OTHER INFORMATION: Description of Unknown Organism:
       Representative claudin cell adhesion recognition sequence

<400> SEQUENCE: 67

Thr Ser Ser Tyr
 1
```

```
<210> SEQ ID NO 68
<211> LENGTH: 4
<212> TYPE: PRT
<213> ORGANISM: Unknown
<220> FEATURE:
<223> OTHER INFORMATION: Description of Unknown Organism:
      Representative claudin cell adhesion recognition sequence

<400> SEQUENCE: 68

Val Thr Ala Phe
  1

<210> SEQ ID NO 69
<211> LENGTH: 4
<212> TYPE: PRT
<213> ORGANISM: Unknown
<220> FEATURE:
<223> OTHER INFORMATION: Description of Unknown Organism:
      Representative claudin cell adhesion recognition sequence

<400> SEQUENCE: 69

Val Ser Ala Phe
  1

<210> SEQ ID NO 70
<211> LENGTH: 9
<212> TYPE: PRT
<213> ORGANISM: Artificial Sequence
<220> FEATURE:
<223> OTHER INFORMATION: Description of Artificial Seq
      uence:  Cyclic peptide with classical cadherin cell adhesion
      recognition sequence
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 70

Cys His Ala Val Asp Ile Asn Gly Cys
  1               5

<210> SEQ ID NO 71
<211> LENGTH: 14
<212> TYPE: PRT
<213> ORGANISM: Homo sapiens
<220> FEATURE:
<223> OTHER INFORMATION: N-cadherin with HAV cell adhesion recognition
      sequence and flanking amino acids

<400> SEQUENCE: 71

Arg Phe His Leu Arg Ala His Ala Val Asp Ile Asn Gly Asn
  1               5                  10

<210> SEQ ID NO 72
<211> LENGTH: 12
<212> TYPE: PRT
<213> ORGANISM: Homo sapiens
<220> FEATURE:
<223> OTHER INFORMATION: E-cadherin with HAV cell adhesion recognition
      sequence and flanking amino acids

<400> SEQUENCE: 72

Thr Leu Phe Ser His Ala Val Ser Ser Asn Gly Asn
  1               5                  10

<210> SEQ ID NO 73
```

```
<211> LENGTH: 22
<212> TYPE: DNA
<213> ORGANISM: Artificial Sequence
<220> FEATURE:
<223> OTHER INFORMATION: Description of Artificial Sequence: E-cadherin
      specific primer

<400> SEQUENCE: 73
ccttccccca acacgtcccc cc                                              22

<210> SEQ ID NO 74
<211> LENGTH: 20
<212> TYPE: DNA
<213> ORGANISM: Artificial Sequence
<220> FEATURE:
<223> OTHER INFORMATION: Description of Artificial Sequence: E-cadherin
      specific primer

<400> SEQUENCE: 74
tctccacctc cttcttcatc                                                 20

<210> SEQ ID NO 75
<211> LENGTH: 21
<212> TYPE: DNA
<213> ORGANISM: Artificial Sequence
<220> FEATURE:
<223> OTHER INFORMATION: Description of Artificial Sequence:  N-cadherin
      specific primer

<400> SEQUENCE: 75
caagagcttg tcacaatcag g                                               21

<210> SEQ ID NO 76
<211> LENGTH: 19
<212> TYPE: DNA
<213> ORGANISM: Artificial Sequence
<220> FEATURE:
<223> OTHER INFORMATION: Description of Artificial Sequence:  N-cadherin
      specific primer

<400> SEQUENCE: 76
catttggatc atccgcatc                                                  19

<210> SEQ ID NO 77
<211> LENGTH: 8
<212> TYPE: PRT
<213> ORGANISM: Unknown
<220> FEATURE:
<223> OTHER INFORMATION: Description of Unknown Organism:  Claudin cell
      adhesion recognition sequence
<220> FEATURE:
<221> NAME/KEY: MOD_RES
<222> LOCATION: (2)
<223> OTHER INFORMATION: Where Xaa is either Lysine or arginine
<220> FEATURE:
<221> NAME/KEY: MOD_RES
<222> LOCATION: (3)..(4)
<223> OTHER INFORMATION: Where Xaa is an independently selected amino
      acid residue
<220> FEATURE:
<221> NAME/KEY: MOD_RES
<222> LOCATION: (5)
<223> OTHER INFORMATION: Where Xaa is either Serine or Alanine
<220> FEATURE:
<221> NAME/KEY: MOD_RES
<222> LOCATION: (6)
<223> OTHER INFORMATION: Where Xaa is either Tyrosine or Phenylalanine
<220> FEATURE:
<221> NAME/KEY: MOD_RES
<222> LOCATION: (7)
<223> OTHER INFORMATION: Where Xaa is an independently selected amino
```

-continued acid residue

<400> SEQUENCE: 77

Trp Xaa Xaa Xaa Xaa Xaa Xaa Gly
 1               5

<210> SEQ ID NO 78
<211> LENGTH: 7
<212> TYPE: PRT
<213> ORGANISM: Artificial Sequence
<220> FEATURE:
<223> OTHER INFORMATION: Description of Artificial Sequence:  Cyclic
      peptide with classical cadherin cell adhesion
      recognition sequence
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 78

Ser His Ala Val Asp Ser Ser
 1               5

<210> SEQ ID NO 79
<211> LENGTH: 10
<212> TYPE: PRT
<213> ORGANISM: Artificial Sequence
<220> FEATURE:
<223> OTHER INFORMATION: Description of Artificial Sequence:
      Synthesized Cyclic Peptide
<220> FEATURE:
<221> NAME/KEY: MOD_RES
<222> LOCATION: (1)
<223> OTHER INFORMATION: 9-fluorenylmethoxycarbonyl protecting group
<220> FEATURE:
<221> NAME/KEY: MOD_RES
<222> LOCATION: (2)
<223> OTHER INFORMATION: tert-butyl protecting group
<220> FEATURE:
<221> NAME/KEY: MOD_RES
<222> LOCATION: (4)
<223> OTHER INFORMATION: tert-butyl protecting group
<220> FEATURE:
<221> NAME/KEY: MOD_RES
<222> LOCATION: (6)
<223> OTHER INFORMATION: t-butoxycarbonyl protecting group
<220> FEATURE:
<221> NAME/KEY: MOD_RES
<222> LOCATION: (7)
<223> OTHER INFORMATION: tert-butyl protecting group
<220> FEATURE:
<221> NAME/KEY: MOD_RES
<222> LOCATION: (9)
<223> OTHER INFORMATION: tert-butyl protecting group
<220> FEATURE:
<221> NAME/KEY: MOD_RES
<222> LOCATION: (10)
<223> OTHER INFORMATION: Methoxy terminal group

<400> SEQUENCE: 79

Cys Asp Gly Tyr Pro Lys Asp Cys Lys Gly
 1               5                  10

<210> SEQ ID NO 80
<211> LENGTH: 10
<212> TYPE: PRT
<213> ORGANISM: Artificial Sequence
<220> FEATURE:
<223> OTHER INFORMATION: Description of Artificial Sequence:
      Synthesized cyclic peptide
<220> FEATURE:
<221> NAME/KEY: MOD_RES -continued

```
<222> LOCATION: (1)
<223> OTHER INFORMATION: t-butoxycarbonyl protecting group
<220> FEATURE:
<221> NAME/KEY: MOD_RES
<222> LOCATION: (5)..(6)
<223> OTHER INFORMATION: tert-butyl protecting group

<400> SEQUENCE: 80

Cys Gly Asn Leu Ser Thr Cys Met Leu Gly
1               5                   10

<210> SEQ ID NO 81
<211> LENGTH: 9
<212> TYPE: PRT
<213> ORGANISM: Artificial Sequence
<220> FEATURE:
<223> OTHER INFORMATION: Description of Artificial Sequence:
      Synthesized cyclic peptide
<220> FEATURE:
<221> NAME/KEY: MOD_RES
<222> LOCATION: (9)
<223> OTHER INFORMATION: AMIDATION

<400> SEQUENCE: 81

Cys Tyr Ile Gln Asn Cys Pro Leu Gly
1               5
```